(12) United States Patent
Borrero et al.

(10) Patent No.: US 12,409,079 B2
(45) Date of Patent: Sep. 9, 2025

(54) ELASTOMERIC ABSORBENT ARTICLES

(71) Applicant: Drylock Technologies NV, Zele (BE)

(72) Inventors: Ricardo Borrero, Eau Claire, WI (US); Frank Glaug, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 0 days.

(21) Appl. No.: 18/482,607

(22) Filed: Oct. 6, 2023

(65) Prior Publication Data
US 2024/0091074 A1    Mar. 21, 2024

Related U.S. Application Data

(63) Continuation of application No. 16/084,961, filed as application No. PCT/EP2017/056444 on Mar. 17, 2017, now Pat. No. 11,813,145.
(Continued)

(51) Int. Cl.
*A61F 13/15*     (2006.01)
*A61F 13/01*     (2024.01)
(Continued)

(52) U.S. Cl.
CPC .. *A61F 13/49015* (2013.01); *A61F 13/01029* (2024.01); *A61F 13/01038* (2024.01);
(Continued)

(58) Field of Classification Search
CPC .......... A61F 13/49015; A61F 13/01029; A61F 13/01038; A61F 13/0226; A61F 13/15707;
(Continued)

(56) References Cited

U.S. PATENT DOCUMENTS

| | | | |
|---|---|---|---|
| 5,116,662 A | | 5/1992 | Morman |
| 5,226,992 A | * | 7/1993 | Morman .................. D04H 1/56 |
| | | | 156/181 |

(Continued)

FOREIGN PATENT DOCUMENTS

| | | | | |
|---|---|---|---|---|
| EP | 0650714 A1 | 5/1995 | | |
| WO | WO-0035398 A1 | * | 6/2000 | ........... A61F 13/565 |

(Continued)

OTHER PUBLICATIONS

"U.S. Appl. No. 16/084,961, Advisory Action mailed May 22, 2023", 3 pgs.
(Continued)

*Primary Examiner* — Jacqueline F Stephens
(74) *Attorney, Agent, or Firm* — Schwegman Lundberg & Woessner, P.A.

(57) ABSTRACT

The present invention includes disposable absorbent articles, such as disposable undergarment, diapers, other garments, and wound care dressings, having an elastomeric material disposed between two substrate layers and an absorbent core system that disposed on top of or between the two substrate layers. This invention may also include a disposable article having an elastomeric material disposed between two substrate layers without an absorbent core. The inclusion of an stretch adhesive in the construction of the article in various portions of the article (e.g., fastening tabs, front and/or rear sections, entire article, etc.) results in improved securement of the article to a wearer for reducing the risk of leakage and further improving comfort for the wearer. Furthermore, the inclusion of a stretch adhesive can provide a smooth contoured fit to a wearer, thereby improving appearance and self-confidence for the wearer.

21 Claims, 50 Drawing Sheets

Related U.S. Application Data

(60) Provisional application No. 62/449,388, filed on Jan. 23, 2017, provisional application No. 62/432,851, filed on Dec. 12, 2016, provisional application No. 62/337,111, filed on May 16, 2016, provisional application No. 62/310,005, filed on Mar. 18, 2016.

(51) Int. Cl.
  *A61F 13/0203* (2024.01)
  *A61F 13/49* (2006.01)

(52) U.S. Cl.
  CPC .... *A61F 13/0226* (2013.01); *A61F 13/15699* (2013.01); *A61F 13/15707* (2013.01); *A61F 13/49007* (2013.01); *A61F 13/49011* (2013.01); *A61F 13/49012* (2013.01); *A61F 13/49014* (2013.01); *A61F 13/49017* (2013.01); *A61F 13/49019* (2013.01); *A61F 13/4902* (2013.01)

(58) Field of Classification Search
  CPC .......... A61F 13/49007; A61F 13/49011; A61F 13/49012; A61F 13/49014; A61F 13/49017; A61F 13/19019; A61F 13/4902
  See application file for complete search history.

(56) References Cited

U.S. PATENT DOCUMENTS

| | | | |
|---|---|---|---|
| 5,584,829 A | 12/1996 | Lavash et al. | |
| 5,601,542 A | 2/1997 | Melius et al. | |
| 5,787,732 A | 8/1998 | Perron et al. | |
| 7,686,794 B2 | 3/2010 | Mitchell | |
| 7,901,390 B1* | 3/2011 | Ashton | A61F 13/49011 |
| | | | 604/385.24 |
| D692,208 S | 10/2013 | LaCour-Phillippi | |
| 2003/0069557 A1 | 4/2003 | Driskell et al. | |
| 2003/0100877 A1* | 5/2003 | Erdman | A61L 15/46 |
| | | | 424/769 |
| 2003/0176846 A1 | 9/2003 | Karami | |
| 2003/0196252 A1 | 10/2003 | Blakely | |
| 2004/0054340 A1 | 3/2004 | Mitchell | |
| 2004/0060649 A1 | 4/2004 | Van Gompel et al. | |
| 2004/0122412 A1 | 6/2004 | Morman et al. | |
| 2004/0243083 A1 | 12/2004 | Matsuda et al. | |
| 2005/0010188 A1 | 1/2005 | Glaug et al. | |
| 2005/0148981 A1 | 7/2005 | Price et al. | |
| 2005/0177125 A1* | 8/2005 | Kondo | A61F 13/505 |
| | | | 604/394 |
| 2005/0215971 A1 | 9/2005 | Roe et al. | |
| 2007/0199134 A1 | 8/2007 | Duckman et al. | |
| 2008/0287897 A1* | 11/2008 | Guzman Reyes | A61F 13/15699 |
| | | | 604/385.27 |
| 2009/0062761 A1 | 3/2009 | Goerg-Wood et al. | |
| 2019/0076304 A1 | 3/2019 | Borrero et al. | |

FOREIGN PATENT DOCUMENTS

| | | |
|---|---|---|
| WO | WO-0234182 A2 | 5/2002 |
| WO | WO-2005110311 A1 | 11/2005 |
| WO | WO-2015195467 A1 | 12/2015 |

OTHER PUBLICATIONS

"U.S. Appl. No. 16/084,961, Final Office Action mailed Feb. 28, 2023", 11 pgs.
"U.S. Appl. No. 16/084,961, Final Office Action mailed Apr. 4, 2022", 15 pgs.
"U.S. Appl. No. 16/084,961, Non Final Office Action mailed Jul. 7, 2021", 14 pgs.
"U.S. Appl. No. 16/084,961, Non Final Office Action mailed Jul. 22, 2022", 15 pgs.
"U.S. Appl. No. 16/084,961, Notice of Allowance mailed Jul. 6, 2023", 10 pgs.
"U.S. Appl. No. 16/084,961, Response filed Jan. 6, 2022 to Non Final Office Action mailed Jul. 7, 2021", 14 pgs.
"U.S. Appl. No. 16/084,961, Response filed Apr. 26, 2023 to Final Office Action mailed Feb. 28, 2023", 11 pgs.
"U.S. Appl. No. 16/084,961, Response filed Jun. 3, 2022 to Final Office Action mailed Apr. 4, 2022", 19 pgs.
"U.S. Appl. No. 16/084,961, Response filed Dec. 20, 2022 to Non Final Office Action mailed Jul. 22, 2022", 18 pgs.
"International Application Serial No. PCT/EP2017/056444, International Search Report mailed Jul. 13, 2017", (Jul. 13, 2017), 6 pgs.
"International Application Serial No. PCT/EP2017/056444, Written Opinion mailed Jul. 13, 2017", (Jul. 13, 2017), 10 pgs.

\* cited by examiner

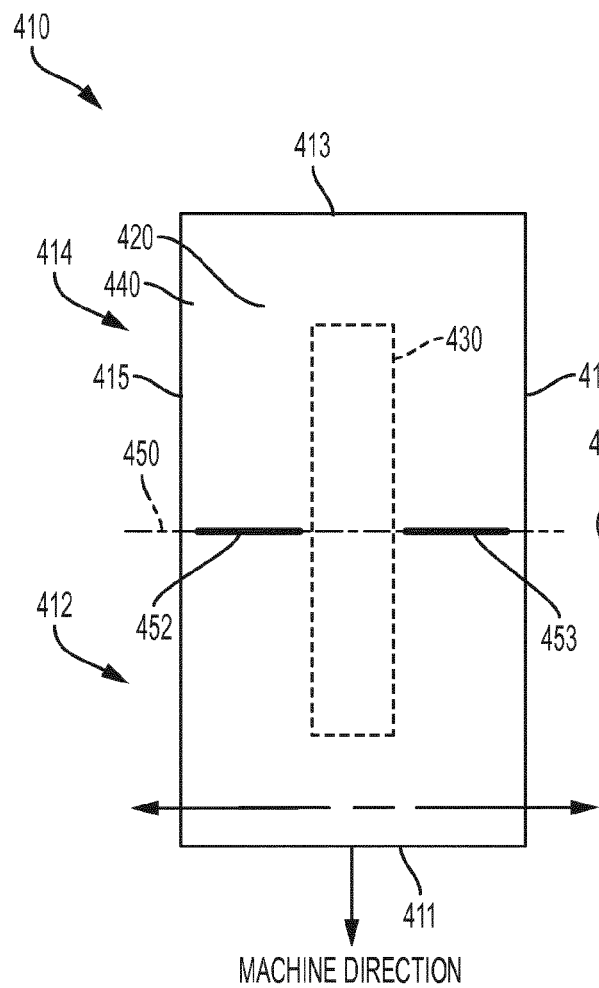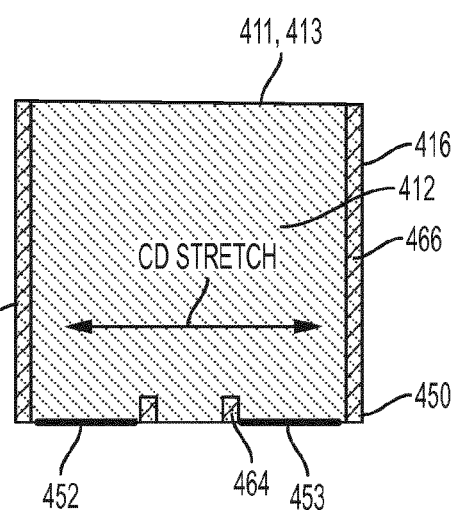
FIG. 33A
FIG. 33B

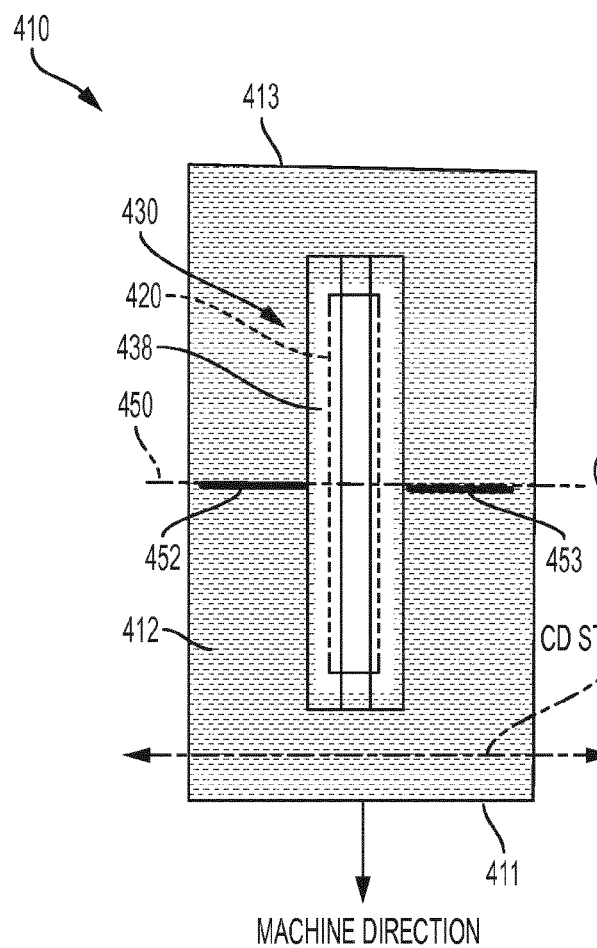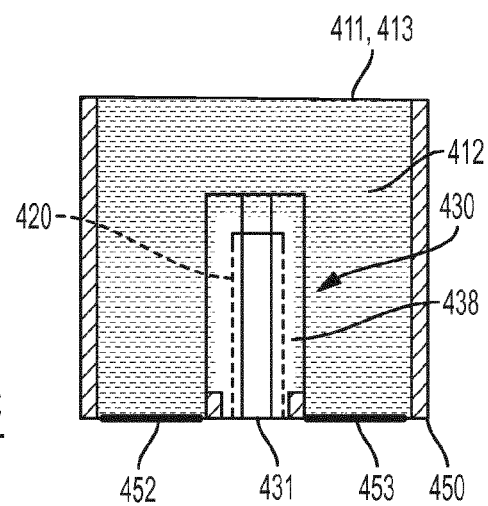
FIG. 35A
FIG. 35B

FIG. 42A
FIG. 42B
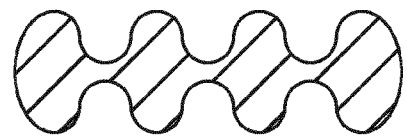
FIG. 42C
FIG. 42D

ELASTOMERIC ABSORBENT ARTICLES

CROSS-REFERENCE TO RELATED APPLICATIONS

This application is a continuation of U.S. application Ser. No. 16/084,961, filed Sep. 13, 2018, which is a U.S. National Stage Filing under 35 U.S.C. 371 from International Application No. PCT/EP2017/056444, filed on Mar. 17, 2017, and published as WO2017/158185 on Sep. 21, 2017, which claims the benefit of, and priority to, U.S. Provisional Application Nos. 62/310,005, filed Mar. 18, 2016, 62/337,111, filed May 16, 2016, 62/432,851, filed Dec. 12, 2016, and 62/449,388, filed Jan. 23, 2017, the contents of each of which are hereby incorporated by reference herein in their entireties.

FIELD

The present disclosure relates generally to disposable absorbent articles, and, more particularly, to a disposable undergarment (adult and child), diapers (adult and child), garments, wound care dressings and the like, having an elastomeric material and an absorbent core disposed between two substrate layers or elastic material disposed between two substrate layers and absorbent core system applied on top of it, thereby resulting in improved securement of the article to a wearer for reducing the risk of leakage and further improving comfort for the wearer.

BACKGROUND

There are several types of commercially available products for the absorption of bodily fluids. Such absorbent products are available in different types, designs, and dimensions, each one having one or more unique features. For example, training pants, baby diapers, adult diapers, and incontinence guards are products designed for the containment of urine and excrement. There are other types of disposable absorbent articles, such as feminine hygiene products (e.g., heavy and light incontinence pads, pantyliners, etc.) that are designed to contain and absorb urine and/or menses by female wearers. Another type of absorbent article includes underpads configured to absorb and collect body fluid discharge from a person who may be generally confined to a bed or chair, or may otherwise be immobilized.

Currently known absorbent products are often constructed from multiple components that are assembled together to form the final product. Often this means that a front and a rear portion are attached to a crotch portion, the crotch portion having the absorbent feature. Additionally, in order to hold the product close to the wearer's body so that it does not fall down, elastic strands or other features are usually provided around the leg openings and the waist openings. However, this type of construction often leads to discomfort to the wearer from the rubbing of the overlapping components and/or seams holding the components together. Additionally, the elastic elements around the leg and waist openings used to hold the garment against the wearer often contribute to leakage. The leakage is due to the gapping between the article and the wearer's body caused by the elastic gatherings, the gapping providing an inconsistent seal. Furthermore, the use different components assembled together and elastic or other stretch materials at the leg and waist openings, along with relatively non-stretchable material throughout large portions of the remainder of the article, contribute to a bulky appearance when worn Improperly-fit absorbent garments can lead to a number of different issues for the wearer of the garment. For example, an improperly-fit garment can be uncomfortable, can adversely affect the wearer's mobility (actual or perceived), and there can be an increased chance of leakage. This in undesirable to a wearer and can be cause for embarrassment and shame. Thus, there exists a need to minimize leakage at the openings and providing a smooth contoured fit to the body of the wearer.

SUMMARY

The present invention provides disposable absorbent articles, such as disposable undergarment, diapers, other garments, and wound care dressings, having an elastomeric material and an absorbent core disposed between two substrate layers. In addition, the absorbent core system can be applied on top of the two substrate layers that contain an elastomeric material disposed between them. The inclusion of an elastomeric material, such as a stretch adhesive, in the construction of the article in various portions of the article (e.g., fastening tabs, front and/or rear sections, entire article, etc.) results in improved securement of the article to a wearer for reducing the risk of leakage and further improving comfort for the wearer. Furthermore, the inclusion of an elastomeric material can provide a smooth contoured fit to a wearer, thereby improving appearance and self-confidence for the wearer.

The elastomeric material and the substrate layers form elastomeric composites, which provide a distributed consistent elastic modulus through the absorbent article, including the leg and waist openings and/or the front and rear sections, depending on the specific construction. By constructing the absorbent article in such a manner, consistent securement to the wearer at each of the openings is ensured. These composite layers, in addition to the placement of the absorbent core between the two layers, are mainly responsible for providing the smooth contoured fit of the presently disclosed absorbent articles.

The elastomeric material can include both breathable and substantially fluid-impervious regions, with the fluid-impervious regions preferably located in areas in which leakage may occur, for example, around the leg and at least a part of the waist openings of the absorbent article. In one aspect, breathable regions can extend from the waist opening along the side edges of the absorbent article to the fluid-impervious regions located along the legs openings. In this way, the absorbent article provides the wearer with breathable areas to aid in the wearer's comfort, while also providing leakage protection in key areas. In one embodiment, the elastomeric material is a stretch adhesive, wherein the breathable regions are provided by spraying the stretch adhesive on the substrate layers and the fluid-impervious regions are provided by slot-coating the stretch adhesive on the substrate layers. However, it should be noted that, in some embodiments, the stretch adhesive may be applied via a slot coating method only, or a spray method only, or a combination of slot coating and spraying methods in different portions or zones of the article.

In an example, a stretchable adhesive can include an extruded adhesive that can be dispensed in machine or cross directions (MD or CD) along an absorbent article assembly line. The stretchable adhesive can impart a stretchable characteristic to an assembly, for example, after the adhesive is cured. That is, whereas some adhesive can dry or cure and become stiff or impart some rigidity to its substrate, a stretchable adhesive in contrast can dry or cure and remain pliable, flexible, and can have an elastic or stretchable characteristic. In an example, a stretchable adhesive can be used in place of elastic strands or stretchable sections (e.g. comprising a stretchable film), or a stretchable adhesive can be applied to augment an extension or contraction characteristic of another stretchable material such as an elastic strand or stretch film Furthermore, an advantage to using stretch adhesive lies in the ability to manufacture the absorbent article in the machine direction (i.e. from the edge of the front section to the edge of the back section) while providing stretch in the desired direction—the direction that is orthogonal to the machine direction (CD Stretch). By manufacturing the absorbent article in the machine direction, the stretch adhesive can be applied to the substrate layers in zones which run the length of the absorbent article from the top edge to the bottom edges, and which allow for the provision of breathable and fluid-impervious regions at desired locations using a fully automated manufacturing process.

Accordingly, the absorbent articles of the present disclosure provide numerous advantages over currently available absorbent products, particularly in the realm of disposable undergarments. In particular, the absorbent articles provide for improved performance against leakage. Specifically, because the absorbent article lies flat against a wearer's body, such as to provide a smooth contoured fit to the body and one continuous material is in contact with the wearer's body, any gaps caused by overlapping materials, such as the absorbent core overlapping the composite material of the product chassis, non-conformance contact with the body, and lack of flexibility, are reduced or eliminated. By reducing or eliminating gaps between the garment and the body, the absorbent articles of the present disclosure provide improved leak resistance over prior art constructions. Additionally, the smooth interface of the article with the body provides improved comfort for the wearer. For example, because the absorbent core insert is located between the elastic composite layers, any corners, seams, borders, etc. caused from attachment of the absorbent core insert to the inside of the product chassis that can irritate or cause discomfort to the wearer are eliminated. Furthermore, by placing the absorbent core insert within the two elastomeric composites such that only the smooth surface of the substrate layer is visible, the aesthetics of the product are improved. Furthermore, such a design more closely aligns the disposable absorbent article to nonabsorbent undergarment worn by those individuals not suffering from incontinence or other situations that require the use of an absorbent article, which is a desirable feature with consumers.

Additionally, the elastomeric composite provides consistent pressure and smooth contact against the leg and waist during wear when it is stretched, such that improved performance against leakage is obtained. The composite forms a gasket around the entire perimeter of the openings which are in direct contact with the skin. Traditional elastic composites, used in absorbent products today, are first stretched and then bonded or adhered to non-stretchable materials. This causes the non-stretchable material to retract and create small corrugations. Fluid can leak through the small gaps within these corrugations. Because the elastic composites of the present invention are comprised entirely of stretchable materials, which do not retract and create corrugations, improved skin contact and reduced fluid leakage is experienced.

BRIEF DESCRIPTION OF THE DRAWINGS

Features and advantages of the claimed subject matter will be apparent from the following detailed description of embodiments consistent therewith, which description should be considered with reference to the accompanying drawings.

FIGS. 33A and B are top plan views of an absorbent article in the laid open configuration (A) and the folded configuration (B) in accordance with one embodiment, FIGS. 34A and B are top plan views of an absorbent article in accordance with the embodiment of FIG. 33, having an elastomeric material sprayed on a substrate. FIG. 34A shows the absorbent article in the laid open configuration, while FIG. 34B shows the absorbent article in the folded configuration.

FIGS. 35A and B are top plan view of the absorbent article of FIG. 34, wherein a polymer film and absorbent core has been added. FIG. 35A shows the absorbent article in the laid open configuration, while FIG. 35B shows the absorbent article in the folded configuration.

FIGS. 42A-D depicts exemplary shapes for the leg openings/slits that can be cut into the absorbent articles of the present disclosure.

Figure 1:
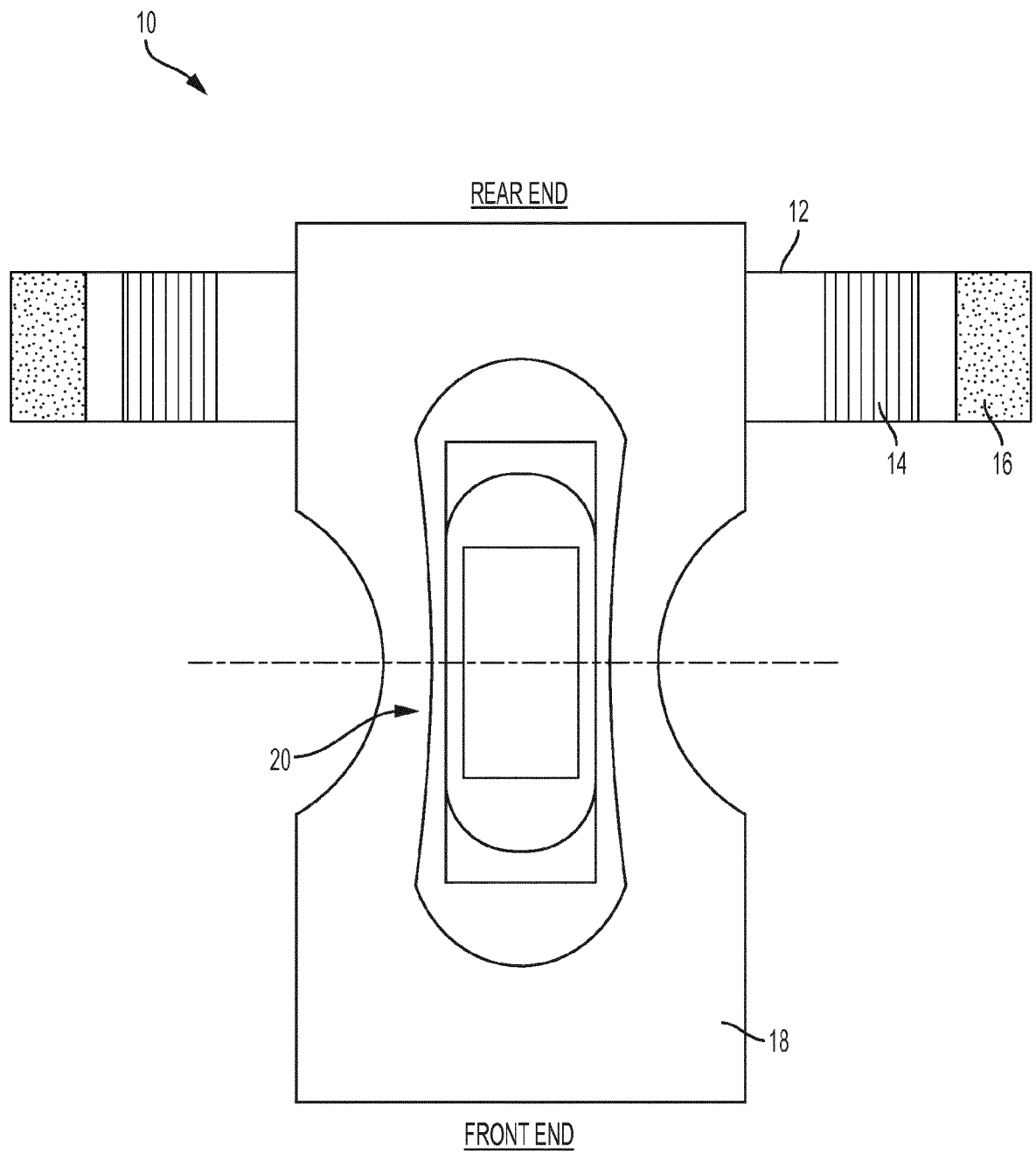
FIG. 1 is a top plan view of an exemplary disposable absorbent undergarment consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present invention provides disposable absorbent articles, such as disposable undergarment, diapers, other garments, and wound care dressings, having an elastomeric material and an absorbent core disposed between two substrate layers. In addition, the absorbent core system can be applied on top of the two substrate layers that contain an elastomeric material disposed between them. The inclusion of an stretch adhesive in the construction of the article in various portions of the article (e.g., fastening tabs, front and/or rear sections, entire article, etc.) results in improved securement of the article to a wearer for reducing the risk of leakage and further improving comfort for the wearer. Furthermore, the inclusion of a stretch adhesive can provide a smooth contoured fit to a wearer, thereby improving appearance and self-confidence for the wearer.

The elastomeric material and the substrate layers form elastomeric composites, which provide a distributed consistent elastic modulus through the absorbent article, including the leg and waist openings and/or the front and rear sections, depending on the specific construction. By constructing the absorbent article in such a manner, consistent securement to the wearer at each of the openings is ensured. These composite layers, in addition to the placement of the absorbent core between the two layers, are mainly responsible for providing the smooth contoured fit of the presently disclosed absorbent articles.

The elastomeric material can include both breathable and substantially fluid-impervious regions, with the fluid-impervious regions preferably located in areas in which leakage may occur, for example, around the leg and at least a part of the waist openings of the absorbent article. In one aspect, breathable regions can extend from the waist opening along the side edges of the absorbent article to the fluid-impervious regions located along the legs openings. In this way, the absorbent article provides the wearer with breathable areas to aid in the wearer's comfort, while also providing leakage protection in key areas. In one embodiment, the elastomeric material is a stretch adhesive, wherein the breathable regions are provided by spraying the stretch adhesive on the substrate layers and the fluid-impervious regions are provided by slot-coating the stretch adhesive on the substrate layers. However, it should be noted that, in some embodiments, the stretch adhesive may be applied via a slot coating method only, or a spray method only, or a combination of slot coating and spraying methods in different portions or zones of the article.

In an example, a stretchable adhesive can include an extruded adhesive that can be dispensed in machine or cross directions (MD or CD) along an absorbent article assembly line. The stretchable adhesive can impart a stretchable characteristic to an assembly, for example, after the adhesive is cured. That is, whereas some adhesive can dry or cure and become stiff or impart some rigidity to its substrate, a stretchable adhesive in contrast can dry or cure and remain pliable, flexible, and can have an elastic or stretchable characteristic. In an example, a stretchable adhesive can be used in place of elastic strands or stretchable sections (e.g., comprising a stretchable film), or a stretchable adhesive can be applied to augment an extension or contraction characteristic of another stretchable material such as an elastic strand or stretch film Furthermore, an advantage to using stretch adhesive lies in the ability to manufacture the absorbent article in the machine direction (i.e. from the edge of the front section to the edge of the back section) while providing stretch in the desired direction—the direction that is orthogonal to the machine direction. By manufacturing the absorbent article in the machine direction, the stretch adhesive can be applied to the substrate layers in zones which run the length of the absorbent article from the top edge to the bottom edges, and which allow for the provision of breathable and fluid-impervious regions at desired locations using a fully automated manufacturing process.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to absorb and/or retain bodily exudates.

"Absorbent component" as used herein refers to a structural constituent of an absorbent structure, e.g., a piece of an absorbent core, such as one of multiple pieces in a multi-piece absorbent core.

"Absorbent element" as used herein refers to a part of a functional constituent of an absorbent structure, e.g., a liquid acquisition layer, a liquid distribution layer, or a liquid storage layer formed of a material or materials having particular liquid handling characteristics suitable for the specific function.

"Absorbent insert" as used herein refers to a device adapted for insertion into an absorbent article and to serve as an absorbent structure when so inserted.

"Absorbent layer" as used herein refers to a term referring to a discrete, identifiable sheet-like or web-like element of an absorbent structure which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 tines and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g. bond area's) or unintentional (e.g. manufacturing artefacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Acquisition layer", "acquisition region", "acquisition surface" or "acquisition material" and the like as used herein refer to a layer having a faster liquid uptake capability.

"Absorbency" is the ability of a material to take up fluids by various means including capillary, osmotic, solvent, chemical or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure or vacuum; a web of fibers produced by airlaying is herein referred to an "airlaid"; an airlaid web bonded by one or more techniques to provide fabric integrity is herein referred to an "airlaid nonwoven".

"Apparent density" "density" as used herein refers to the basis weight of the sample divided by the caliper with appropriate unit conversions incorporated therein. Apparent density used herein has the unit g/cm3.

"Attach", "attached" and "attachment" as used herein are synonymous with their counterparts of the terms "fasten", "affix", "secure", "glue", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to undergarment intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, g/m2 or gsm.

"Bodily exudates", "body exudates", "bodily fluids", "body fluids", "bodily discharges", "body discharges", "liquids" and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc.; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc.), altering the chemical structure of the fibers themselves (e.g. by cross-linking polymer chains, etc.) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or contain, "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garments, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place, the setting may occur by removing solvent or by cross-linking so as to make them insoluble.

"Diaper", "conventional diaper", "diaper-like", "diaper-like garment" and the like as used herein are used interchangeably and refer to disposable absorbent articles, which typically include a front waist portion and a back waist portion which may be releasably connected about the hips of the wearer during use by conventional fasteners such as adhesive tape fasteners or hook and loop type fasteners. In use, the article is positioned between the legs of the wearer and the fasteners are releasably attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Distribution layer", "distribution region", "distribution surface" or "distribution material" and the like as used herein are used interchangeably and refer to a layer having a larger capacity in wicking, dispersing and distributing liquids.

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of an adhesive joint determined in dry state conditions, immediately after drying under specified conditions or after a period of conditioning in the standard laboratory atmosphere.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width;

"Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" as used herein refers to wood pulp specially prepared to be drylaid.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"Highloft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and faces the wearer facing layer; conversely, the term "lower" refers to the layer of the absorbent article which is nearest to and faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (ID)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibers by entangling then. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "pre-fastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Resin" as used herein refers to a solid or semisolid polymeric material.

"Substantially cellulose free" as used herein refers to an absorbent article, structure or core, that contains less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "Woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The recitation of numerical ranges by endpoints includes all numbers and fractions subsumed within that range, as well as the recited endpoints.

The following description with reference to FIGS. 1-4 refers to an exemplary absorbent article, generally in the form of a disposable absorbent undergarment and is provided for a basic understanding of an article consistent with the present disclosure.

Figure 2:
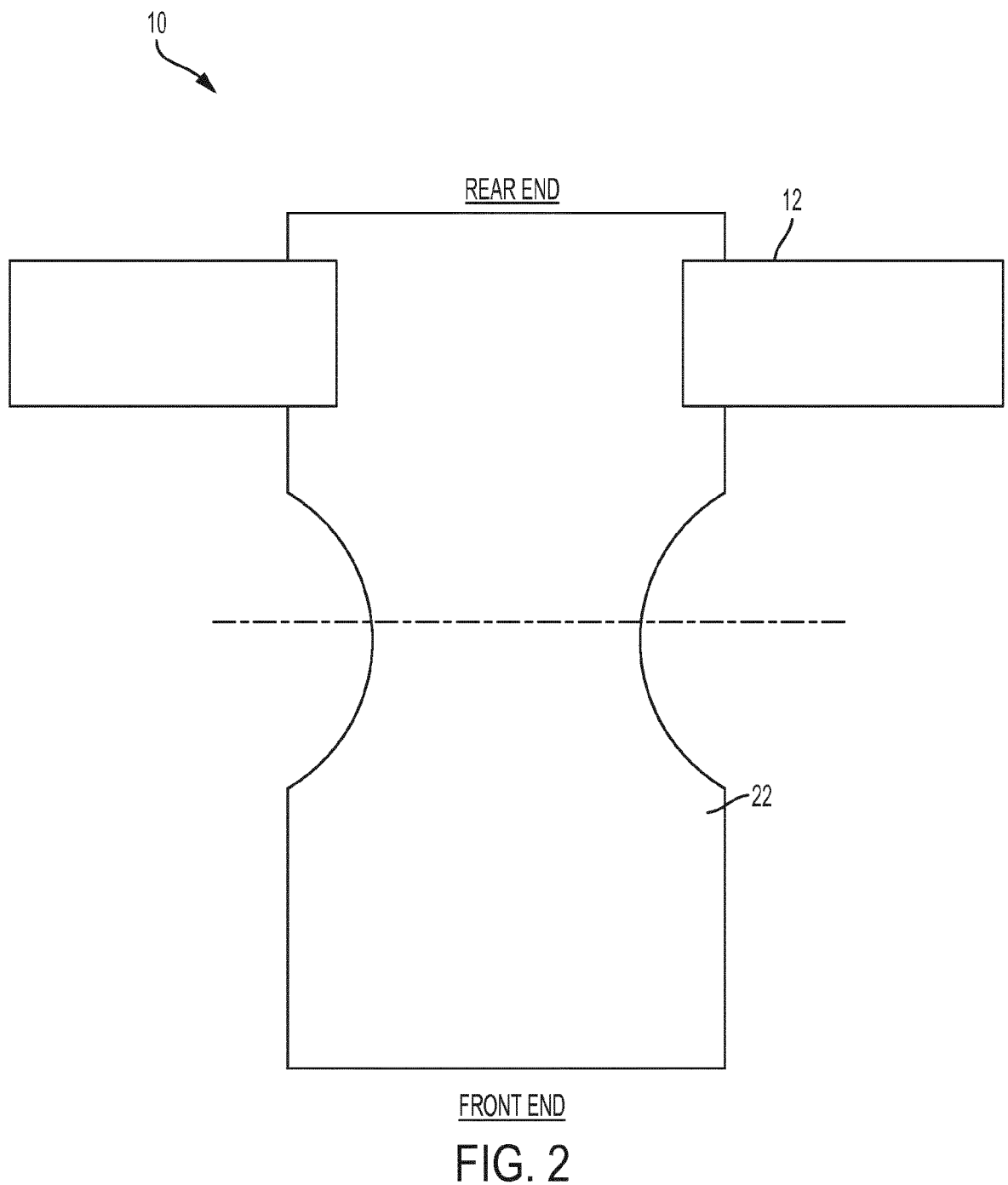
FIG. 2 is a bottom plan views of the absorbent undergarment of FIG. 1.

FIG. 1 is a top plan view of a disposable absorbent undergarment 10 consistent with the present disclosure and FIG. 2 is a bottom plan view of the absorbent undergarment 10. The undergarment 10 is generally in the form of a diaper or brief. While the following description with respect to FIGS. 1-31 focus on briefs or diapers, it should be clear that the subject invention can be used for any type of absorbent article or garment to be worn by a person for bodily fluids and/or excrement.

The undergarment 10 is shown in FIG. 1 from the interior side of the product that is designed to be in direct contact with the wearer, as opposed to the exterior side of the product, as shown in FIG. 2. The undergarment 10 generally includes a front section and a rear section, wherein the front section is generally designed to be fitted against the front, or anterior portion, of a wearer, while the rear section is generally designed to be fitted against the rear, or posterior portion, of the wearer, such that front and rear sections generally oppose one another once fitted to the wearer.

The undergarment 10 can have various shapes and sizes, and is generally configured to be worn between an individual's legs and secured about the waist. In order to secure the undergarment onto a wearer's body and stay in place, the undergarment includes a fastening system. In particular, the undergarment 10 includes tabs 12 extending from the rear section of the undergarment 10. As shown, the undergarment 10 may include two tabs 12 extending from opposite sides of the rear section. Each tab 12 may include and extensible and retractable portion 14 and a fastener member 16. As will be described in greater detail herein, the fastener member 16 is configured to engage and attach to an exterior surface of the front section of the undergarment 10, thereby coupling the front and rear sections to one another and securing the undergarment onto a wearer's body.

The extensible/retractable portion 14 may generally include a stretchable material having elastic properties allowing the fastener member 16, which is generally positioned on a distal end of the tab 12, to be pulled to a desired position for attachment to the front section Once the fastener member 16 is in place and engaged with the exterior surface of the front section, the extensible/retractable portion 14 provides a relatively constant pulling force against the fastener member 16 and the corresponding portion of the front section to which the fastener member 16 is attached, thereby further drawing the front and rear sections of the undergarment 10 towards one another to provide a secure fit against the wearer.

Figure 3:
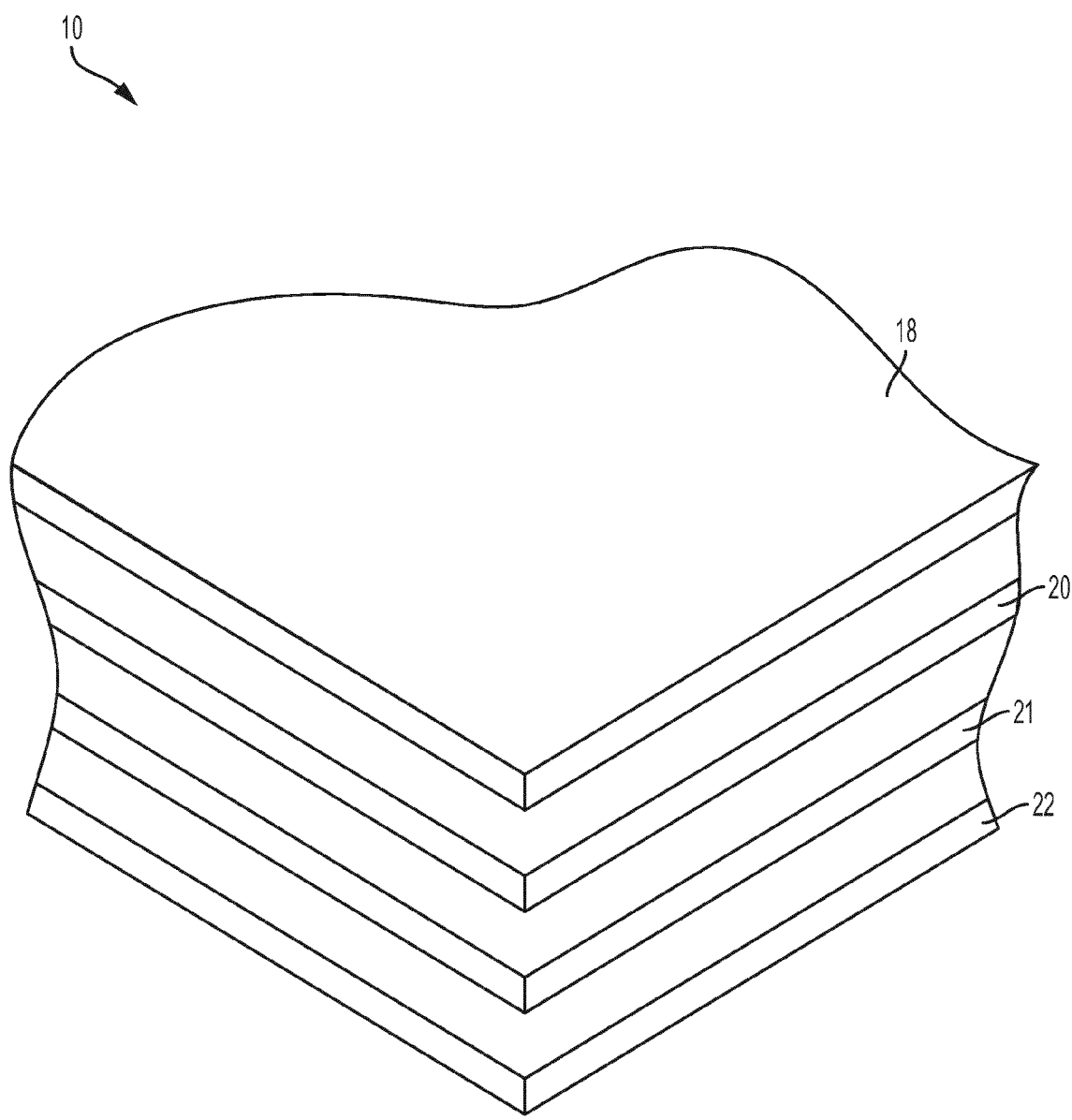
FIG. 3 is an enlarged perspective view of a portion of the absorbent undergarment of FIG. 1 illustrating multiple layers separated from one another.

FIG. 3 is an enlarged perspective view of a portion of the absorbent undergarment 10 illustrating multiple layers separated from one another. The undergarment 10 may be constructed from multiple layers, which may include at least a first layer 18, a second layer 20, and a third layer 22. The first layer 18, also referred to herein as the "top sheet 18", is generally configured to contact a subject's skin and allows fluid from the subject (i.e., human, animal, etc.) to flow through it, at least in a direction away from the subject's skin. The second layer 20, also referred to herein as the "absorbent core 20", includes a fluid absorption and retention portion having at least one absorbent material for absorbing a fluid passing through the top sheet 18. The undergarment 10 further includes a third layer 22 coupled to the first and second layers 18, 20. The third layer 22, also referred to herein as the "back sheet 22", generally serves as the outermost layer of the undergarment 10. The back sheet 22 is generally formed from a nonwoven material, to provide a more undergarment-like appearance and feel, and as well as a more cost-effective and comfortable alternative to conventional disposable undergarment designs. The fibers in the nonwoven may include, for example, polypropylene, polyethylene, polyester, bi-component (polypropylene & polyethylene or polyester & polyethylene), cotton, cotton blend, viscose, rayon, etc. or a combination of different fibers. The nonwoven web may include, but is not limited to, Spunbond Polypropylene (SBPP), Spunbond-Meltblown-Spunbond (SMS), Thermal-bonded Carded Web, Spunlace, Laminate, or combinations thereof.

The fastener member 16 may include a plurality of micro-hooks or barbs which have a hook design similar to the hook portion of a hook-and-loop fastener. The exterior surface of the nonwoven material of the back sheet 22 includes exposed fibers, wherein, upon contact between the fastener member 16 and the exterior surface of the back sheet 22, the micro-hooks are configured to grab and hold onto the fibers of the nonwoven material, thereby fastening the tabs 12 to the back sheet 22.

In the embodiments described herein, the undergarment 10 includes at least an optional fourth layer 21, also referred to herein as the "fluid impervious barrier 21", in which the absorbent 20 is positioned between the top sheet 18 and the fluid impervious barrier 21. The fluid impervious barrier 21 may generally include a fluid impervious material, such as a poly film, and is breathable, achieved by allowing water vapor and/or air to pass through the barrier 130 while preventing the passage of liquid. It should be noted, however, that in some embodiments, the fluid impervious barrier 21 is not breathable.

Figure 4:
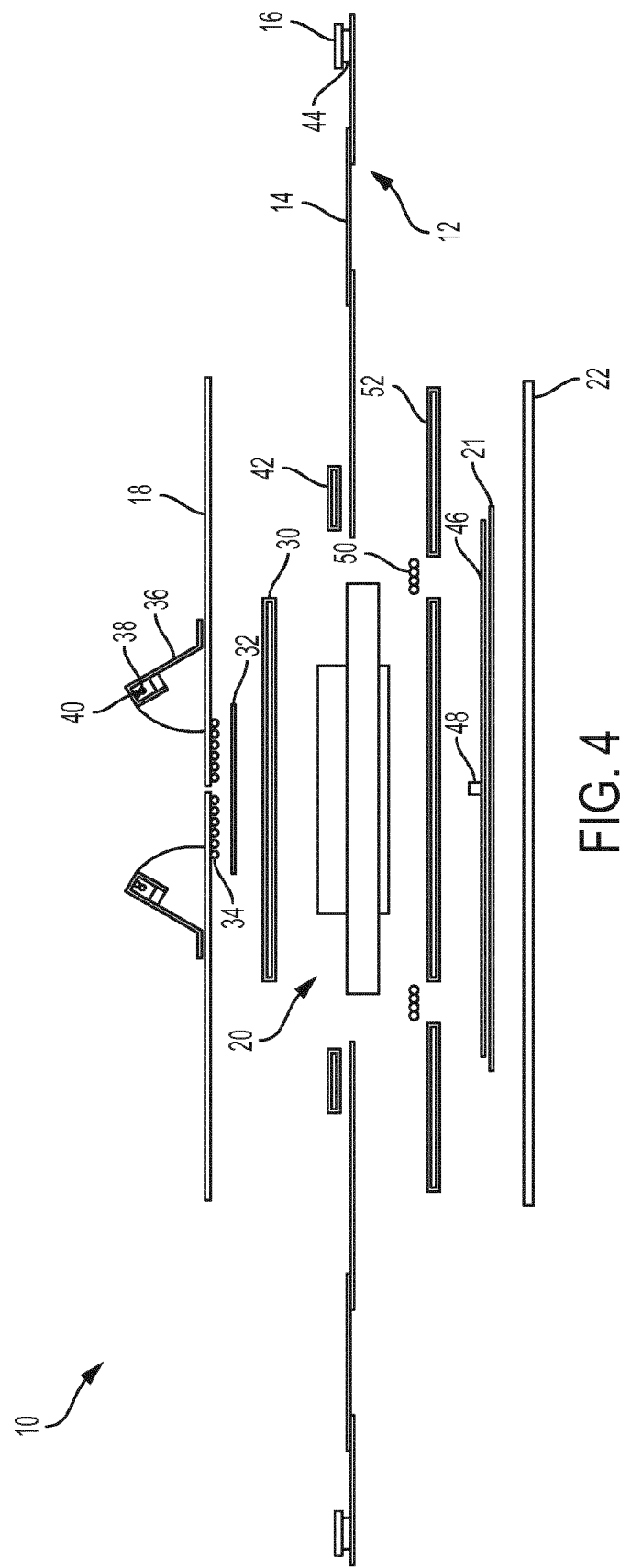
FIG. 4 is an exploded cross-sectional view of the absorbent undergarment of FIG. 1 illustrating the multiple layers and absorbent core.

FIG. 4 is an exploded cross-sectional view of the absorbent undergarment 10 illustrating the multiple layers, including the top sheet 18, absorbent core 20, fluid impervious barrier layer 21, and corrugated nonwoven back sheet 22.

The top sheet 18 may be joined to the absorbent core 20 via an core adhesive 30 and/or an acquisition/distribution layer 32 (ADL), such as with a corresponding ADL adhesive 34, which can be positioned between the top sheet 18 and absorbent core 20. In some embodiments, the top sheet 18 includes at least one of a nonwoven material, a hydrophilic or partially hydrophilic material, a nonwoven material with a zone-coated surfactant, and a nonwoven and apertured film. One material that can be used for the top sheet is an SBPP (Spunbond Polypropylene) hydrophilic nonwoven, commercially available from Avgol, located in Tel Aviv, Israel. The surfactant on the top sheet 18 can be zone-coated, for example, which may provide a barrier along particular portions (e.g., the sides) of the undergarment 10 to reduce fluid leakage. Optionally, the undergarment 10 may include a stand-up leg elastic assembly 36, including a nonwoven material, one or more elastic components 38, and an adhesive 40.

The undergarment 10 may further include tab attachment means 42 for coupling the tabs 12 to the undergarment 10. The attachment means 42 may include, but is not limited to, an adhesive, an ultrasonic bond, a beat seal, a breakable fastener, or other means of securely attaching non-woven, laminate, polymeric, or other materials. Furthermore, the fastener 16 (e.g., micro-hooks) may be fastened to the distal end of the tab 12 via an adhesive 44 or other fastening means.

The absorbent core 20 may generally include an absorbent material, a nonabsorbent material, and a combination thereof. For example, the absorbent core 20 may include one or more of: "pulp only" core; "pulp & SAP" core; "pulp & SAP & tissue" core; "pulp & SAP nonwoven" core, "airlaid composite" core; "airlaid composite" core with cotton fibers: "rayon viscose" core; "rayon viscose & pulp" core; "rayon viscose & SAP" core; "rayon viscose & pulp & SAP" core; "rayon viscose & pulp & SAP & tissue" core; "tissue" core; "tissue & SAP" core; "creped tissue or paper towel" core; "creped tissue with SAP" core; "pulp & curly fiber" core; "pulp & curly fiber & SAP" core; SAP and nonwoven composite core (Pulpless); and "pulp & curly fiber & SAP & tissue" core.

The absorbent core 20 may be comprised of multiple layers or structures. For example, as shown, the absorbent core may include at least three absorbent core structures. Optionally, more than three core structures can be used. Optionally, one or more core structures can be used, and the one or more core structures can have a variable thickness, or can have non-homogeneously-distributed constituent parts. For example, a unitary but non-homogenous core structure can have a portion that comprises fluff without SAP and another portion that comprises fluff with SAP, and optionally another portion that comprises fluff with a different proportion of SAP relative to fluff. The multicore design of the absorbent core 20 is discussed in co-pending international application titled "Multi-Core Absorbent Article", having application no. PCT/US2016/012710, and filed Jan. 8, 2016, the content of which is incorporated by reference herein in its entirety.

The nonwoven back sheet 22 may generally extend over all or at least a portion of the undergarment 10, wherein the back sheet 22 provides a garment-facing surface of the undergarment when the undergarment is worn under clothing. The fluid impervious barrier layer 21 may be breathable in some embodiments, while in other embodiments, the barrier 21 is not breathable. Additionally, the barrier 21 can be cloth-like or non-cloth-like. For example, a cloth-like material for the barrier 21 a Poly Laminate, from Berry Plastics located in Chippewa Falls, WI. One poly film that can be used for the barrier 21 is a polyethylene/polypropylene film blend available from Berry Plastics located in Chippewa Falls, WI. One breathable poly film that can be used for the barrier 21 is a micro-porous film available from Clopay located in Mason, Ohio. One breathable cloth-like material for the barrier 130 that can be used is Poly Laminate available from Galaxy, China.

The undergarment may optionally include printing 46 over all or a portion of the surface of one or both of the nonwoven back sheet 22 or the polymeric barrier layer 21. The printing can include graphic designs, size indicia, or other markings for aesthetic or functional purposes.

The undergarment may optionally include a wetness indicator 48, such as can be positioned substantially centrally along a portion of a length of the undergarment. Leg elastics 50 and leg elastic adhesives 52 may be layered between any two or more of the nonwoven back sheet 22, the polymeric barrier layer 21, and respective left and right side tabs 12. The leg elastics 50 may extend substantially parallel to a longitudinal axis of the undergarment 10 at or near leg cutouts.

Figure 5:
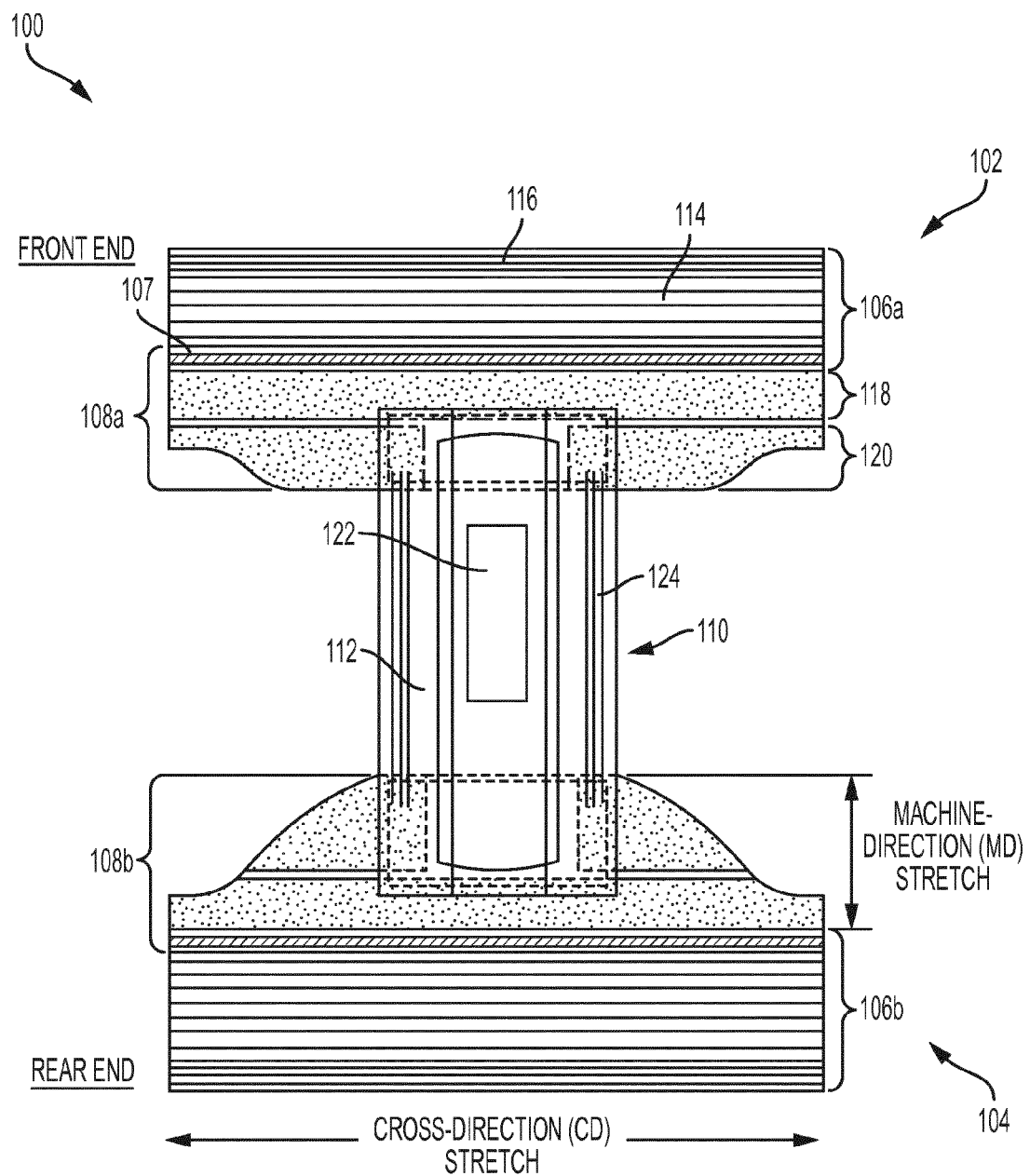
FIG. 5 is a top plan view of a disposable absorbent undergarment having machine direction (MD) stretchable front and rear sections as a result of a stretch adhesive composite provided on front and rear sections, the stretch adhesive composite including a slot coated stretch adhesive.
Figure 6:
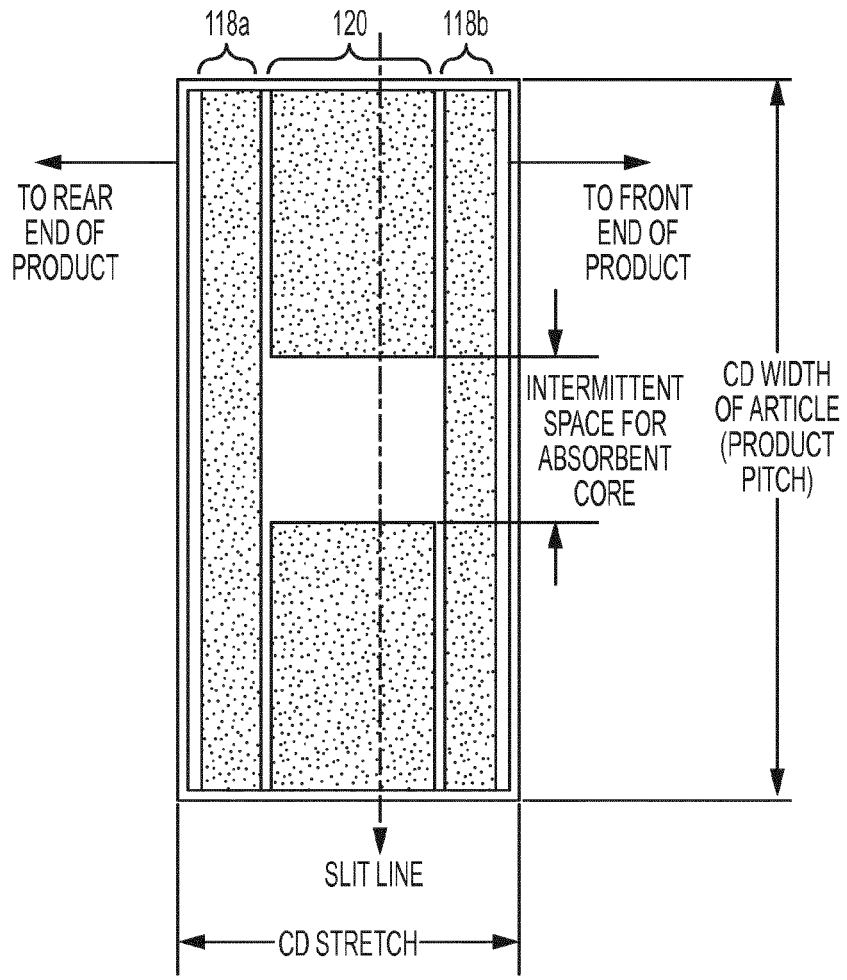
FIG. 6 is top view of the disposable absorbent undergarment of FIG. 5 during manufacturing and FIG. 7 is a side view of the disposable absorbent undergarment of FIG. 6.
Figure 7:

FIG. 5 is a top plan view of a disposable absorbent undergarment 100 having machine direction (MD) stretchable front and rear sections as a result of a stretch adhesive composite provided on front and rear sections, the stretch adhesive composite including a slot coated stretch adhesive. In the embodiment of FIG. 5, a dual slot coating of stretchable adhesive is provided on the undergarment, thereby forming a stretch adhesive composite which includes the stretch adhesive provided between two layers, as will be described in greater detail herein. FIG. 6 is top view of a section of the disposable absorbent undergarment of FIG. 5 during manufacturing and FIG. 7 is a side view a section of the disposable absorbent undergarment of FIG. 6.

As shown in FIG. 5, the undergarment 100 may include a body including a first body section 102 forming a front section of the undergarment 100 and a second body section 104 forming a rear section of the garment 100. As generally understood, the first body section (hereinafter referred to as "front section 102") is configured to be fitted against a front, or anterior, portion of a wearer's body and the second body section (hereinafter referred to as "rear section 104") is configured to be fitted against a rear, or superior, portion of the wearer's body. It should be noted that, in some embodiments, the front and rear body sections 102, 104 are unitary in construction (i.e., formed as a single unit). However, in some embodiments, the front and rear body sections 102, 104 may be separate from one another.

The undergarment 100 further includes a crotch section positioned between the front and rear sections 102, 104 and coupled to each. The crotch section includes an insert 110, which nay include at least an absorbent core 112 including a liquid-absorbing material. In the embodiments described herein, at least one of the front section 102, the rear section 104, and the crotch section, including the insert 110, includes stretchable portions for providing improved securement of the article to a wearer for reducing the risk of leakage and further improving comfort for the wearer, as well as a more smooth contoured fit to a wearer, thereby improving appearance and self-confidence for the wearer.

For example, as shown in FIG. 5, the front section 102 and rear section 104 may include waist/belly portions 106a, 106b, respectively. The waist/belly portions 106a, 106b may include elastic strands arranged in such as manner so as to provide cross directional (CD) stretching along the belly position 114 and waist position 116 of the section. The front section 102 and rear section 104 further include elastomeric composite portions 108a, 108b, respectively. The elastomeric composite portions 108a, 108b each include an electromeric material configured to stretch in a direction transverse to the direction in which the elastomeric material is applied to form the elastomeric composite, thereby allowing a portion of at least one of the front section 102 and the rear section 104 to extend upon application of a pulling force thereto. In some embodiments, the crotch section including the insert 110, may include an elastomeric composite, and thus may similar stretching characteristics. The insert 110 may include, for example, one or more absorbent cores 112, an acquisition layer 122, as well as crotch elastics 124, stand-up leg gathers, and the like.

Upon application of the elastomeric material in a cross direction (CD), the elastomeric composite is configured to stretch in a machine direction. Similarly, upon application of the elastomeric material in the machine direction (MD), the elastomeric composite is configured to stretch in the cross direction (CD). In embodiments described herein, the elastomeric material includes a stretch adhesive providing such stretching properties, such as Conforma 9534-62-1 available from H. B. Fuller Company in Vadnais Heights, Minnesota. As shown, each of the elastomeric composite portions 108a, 108b include slot coated stretch adhesive portions 118 and 120 applied in a cross direction and positioned between two substrate layers (Spunlace nonwoven, for example). Accordingly, the elastomeric composite portions 108a, 108b of the front and rear sections 102, 104 are configured to stretch in the machine direction. The product can be folded (e.g., in half) and ultrasonically bonded at the side edges to provide a disposable pull-up undergarment.

The article can be manufactured according to one or more steps. For example, in step 1, the stretch adhesive is applied in three separate slot coat applications onto a Spunlace nonwoven (NW) web. One slot coater (middle section of the web) applies the stretch adhesive in a continuous or intermittent pattern 120 on top of a Spunlace nonwoven web 128. An open or unglued area can be registered and aligned to be under the absorbent core, specifically the insert 110. Two other slot coaters apply the stretch adhesive in a continuous pattern (outside sections of the web 118a and 118b). In some embodiments, there can be a narrow gap between the slot coat patterns that separates the slot coat nozzles in the process. In another embodiment, another Spunlace nonwoven web 126 is applied directly on top of the stretch adhesive, which can have the same slit width as the first Spunlace nonwoven web. This creates a stretch adhesive composite, e.g., that can be ultrasonically bonded to the belly elastic panels in the front and back sections of the product (see ultrasonic bond seam 107 in FIG. 5).

In a second step (i.e., "Step 2"), the stretch adhesive composite of Step 1 can be slit or cut into two sections, for example as shown in FIG. 6. One section can be registered, aligned and adhered to the front section 102 of the undergarment. The other section can be registered, aligned and adhered to the back section 104 of the undergarment. In a third step (i.e., "Step 3"), the stretch adhesive composite of Steps 1 and 2 can be ultrasonically bonded to the front and back sections, as illustrated in FIG. 5.

In a fourth step (i.e., "Step 4"), an insert 110 (e.g., including one or more absorbent cores 112, acquisition layer 122, crotch elastics 124, stand-up leg gathers, etc.) can next be registered, aligned and adhered to the front and back sections 102, 104 of the undergarment 100. The insert 110 can be applied on top of the stretch adhesive composite sections at both the front and back sections 102, 104. The absorbent core 112 can be registered and aligned to be in an "open area" of the stretch adhesive composite. This concept can provide the following product attributes, among others: (1) the absorbent core can be able to stretch in the longitudinal direction or machine direction (MD) of the product at both the front and back ends which can allow the absorbent core to be brought "closer to the body" and can help reduce/eliminate gaps that may cause urine leakage; and (2) the absorbent core can be surrounded (e.g., substantially completely) by elastic in close proximity, except for a small gap between slot coat patterns (see e.g., FIG. 5 showing MD stretch absorbent core in undergarment). The crotch elastics 124 (e.g., of the insert 110) can intersect the stretch adhesive sections (e.g., on front and back sections) of the product, creating a "perimeter gasket" around the absorbent core. This "perimeter gasket" can help reduce urine leakage at both sides (left and right sides) and both ends (front and back ends) of the product. This can be beneficial for product used at night time, when the consumer may be lying on their back, front (belly) or either side during sleep. This is the time that the absorbent product becomes more vulnerable to urine leakage, e.g., due to gravity and pressure applied by the weight of the consumer.

In a fifth step (i.e., "Step 5"), the front and back sections can be cut (e.g., with rotary dies) in a specific pattern to enhance aesthetics and fit on the body. In a sixth step (i.e., "Step 6"), the product can be folded in half, with both the front and back sections aligned directly on top of each other, in which both sides (left and right sides) of the product can be ultrasonically sealed and then cut. The product can then be further folded, printed, or otherwise processed and packaged.

In one example, the stretch adhesive composite includes the stretch adhesive positioned between and coupled to at least two substrate layers, which may include, for example, a Spunlace nonwoven layer that comprises up to 100% polypropylene fibers. This is compatible to the Spunbond Polypropylene nonwoven, which it can be ultrasonically bonded to, in the product chassis. In one example, materials used in construction of the stretch adhesive composite include, but are not limited to, Spunlace nonwoven (e.g. made of up to 100% polypropylene fibers and can be approximately 25-30 gsm in basis weight). One suitable material is FIBRELLA Lite Spunlace nonwoven manufactured by Suominen Corporation in Helsinki, Finland.

As previously described, the stretch adhesive can include Comforma (material number 9534-62-1) by JIB. Fuller in Vadnais Heights, Minnesota). The approximate add-on level can be approximately 75 gsm. It should be noted that other stretch adhesives can be used.

Figure 8:
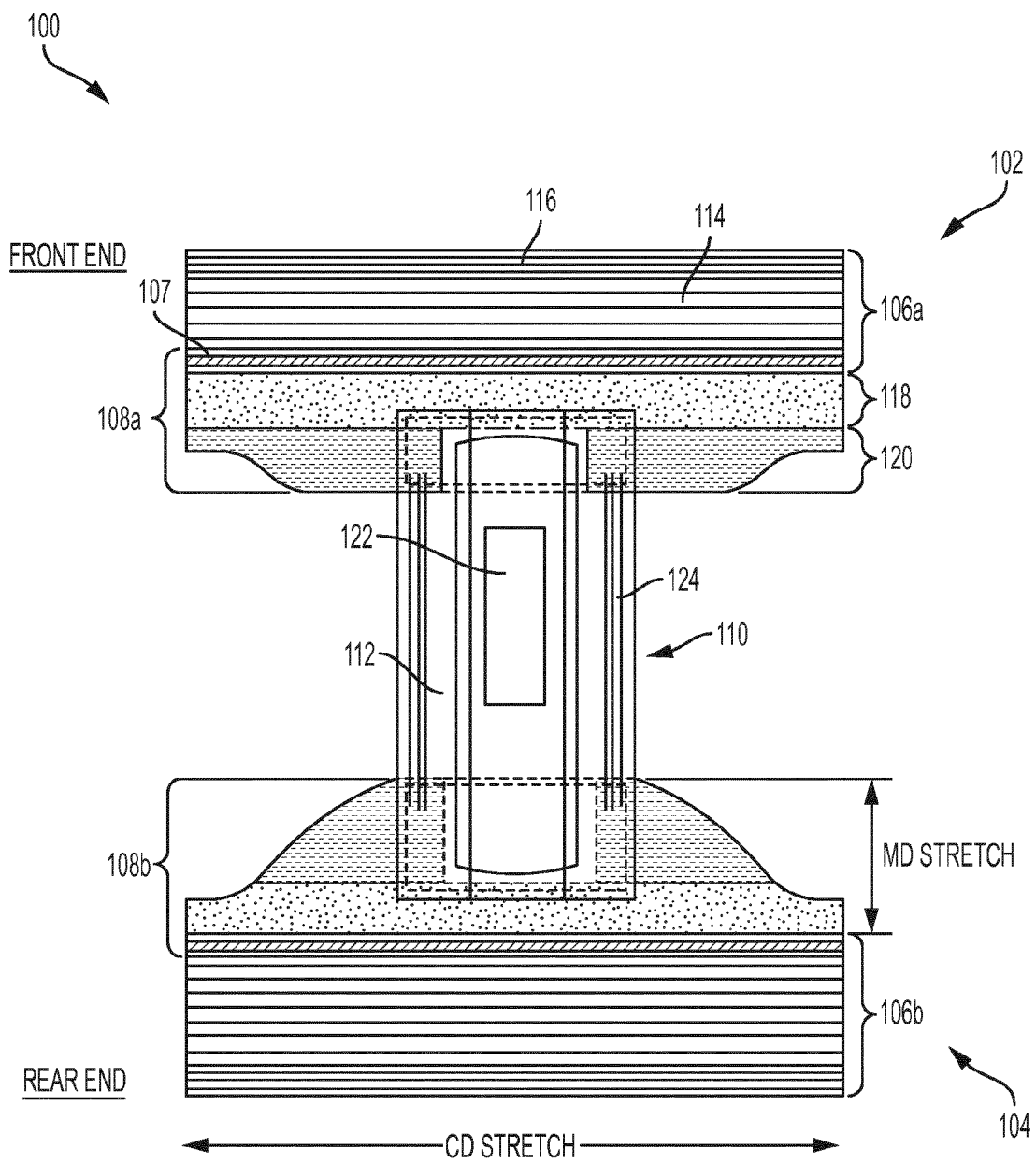
FIG. 8 is a top plan view of another embodiment of a disposable absorbent undergarment having machine direction (MD) stretchable front and rear sections as a result of a stretch adhesive composite provided on front and rear sections, the stretch adhesive composite including a combination of slot coated stretch adhesive and sprayed stretch adhesive.
Figure 9:
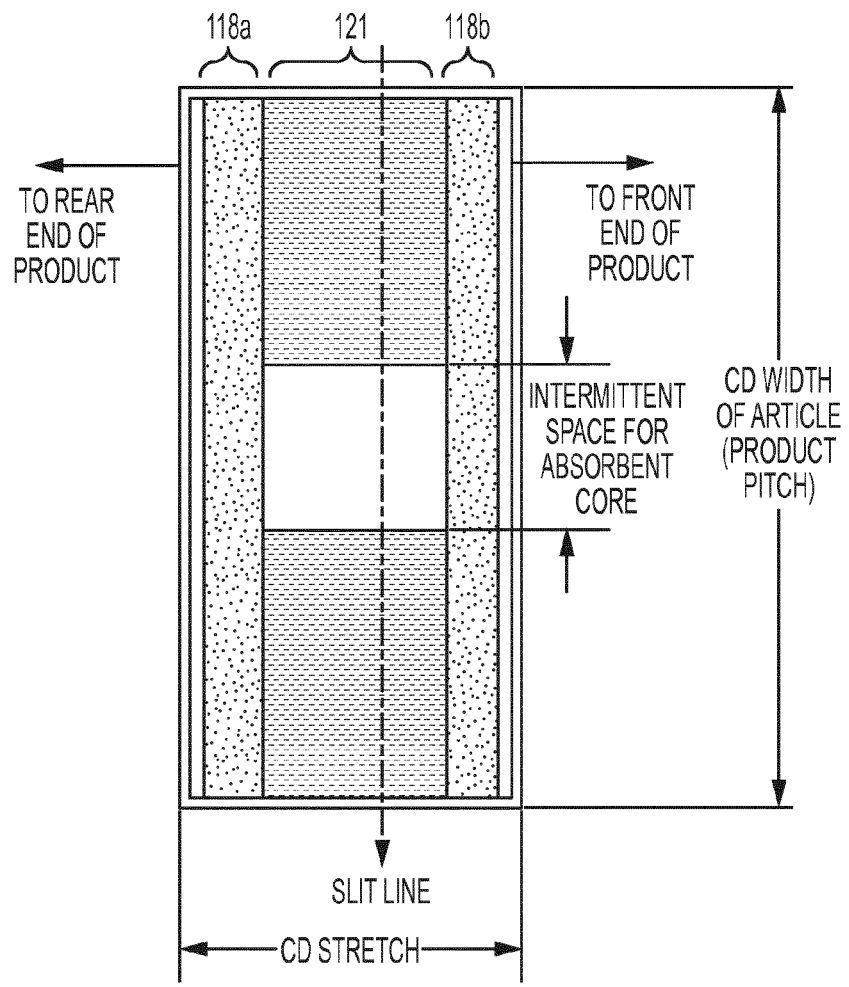
FIG. 9 is top view of the disposable absorbent undergarment of FIG. 8 during manufacturing and FIG. 10 is a side view of the disposable absorbent undergarment of FIG. 9.
Figure 10:
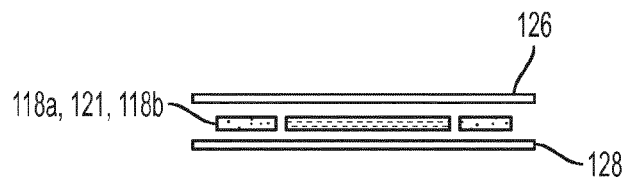

FIG. 8 is a top plan view of another embodiment of a disposable absorbent undergarment 100, similar to the undergarment 100 of FIG. 5, in which the front and rear sections 102, 104 including elastomeric composite portions 108a, 108b that are machine direction (MD) stretchable as a result of a stretch adhesive provided in a combination slot coat pattern and sprayed pattern. FIG. 9 is top view of a section of the disposable absorbent undergarment of FIG. 8 during manufacturing and FIG. 10 is a side view of a section of the disposable absorbent undergarment of FIG. 9. For example, as shown, the elastomeric composite portions 108a, 108b include both a slot coated stretch adhesive portion 118 and a sprayed stretch adhesive 121 applied in a cross direction and positioned between the two substrate layers (Spunlace nonwoven, for example). The combination slot coat and spray of stretch adhesive may further provide a breathable material layer. The embodiment illustrated in FIG. 8 may be similar to the embodiment illustrated in FIG. 5, except for a stretch adhesive composite that includes a two slot coat application (continuous pattern) and one spray application (intermittent pattern). It should be noted that the spray application can be a spiral or sporadic fiber pattern as well.

The steps involved in manufacturing the stretch adhesive composite and the undergarment of FIG. 8 may be similar to that described in the embodiment of FIG. 5, except for the following:

In Step 1, one spray adhesive application (e.g., in a middle section of the web) applies stretch adhesive in an intermittent pattern on top of a Spunlace nonwoven web. An open or unglued area can be registered and aligned to be under the absorbent core. Two slot coaters can apply stretch adhesive in a continuous pattern (e.g., corresponding to the outside sections of the web). In this example, there is optionally no narrow gap between the slot coat and spray adhesive applications. The spray adhesive application can be over-sprayed into the slot coat application area.

By way of example, differences between the embodiments of FIG. 5 and FIG. 8 can include, for example, a combination of slot coat and spray adhesive applications in the embodiment of FIG. 8 can eliminate any gap(s) in the stretch adhesive composite. This can help reduce any potential urine leakage through the gap(s) and eliminate any "weak" spots in the product chassis that may tear during high tension or stress. The addition of spray adhesive application in the embodiment of FIG. 8 can provide a more "breathable" material for the stretch adhesive composite. The spray adhesive can also provide stretch adhesive in a slot coat application at both ends (front and back) of the product. It is believed that the slot coat application can provide higher strength and more robust stretch characteristics vs. spray application. Thus, the embodiment of FIG. 8 can provide both "breathability" for the product along with "functional stretch" for the absorbent core.

Figure 11:
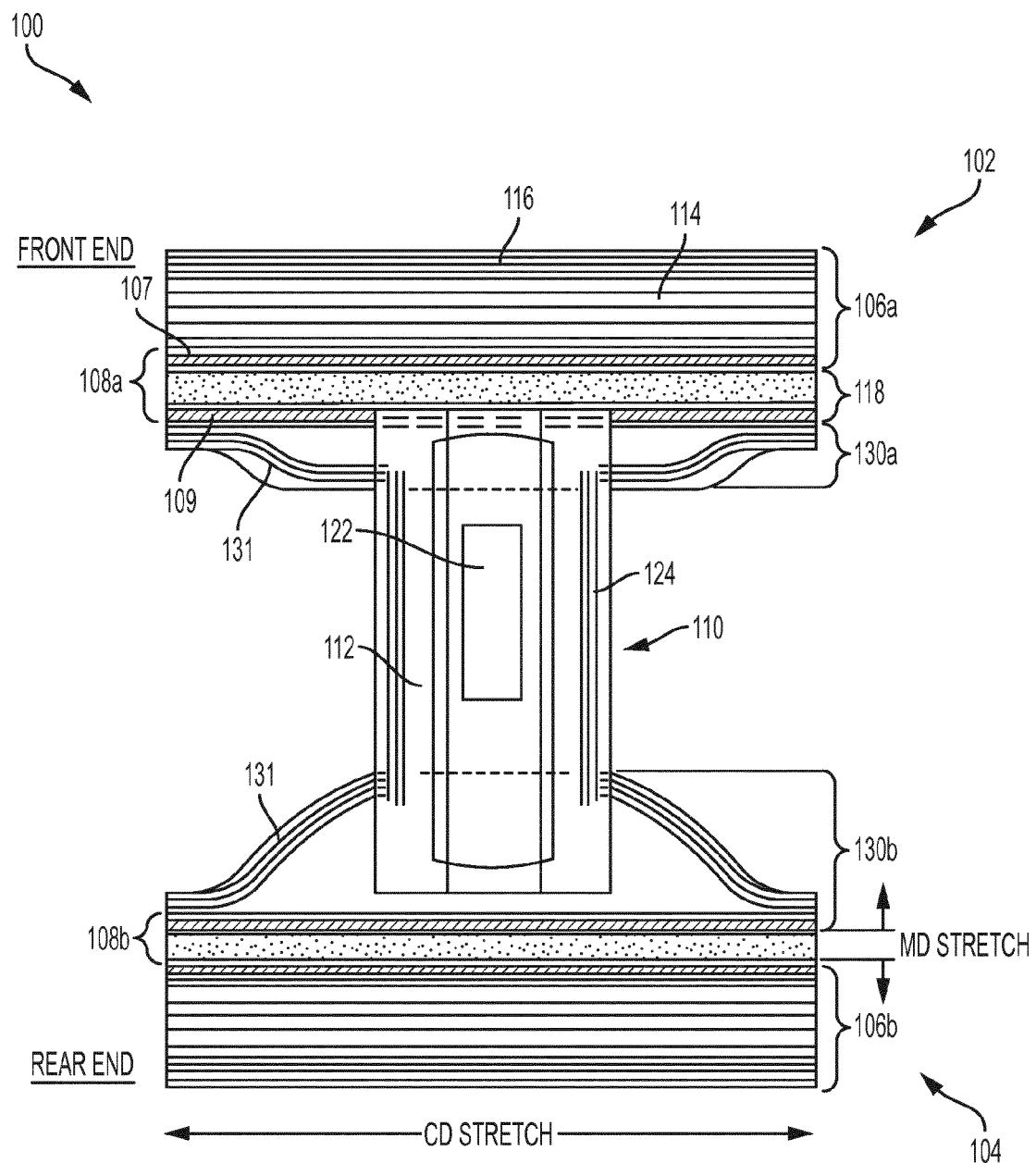
FIG. 11 is a top plan view of another embodiment of a disposable absorbent undergarment having machine direction (MD) stretchable front and rear sections and an MD stretchable insert as a result of as a result of a stretch adhesive composite provided on front and rear sections in combination of elastic bands provided in the insert.
Figure 12:
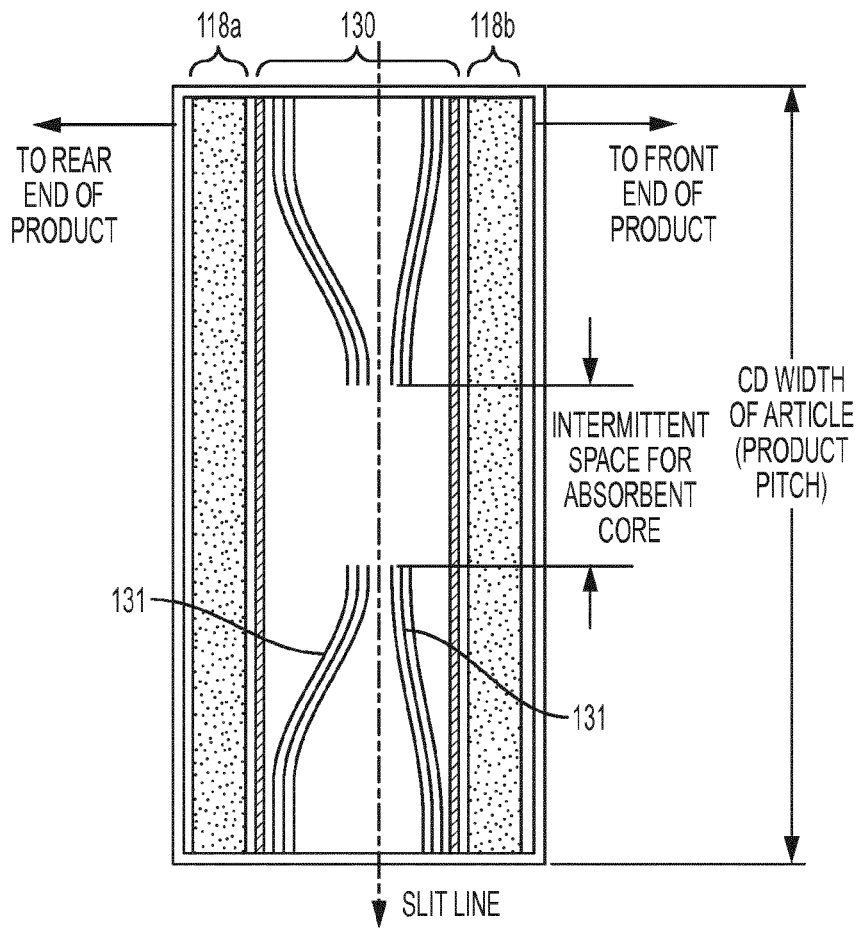
FIG. 12 is top view of the disposable absorbent undergarment of FIG. 11 during manufacturing and FIG. 13 is a side view of the disposable absorbent undergarment of FIG. 12.
Figure 13:
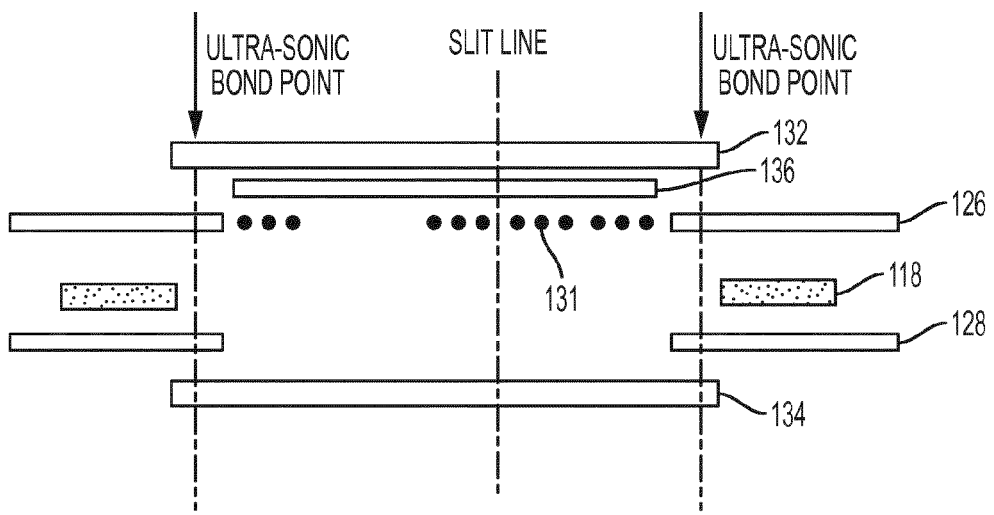

FIG. 11 is a top plan view of another embodiment of a disposable absorbent undergarment having machine direction (MD) stretchable front and rear sections and an MD stretchable insert 110 as a result of an elastomeric composite provided on front and rear sections 102, 104 in combination with elastic bands provided in the insert and in the leg regions. FIG. 12 is top view of the disposable absorbent undergarment of FIG. 11 during manufacturing and FIG. 13 is a side view of the disposable absorbent undergarment of FIG. 12.

For example, as shown, the elastomeric composite portions 108a, 108b include slot coated stretch adhesive portions 118a, 118b applied in a cross direction and positioned between the two substrate layers (Spunlace nonwoven, for example). In some embodiments, another two slot coat applicators may be used to apply stretch adhesive in an intermittent pattern for leg elastics (e.g., for front and/or back). The front and back sections 102, 104 further include elastic strand portions 130a, 130b, respectively, generally in the leg portion and including leg elastics 131 for providing stretching in the machine direction.

Various steps to manufacture the article corresponding to FIG. 11 can be similar to those described above for the embodiments of FIGS. 5 and 8, except for some differences described in further detail herein. For example, in Step 1, the stretch adhesive can be applied in two slot coat applications (continuous pattern) onto a Spunlace nonwoven web (portions 118a and 118b). Another Spunlace nonwoven web can be applied on top of the stretch adhesive, which can have the same or similar slit width as the first Spunlace nonwoven web. In Step 2, the stretch adhesive can be slot coated in two applications (both intermittent patterns) onto a SBPP (Spunbond Polypropylene) or SMS (Spunbond/Meltblown/Spunbond) nonwoven web. Next, leg elastics 131 can be applied (e.g., in stretched state) on top of the stretch adhesive and open area of the SBPP or SMS nonwoven web in curved patterns. Another SBPP or SMS nonwoven web can be applied directly on top of the stretch adhesive and open area, which can have the same or similar slit width as the first SBPP or SMS nonwoven web.

In Step 3, the leg elastics 131 can be cut by a "crush bond" process, which makes them snap back to where the intermittent pattern of elastic adhesive begins and ends. This can create an open or unglued area, which can be later registered and aligned to be under the insert 110 or absorbent core 112 area. In Step 4, the Spunlace nonwoven web and stretch adhesive from Step 1 can be cut or slit and ultrasonically bonded to the SBPP or SMS Nonwoven web & stretch adhesive in Step 2, which can create the stretch adhesive composite.

In Step 5, the stretch adhesive composite can be ultrasonically bonded to the front and back sections, as illustrated in FIGS. 11-13. In Step 6, the absorbent core can be registered and aligned to be in the "open area" of the stretch adhesive composite that includes SBPP or SMS nonwoven, such as in between the leg elastics (front and back). Steps 7 and 8 can be substantially similar to those described above for the embodiment of FIG. 5.

In the embodiment of FIG. 11, various additional materials of construction can include a Spunbond Polypropylene (SBPP) nonwoven, in the range of 8-60 gsm in basis weight. SBPP nonwoven is available from Avgol, Fitessa, Berry Plastics, etc. Furthermore, in some embodiments, a Spunbond-Meltblown-Spunbond (SMS) nonwoven, in the range of 8-60 gsm in basis weight, may be used. SMS nonwoven is available from Avgol, Fitessa, Berry Plastics, etc. Stretch adhesive, such as FLC-8500 from H. B. Fuller in Vadnais Heights, Minnesota. The leg elastic strands 131, such as Creora, in the range of 680-940 decitex, as available from Hyosung Corporation in Seoul, South Korea. Accordingly, as shown in FIG. 13, the undergarment may include the following construction: top and bottom layers 132 and 134 of SBPP, an elastic adhesive 136 to couple the elastic strands 131 to at least the top SBPP layer 132, Spunlace nonwoven layers 126 and 128, and the slot coated stretch adhesive 118 positioned between the Spunlace nonwoven layers 126 and 128.

Furthermore, an advantage of the embodiment of FIG. 11 includes improved breathability within the stretch adhesive composite and also has manufacturing process estimated to be the least expensive to manufacture of the three embodiments of FIGS. 5, 8, and 11.

Figure 14:
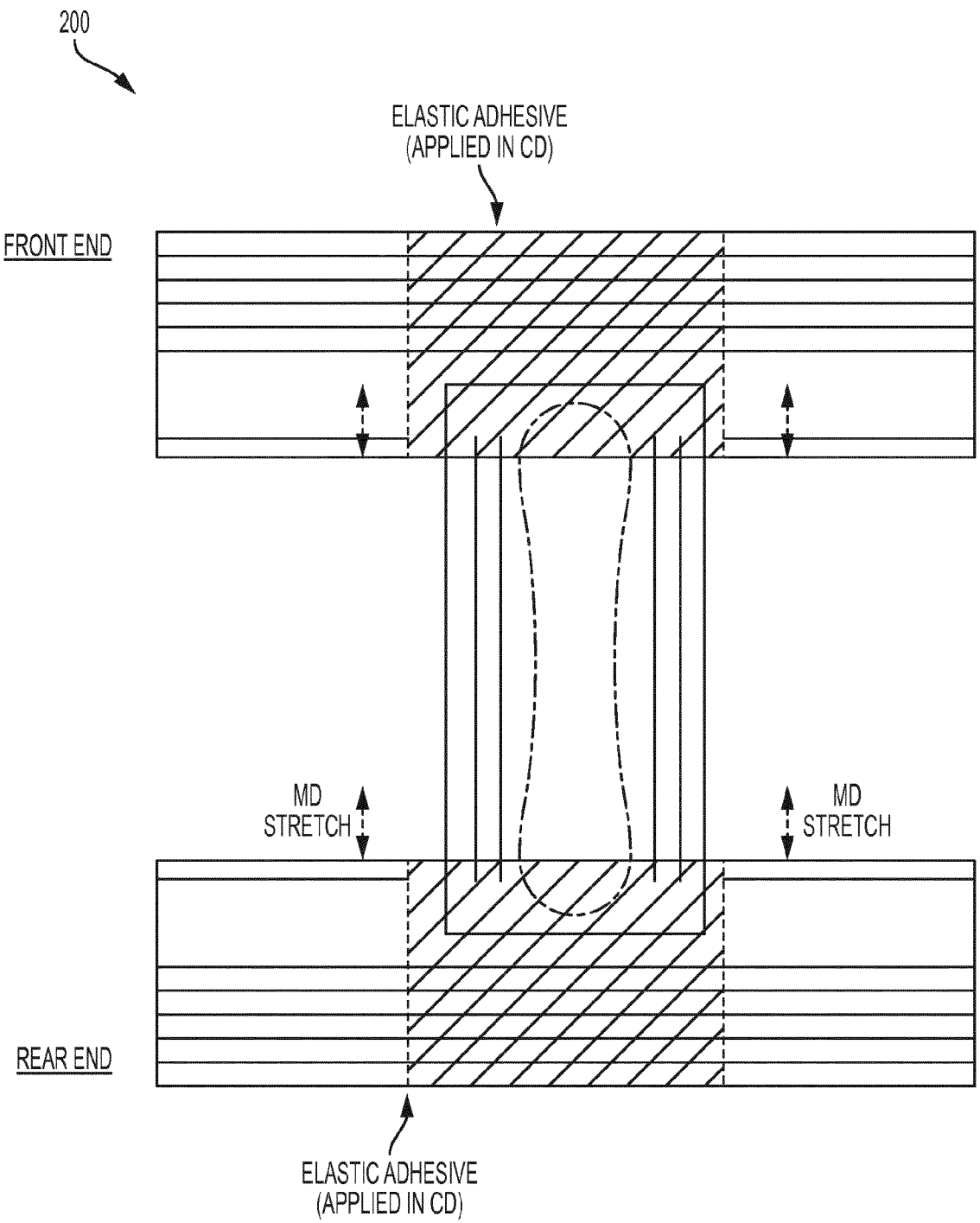
FIG. 14 is a top plan view of another embodiment of a disposable absorbent undergarment having a machine direction (MD) stretchable absorbent core as a result of a stretch adhesive composite provided on front and rear sections at positions adjacent to the insert.

FIG. 14 is a top plan view of another embodiment of a disposable absorbent undergarment having a machine direction (MD) stretchable absorbent core as a result of a stretch adhesive provided in a slot coat pattern on front and rear section assemblies at positions adjacent to the absorbent core. This embodiment includes using a slot coater to produce an article that corresponds to those in a co-owned patent application issued as U.S. Pat. No. 8,834,437 to Borrero et al. In this example, slot coater glue heads can apply a stretch adhesive on the inner nonwoven. The slot coater glue heads can be configured to apply adhesive to the inner nonwoven panel above the leg elastic weave pattern. The adhesive can be applied or "printed" in the CD direction and turn the glue on prior to the leading edge of the insert. The glue can be turned off at a trailing edge of the insert for both the front and back sections. In an example, the stretch adhesive has the characteristic that when printed in the CD direction it stretches in the MD direction. This feature can make the core extend and retract along the longitudinal axis of the core. In an example, the adhesive is printed only over an area of the insert which can create two different contraction regions: one over the insert area in the front and back section, and at the two areas on the outside of the front and back sections.

Figure 15:
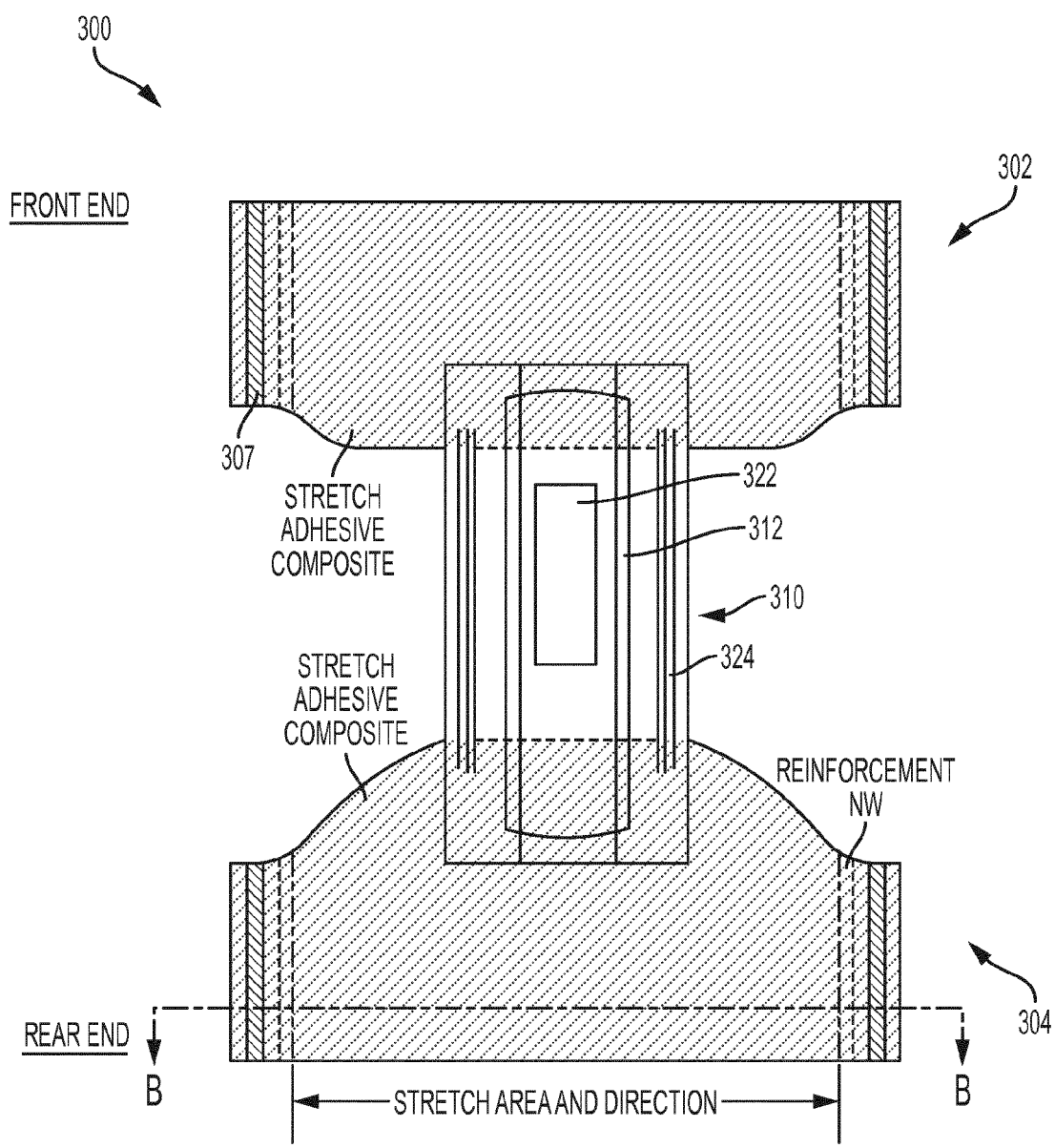
FIGS. 15 and 16 are top plan views of another embodiment of a disposable absorbent undergarment having cross direction (CD) stretchable front and rear sections as a result of a stretch adhesive composite provided on the majority of the front and rear sections.
Figure 16:
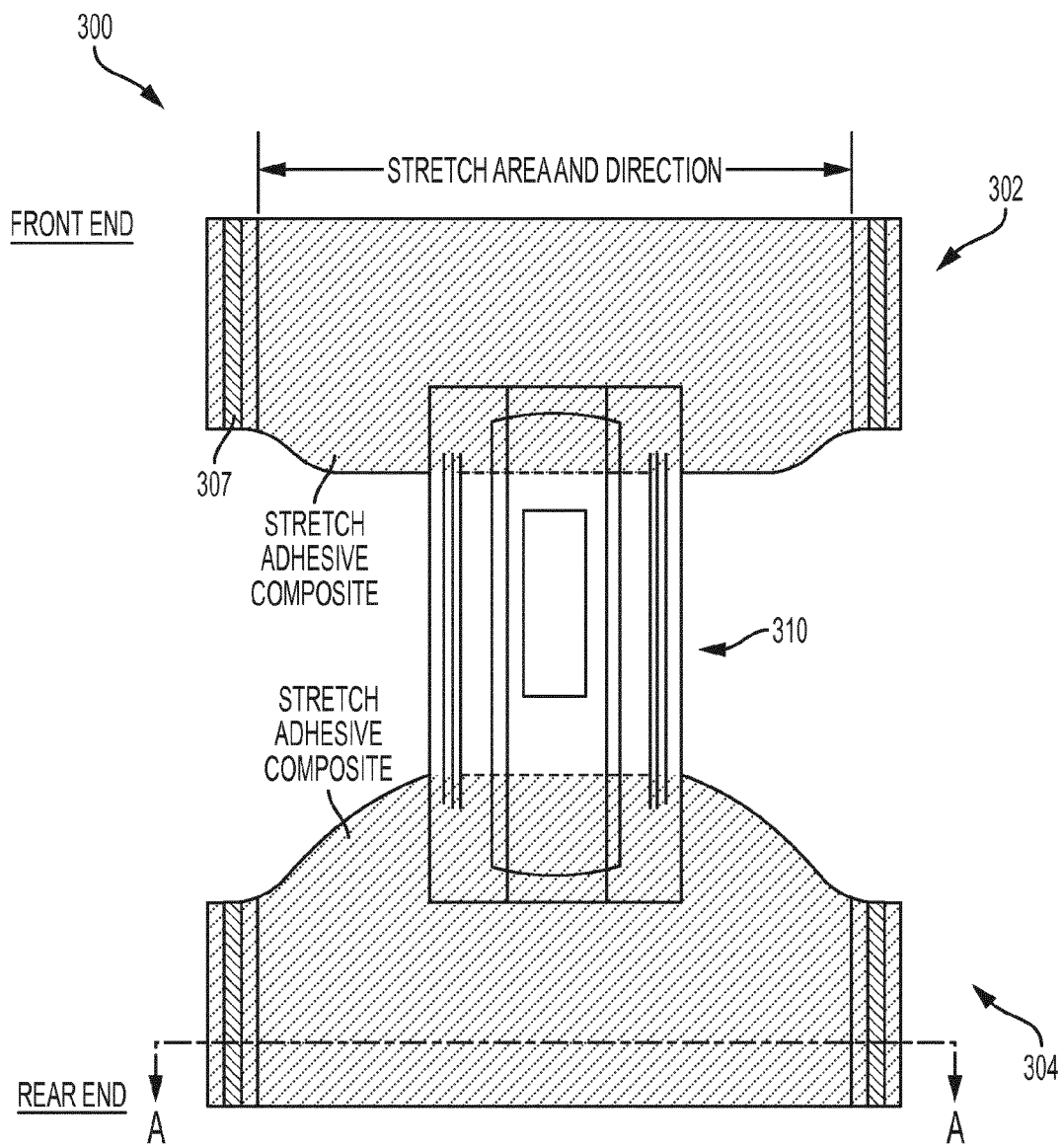

FIGS. 15 and 16 are top plan views of another embodiment of a disposable absorbent undergarment 300 having cross direction (CD) stretchable front and rear sections 302, 304, respectively, as result of a stretch adhesive composite in both the front and rear sections. As shown, the stretch adhesive composite is provided in a slot coat pattern and the composite comprises a majority of the area of each of the front and rear sections. As shown, the undergarment 300 includes an insert 310, including the absorbent core 312, acquisition layer 322, as well as crotch elastics 324, and stand-up leg gathers, etc.). The insert 310 may be adhered or bonded to both the front and back sections 302, 304 to complete the product assembly.

In one embodiment, a stretch adhesive composite for undergarment-related articles may include or use various different methods of ultrasonic bonding the materials together. For example, in one embodiment, the stretch adhesive composite may include two layers of Spunlace nonwoven bonded together. In another embodiment, the stretch adhesive composite may include, two layers of Spunlace and stretch adhesive bonded together. In another embodiment, the stretch adhesive composite may include two layers of Spunlace and a Reinforcement nonwoven layer bonded together.

In the embodiment shown in FIG. 15, the undergarment 300, specifically the front and rear sections 302, 304 include a stretch adhesive composite having two layers of Spunlace and Reinforcement nonwoven ultrasonically bonded together. In this embodiment, a Reinforcement nonwoven can be extended well into the stretch adhesive area and then expanded outward and positioned in between the Spunlace nonwoven webs. The Reinforcement nonwoven can provide material strength to the Spunlace nonwoven webs and in some examples does not stretch. The Reinforcement nonwoven may also extend into the stretch adhesive area in order to provide material strength to the entire stretch adhesive composite. Since this Reinforcement material may not stretch, it can be only partially extended into the stretch adhesive area.

The section of the stretch adhesive composite contain Spunlace nonwoven webs and Reinforcement nonwoven, can be either mechanically heat crimped or ultrasonically bonded together, which can ultimately fuse the polypropylene fibers together and make the material stronger in tensile strength. As the undergarment progresses down the assembly chain during the undergarment manufacturing process, this section can be ultrasonically bonded at the sides, after the undergarment is folded in half. Generally, areas of stretch adhesive are kept away from ultrasonic bonding areas in order to minimize adhesive build-up on the equipment.

Figure 17:
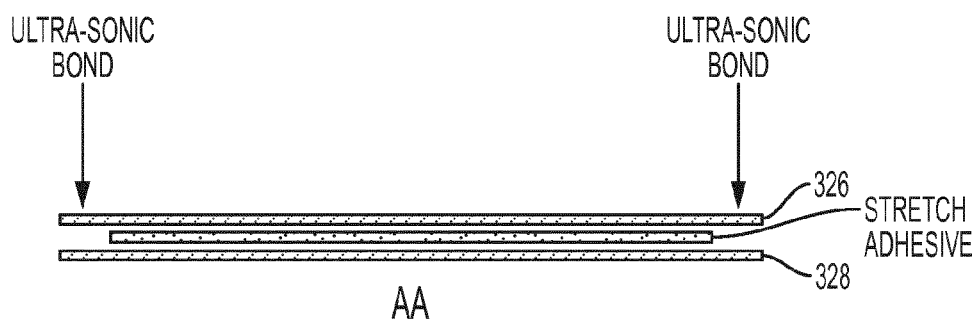
FIG. 17 is a side view of the disposable absorbent undergarment of FIG. 16 during manufacturing illustrating the stretch adhesive between two layers of Spunlace to form the stretch adhesive composite.

The undergarment illustrated in FIG. 16 is similar to the embodiment of FIG. 15, however, the embodiment in FIG. 16 includes either a stretch adhesive composite in which either the two layers of Spunlace nonwoven are ultrasonically bonded together or the two layers of Spunlace and stretch adhesive are ultrasonically bonded together. For example, as shown in FIG. 17, the stretch adhesive composite includes the stretch adhesive between two layers of Spunlace and ultrasonically bonded together.

Figure 18:
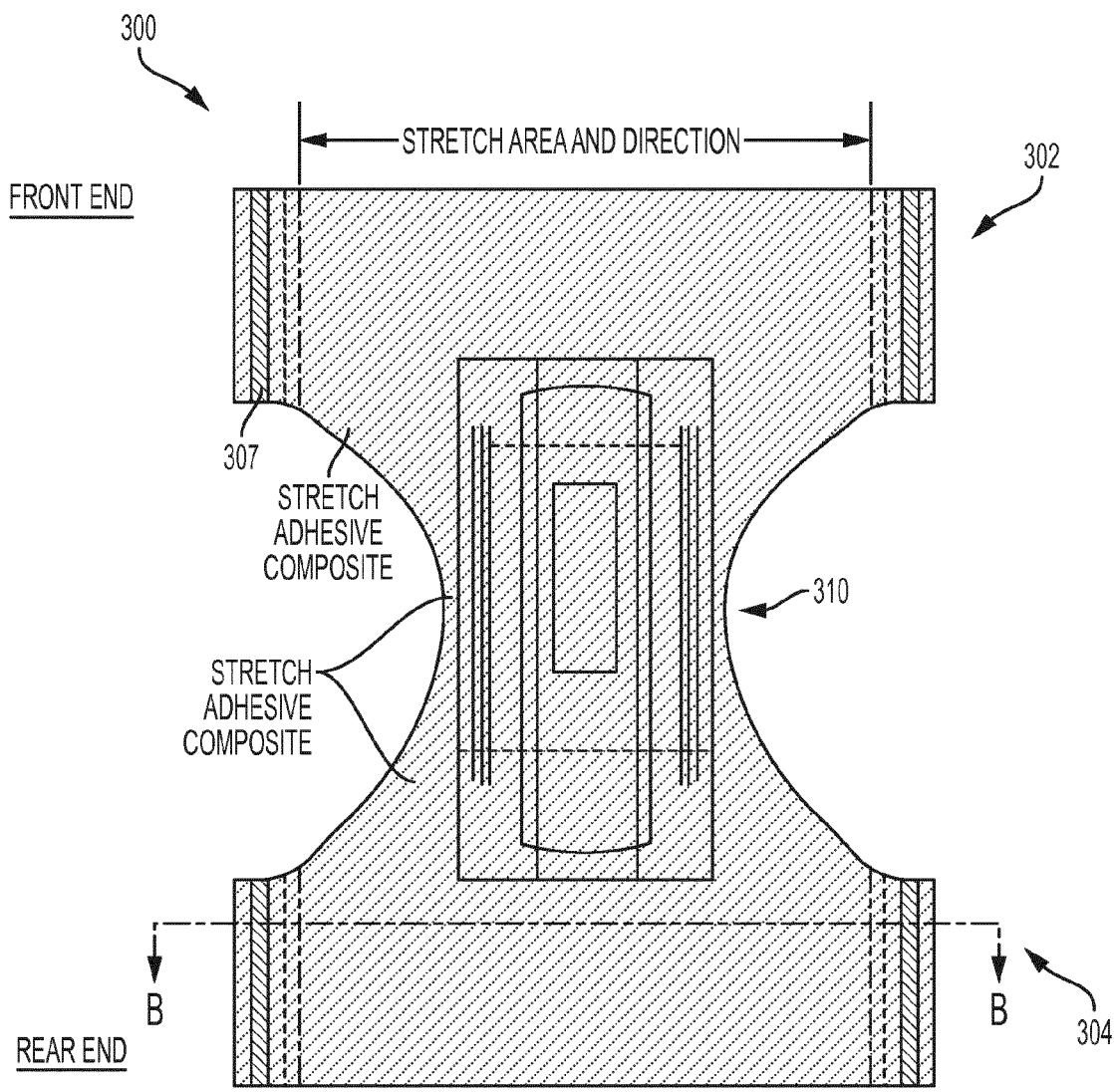
FIG. 18 a top plan view of another embodiment of a disposable absorbent undergarment having cross direction (CD) stretchable front and rear sections and insert as a result of a stretch adhesive composite provided across the entire undergarment, including the front and rear sections and the insert, the stretch adhesive composite including a slot coated stretch adhesive.

FIG. 18 a top plan view of another embodiment of a disposable absorbent undergarment 300 having cross direction (CD) stretchable front and rear sections 302, 304 and the insert 310 as a result of a stretch adhesive composite provided across a majority of the entire article (i.e., across the front and rear sections and the insert). However, other cross directional (CD) stretch materials or composites can be used as well. For example, the insert 310, which may generally include, but is not limited to, at least one of the absorbent core 312, acquisition layer 322, crotch elastics 324, stand-up leg gathers, etc., can be adhered or bonded directly to the stretch adhesive composite. In this example, there are no separate front or back sections. The embodiment of FIG. 18 provides an advantage over other undergarment designs in that the entire product chassis is made-up of a single material, which may make the appear like a real, non-disposable undergarment or underwear. The stretch adhesive composite can also appear more cloth-like, such as spandex, which is soft and flexible. Such designs are described in greater detail herein.

Figure 19:
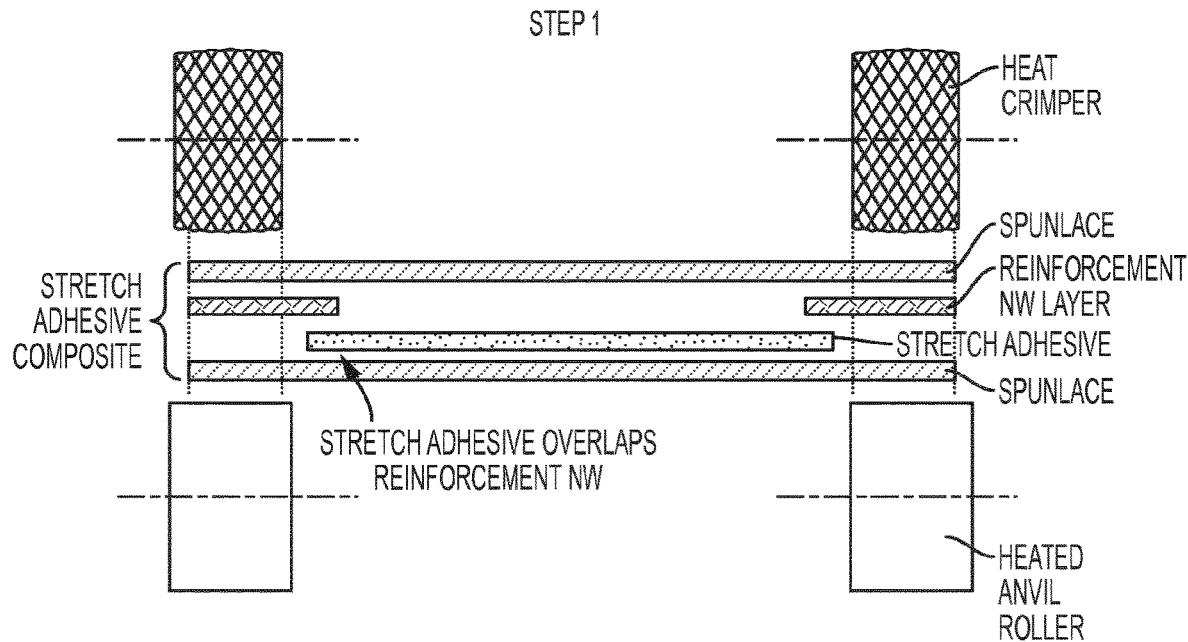
FIGS. 19 and 20 are side views of the process of manufacturing the disposable absorbent undergarments of one or more of FIGS. 15, 16, and 18.
Figure 20:
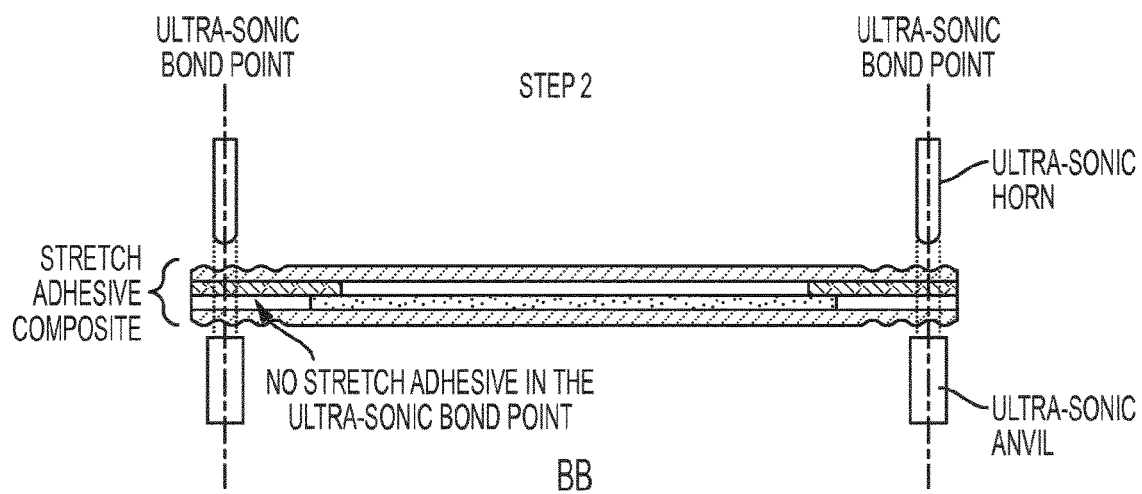

FIGS. 19 and 20 are side views of the process of manufacturing the disposable absorbent undergarments 300 of one or more of FIGS. 15, 16, and 18. For example, FIG. 19 illustrates a first step (i.e., Step 1) in which the stretch adhesive composite, which includes two Spunlace nonwoven layers and a Reinforcement nonwoven (positioned between the two layers) bonded together via a mechanical and heat crimping process. The stretch adhesive is positioned between the two Spunlace nonwoven layers along with the Reinforcement nonwoven layer, wherein sides of the stretch adhesive overlap with edges of the Reinforcement nonwoven. Accordingly, as a result of the mechanical and heat crimping process, the two Spunlace nonwoven layers and the Reinforcement nonwoven are bonded together in an area in which the stretch adhesive is not present. FIG. 20 illustrates a second step (i.e., Step 2) in which only the two Spunlace nonwoven layers and the Reinforcement nonwoven layer are ultrasonically bonded together along the sides of the sections in an area in which the stretch adhesive is not present.

Figure 21:
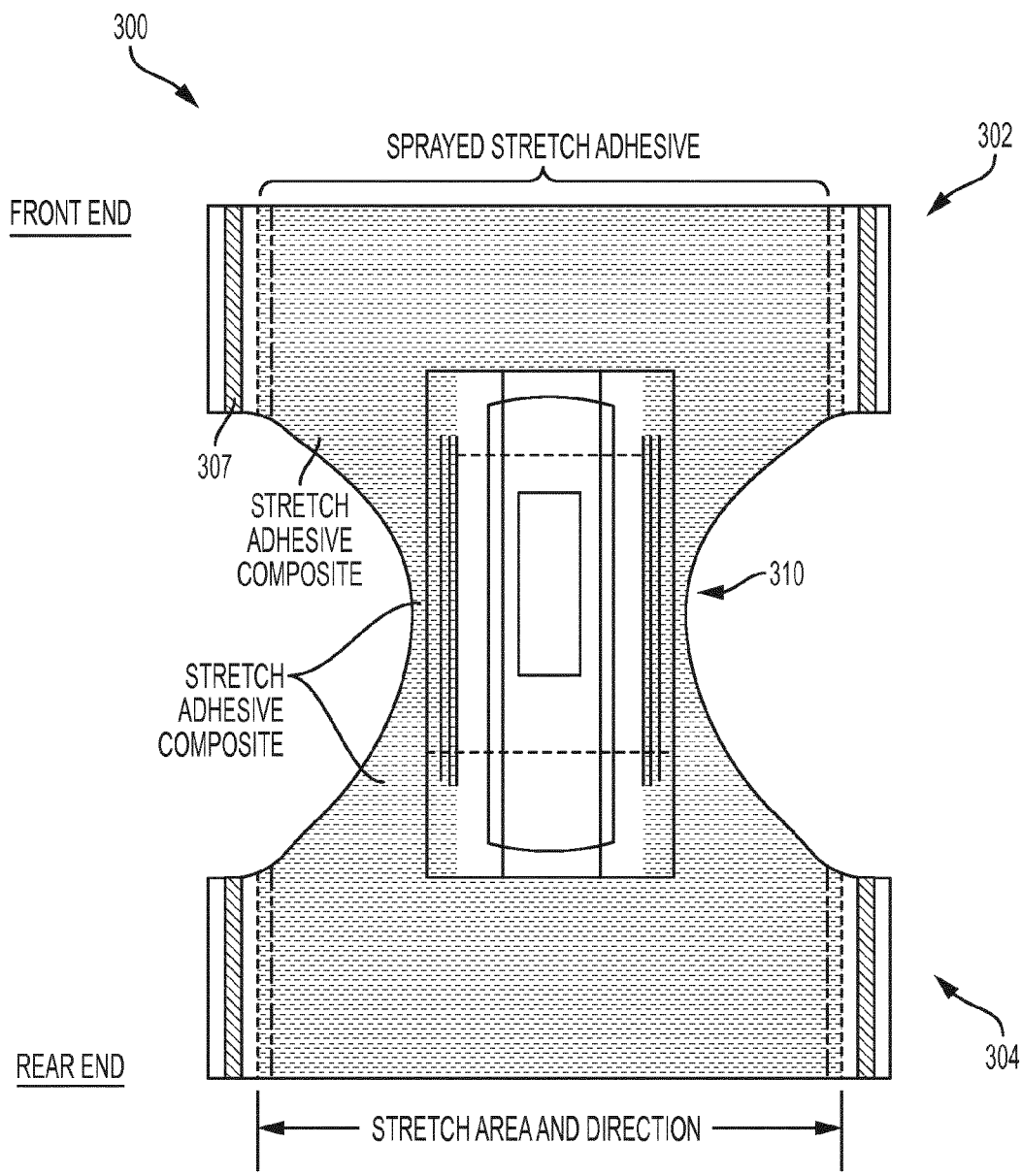
FIG. 21 is a top plan view of another embodiment of a disposable absorbent undergarment having cross direction (CD) stretchable front and rear sections and a portion of the insert as a result of a stretch adhesive composite provided on front and rear sections and a portion of the insert, the stretch adhesive composite including a sprayed stretch adhesive.

FIG. 21 is a top plan view of another embodiment of a disposable absorbent undergarment 300 having cross direction (CD) stretchable front and rear sections and a portion of the insert 310 as a result of a stretch adhesive composite forming portions of the front and rear sections 302, 304 including a stretch adhesive applied in a sprayed pattern. In this example, a product can be manufactured in the machine direction (MD) and the stretch adhesive can be sprayed (e.g., sprayed on the left and right sides of the product, such as in a continuous pattern. The stretch adhesive can be sprayed in a middle section of the product, for example, using an intermittent pattern. In an example, the stretch adhesive spray in the middle section can overlap the spray in the left and right sections, in order to provide tensile strength throughout the cross-section of the chassis. The stretch adhesive can nearly or completely surround a perimeter of the absorbent core, for example, acting as a gasket to prevent leaks, which in turn may also further provide a "fully breathable" product chassis.

Figure 22:
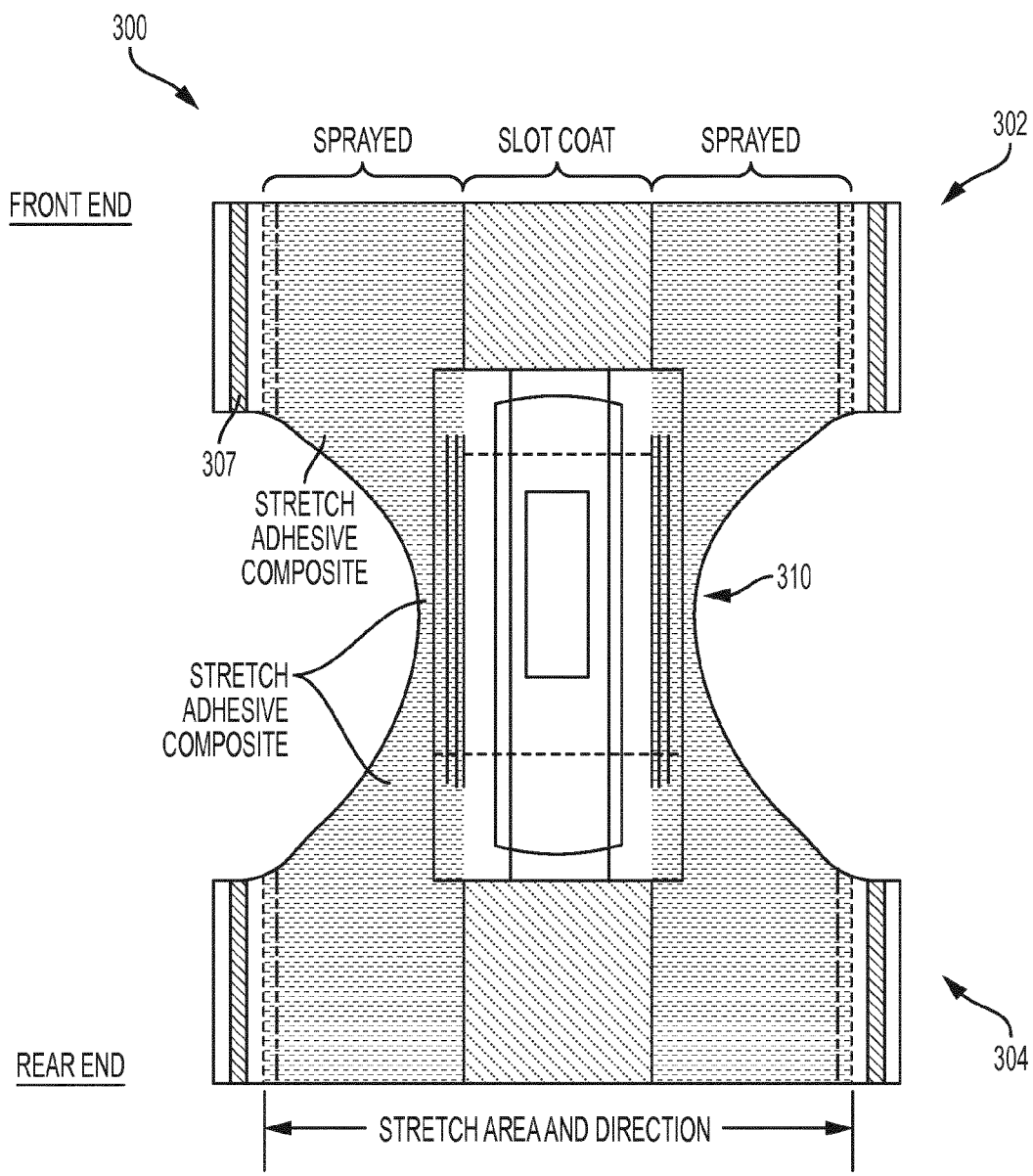
FIGS. 22 and 23 are top plan views of other embodiment of a disposable absorbent undergarment having cross direction (CD) stretchable front and rear sections and a portion of the insert as a result of a stretch adhesive composite provided on front and rear sections and a portion of the insert, the stretch adhesive composite including a combination of a slot coated stretch adhesive and a sprayed stretch adhesive.

FIG. 22 is a top plan view of another embodiment of a disposable absorbent undergarment 300 having cross direction (CD) stretchable front and rear sections and a portion of the insert as a result of a stretch adhesive composite forming portions of the front and rear sections 302, 304 including a stretch adhesive applied in a combination slot coat pattern and sprayed pattern on the front and rear sections and portions of the insert. In this example, the product can be manufactured in the machine direction (MD) and stretch adhesive can be slot coated in a middle section of the product, such as using an intermittent application pattern. The stretch adhesive can further be sprayed in the left and right sides of the product, for example, using a continuous pattern. In one example, the stretch adhesive spray may slightly overlap the slot coated section, in order to provide tensile strength throughout the cross-section of the chassis. In another example, stretch adhesive may completely or may partially surround a perimeter of the absorbent core, acting as a gasket to prevent leaks, which may provide a "partially breathable" product chassis.

Figure 23:
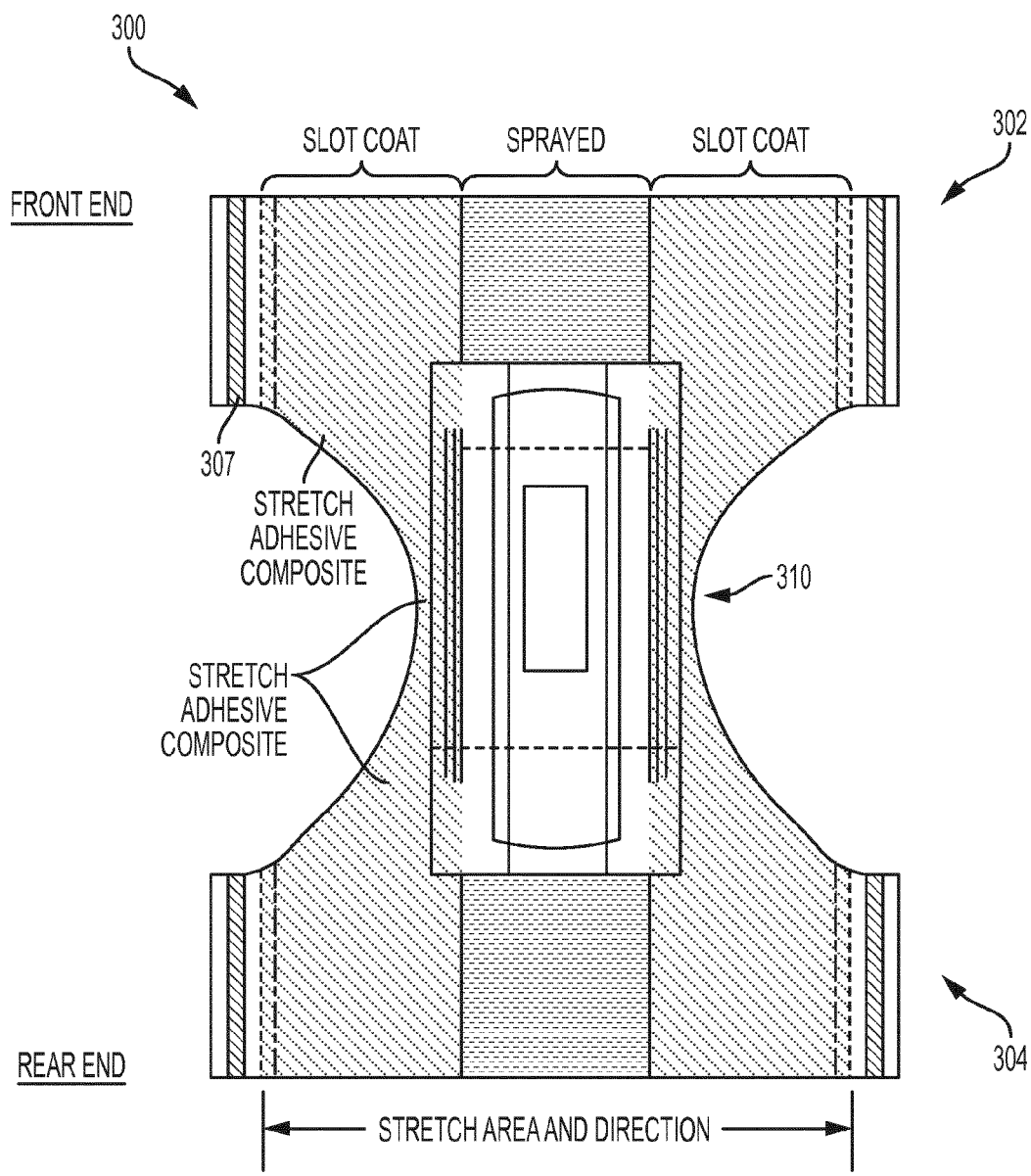

FIG. 23 is a top plan view of another embodiment of a disposable absorbent undergarment 300 having cross direction (CD) stretchable front and rear sections and a portion of the insert as a result of a stretch adhesive composite forming portions of the front and rear sections 302, 304 including a stretch adhesive applied in a combination slot coat pattern and sprayed pattern on the front and rear sections and portions of the insert 310. In this example, the product can be manufactured in the machine direction (MD) and the stretch adhesive can be slot coated on the left & right sides of the product, such as in a continuous pattern. The stretch adhesive can be sprayed in the middle section of the product, such as using an intermittent pattern. In one example, the sprayed stretch adhesive may slightly overlap the slot coated section, so as to provide tensile strength throughout the cross-section of the chassis. In an example, the stretch adhesive may partially, or completely, surround the perimeter of the absorbent core, acting as a gasket to prevent leaks. In this example, the product includes a "partially breathable" product chassis.

Figure 24:
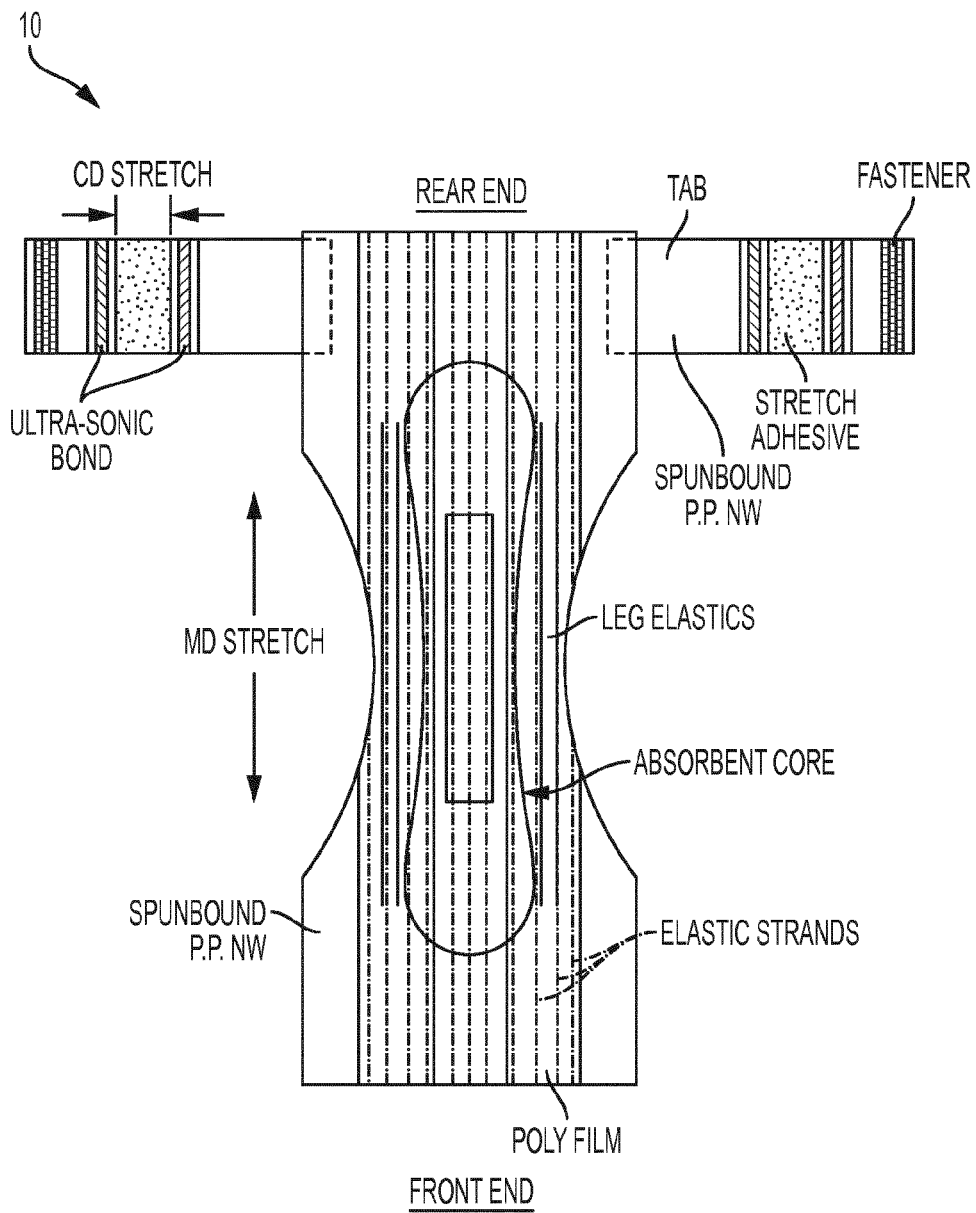
FIGS. 24 and 25 are top plan views of the exemplary disposable absorbent undergarment of FIG. 1 illustrating the use of a stretch adhesive composite on the fastening tabs to allow a cross direction (CD) stretch of the fastening tab.
Figure 25:
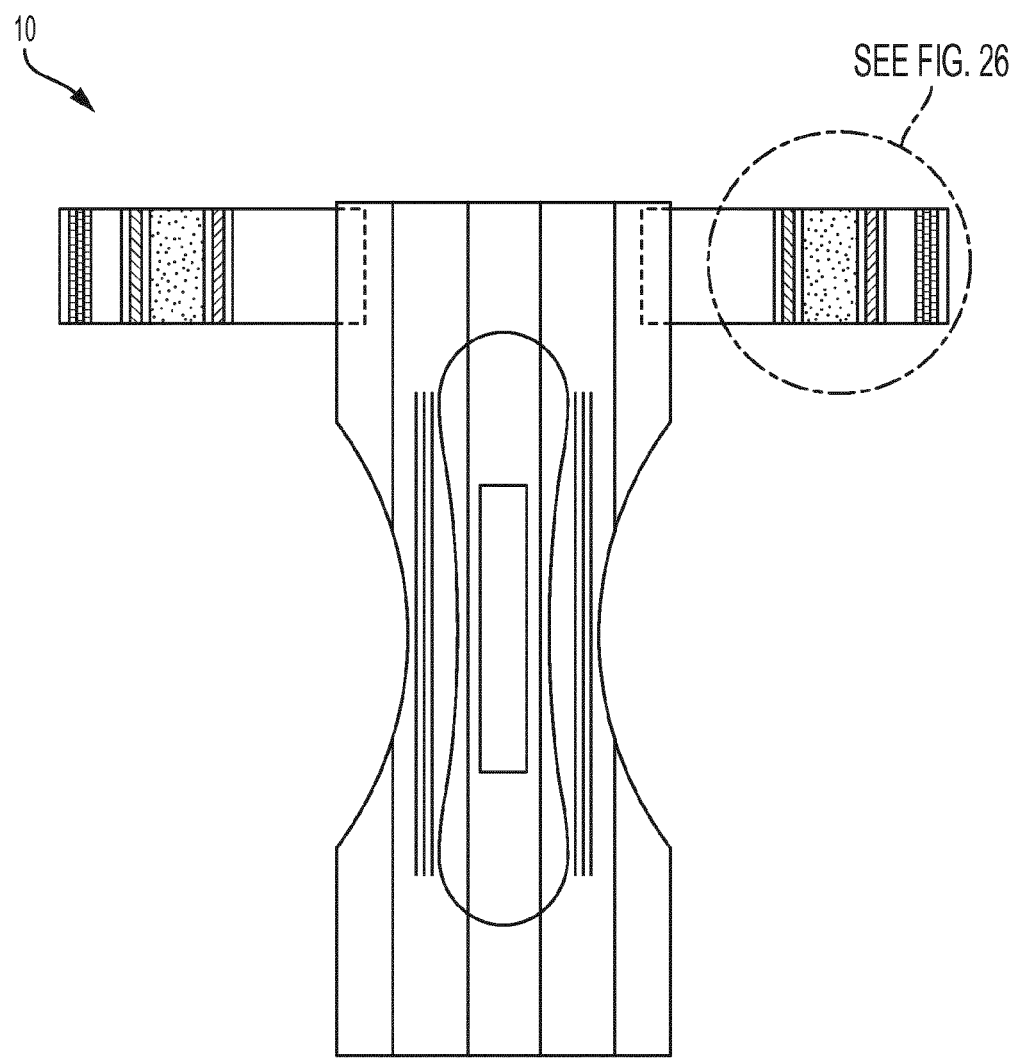

FIGS. 24 and 25 are top plan views of the exemplary disposable absorbent undergarment of FIG. 1 illustrating the use of a stretch adhesive composite on the fastening tabs to allow a cross direction (CD) stretch of the fastening tab. For example, FIGS. 24 and 25 generally illustrate the undergarment with fastening tabs (also referred to herein as "side panels" or "panels"). The embodiment of FIGS. 24 and 25 may be useful as an adult brief-style incontinence article or a baby diaper article, for example, including one or more closure mechanisms. In this example, elastic strands can be stretched and adhered between a nonwoven backsheet and poly film in the MD (Machine Direction). The elastic strands can range from 680-940 decitex and can be elongated from 100%-300%. In some embodiments, the elongation is approximately 150%-200% and the decitex is about 680. The elastic strands can retract the product at both the front and back ends and allow it to stretch in the ID bringing the absorbent core closer to the body.

Figure 26:
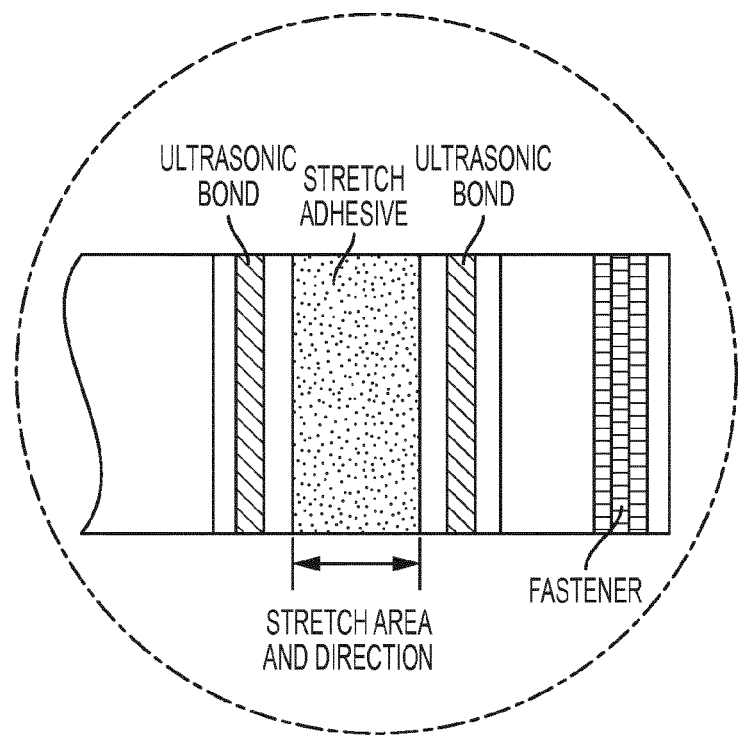
FIG. 26 is an enlarged top view of the fastening tab of FIG. 25 illustrating the stretch adhesive composite provided on the fastening tab, including a slot coated stretch adhesive.
Figure 27:
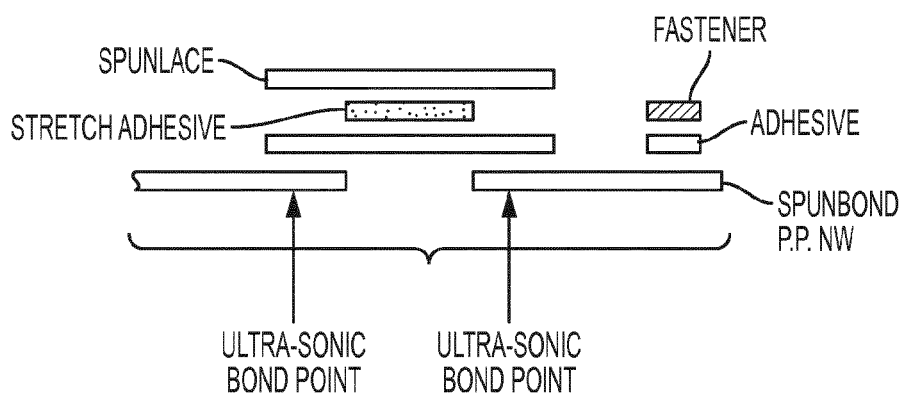
FIG. 27 is an exploded side view of the fastening tab of FIG. 25 illustrating the different layers and assembly of thereof.

FIG. 26 is an enlarged top view of the fastening tab of FIG. 25 illustrating the stretch adhesive composite provided on the fastening tab, including a slot coated stretch adhesive. In addition, the stretch adhesive can be applied with a spray pattern or combined slot coat and spray pattern. FIG. 27 is an exploded side view of the fastening tab of FIG. 25 illustrating the different layers and assembly of thereof.

Figure 28:
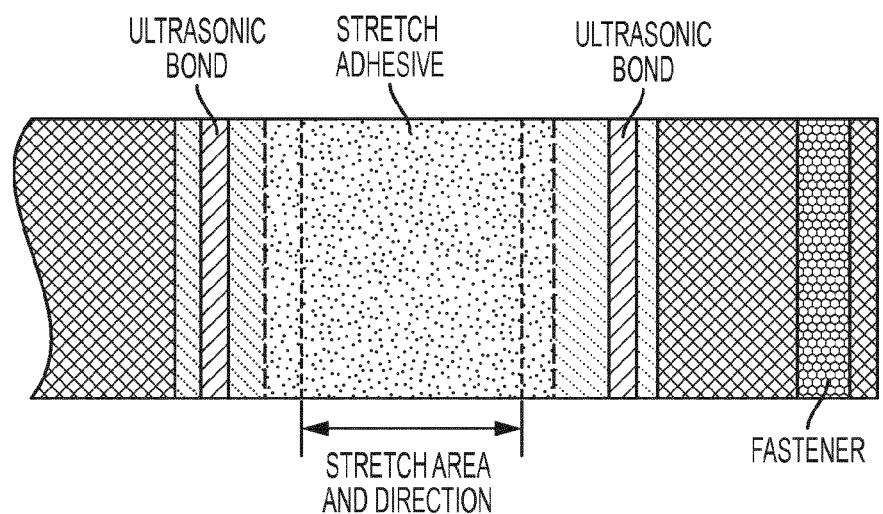
FIG. 28 is an enlarged top view of the fastening tab of FIG. 25 illustrating the stretch adhesive composite provided on the fastening tab in a slot coat pattern.
Figure 29:
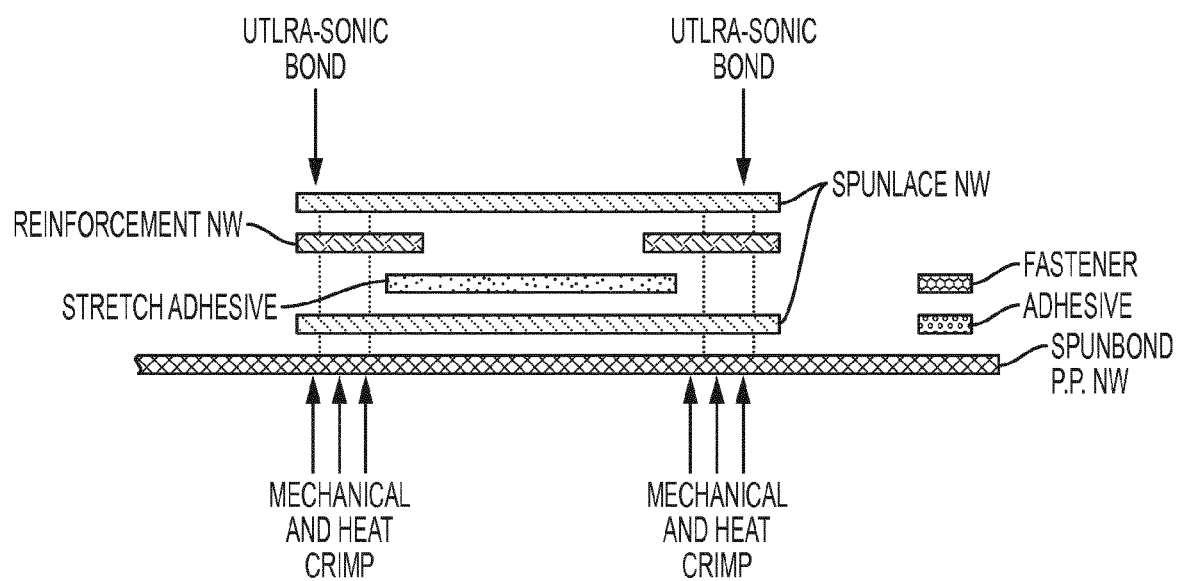
FIG. 29 is an exploded side view of the fastening tab of FIG. 25 illustrating the different layers and assembly of thereof.

FIG. 28 is an enlarged top view of the fastening tab of FIG. 25 illustrating the stretch adhesive composite provided on the fastening tab including Reinforcement nonwoven. The stretch adhesive may be applied via slot coated, spray or a combination of both. FIG. 29 is an exploded side view of the fastening tab of FIG. 25 illustrating the different layers and assembly of thereof.

As previously described herein, particularly with reference to FIGS. 15-20, there are at least three different methods in bonding materials together for attaching the stretch adhesive composite to the side panel base material. One method is illustrated in FIGS. 26 and 27, in which the stretch adhesive composite generally comprises a stretch adhesive positioned between two Spunlace nonwoven layers that are subsequently ultrasonically bonded together. Another method is illustrated in FIGS. 28 and 29, in which the stretch adhesive composite generally comprises a stretch adhesive and a Reinforcement nonwoven layer that are positioned between two Spunlace nonwoven layers that are subsequently mechanically and heat crimped to one another and then ultrasonically bonded together.

For example, FIG. 29 illustrates Steps 1 and 2 described previously with regard to FIGS. 19 and 20, in which the stretch adhesive composite, which includes two Spunlace nonwoven layers and a Reinforcement nonwoven (positioned between the two layers) bonded together via a mechanical and heat crimping process. The stretch adhesive is positioned between the two Spunlace nonwoven layers along with the Reinforcement nonwoven layer, wherein sides of the stretch adhesive overlap with edges of the Reinforcement nonwoven. Accordingly, as a result of the mechanical and heat crimping process, the two Spunlace nonwoven layers and the Reinforcement nonwoven are bonded together. In addition, the two Spunlace nonwoven layers and the Reinforcement nonwoven layer are ultrasonically bonded together along the sides of the panels in an area in which the stretch adhesive is not present.

Figure 30:
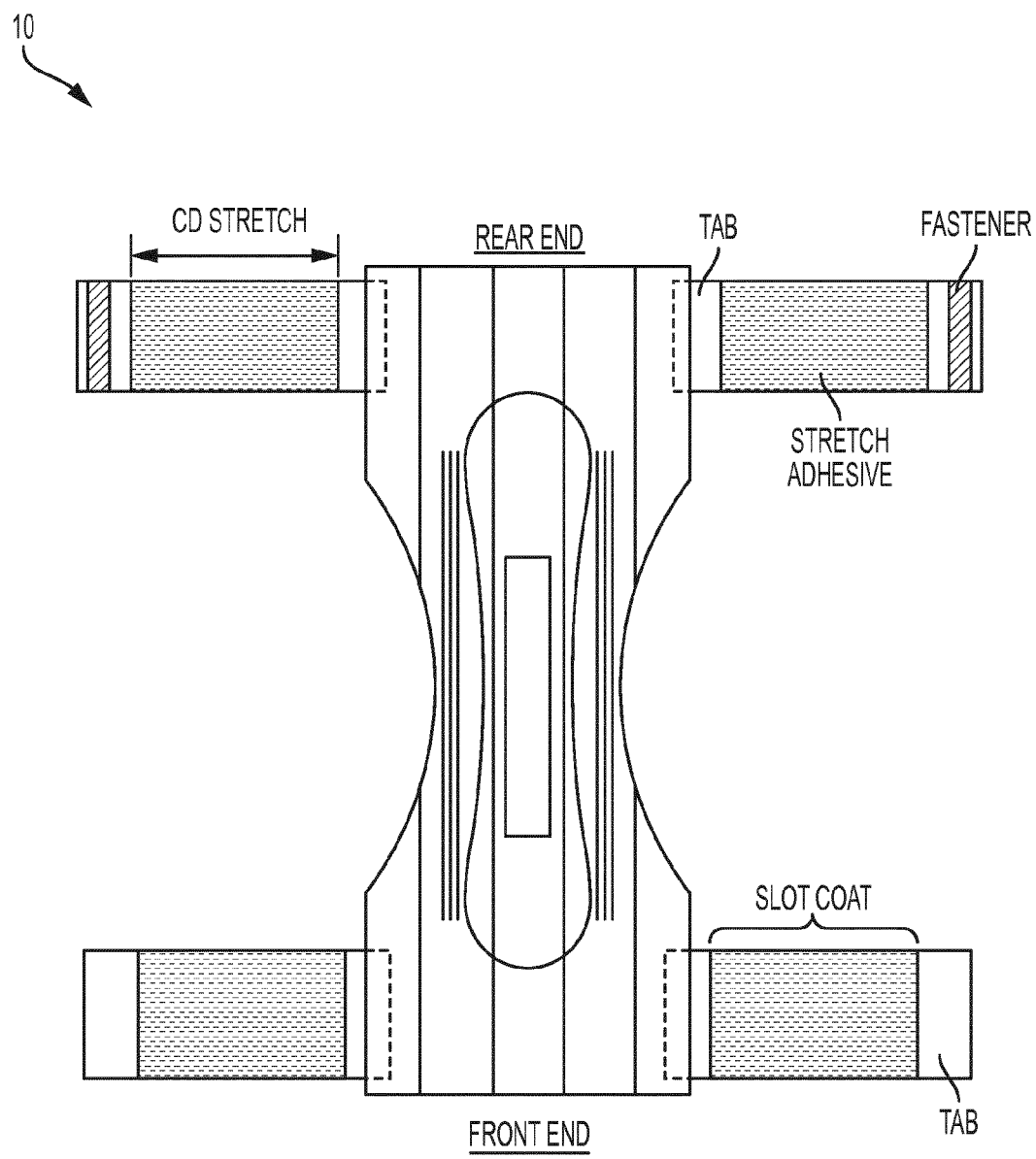
FIG. 30 is a top plan view of another embodiment of the exemplary disposable absorbent undergarment of FIG. 1 illustrating the use of a stretch adhesive composite on fastening tabs provided on both the front and rear sections to allow a cross direction (CD) stretch of the fastening tabs, the stretch adhesive applied in a slot coat pattern.
Figure 31:
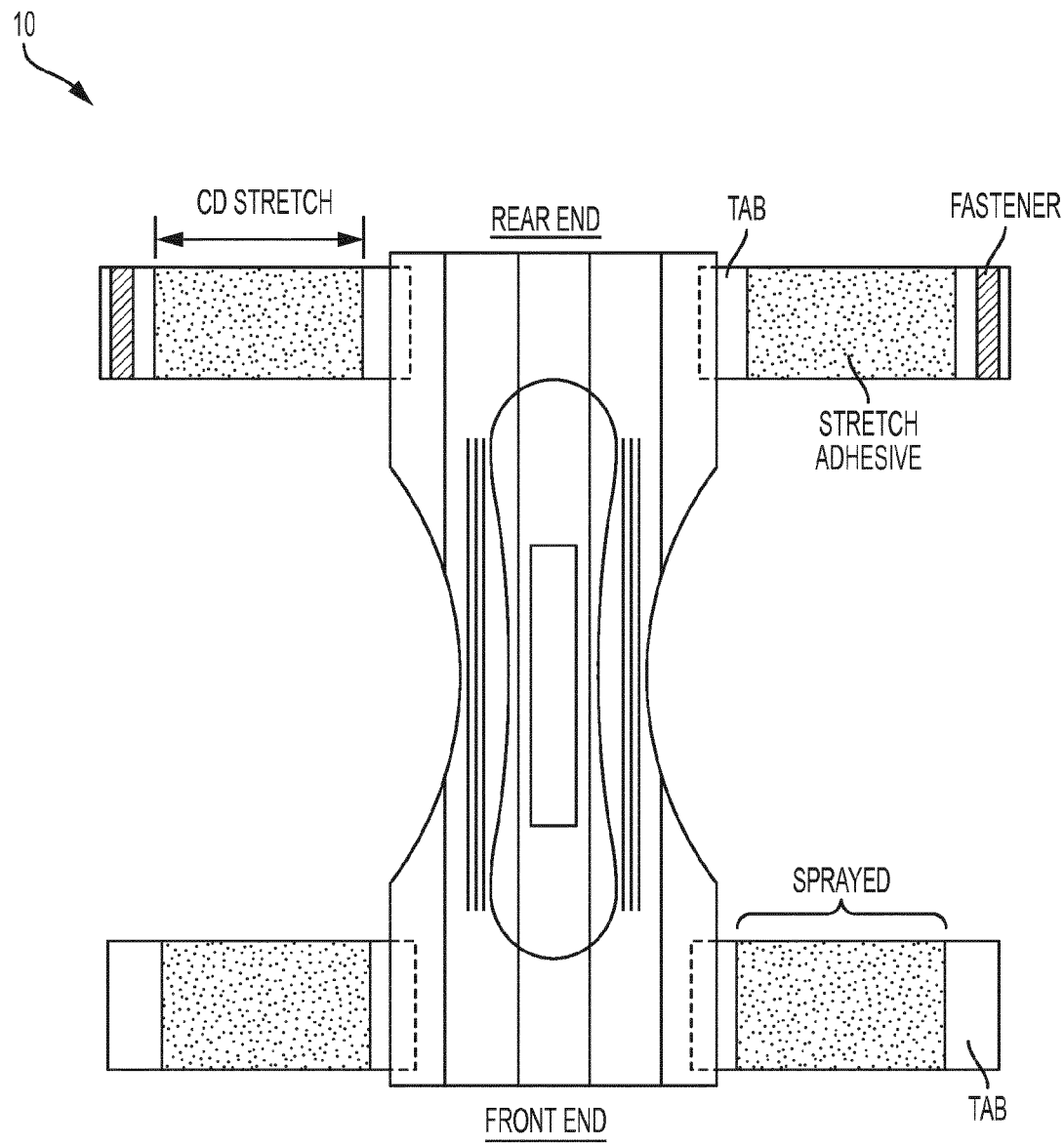
FIG. 31 is a top plan view of another embodiment of the exemplary disposable absorbent undergarment of FIG. 1 illustrating the use of a stretch adhesive composite on fastening tabs provided on both the front and rear sections to allow a cross direction (CD) stretch of the fastening tabs, the stretch adhesive applied in a sprayed pattern.

FIGS. 30 and 31 illustrate embodiments of four-panel briefs that may include or use a stretch adhesive material. For example, FIG. 30 is a top plan view of another embodiment of the exemplary disposable absorbent undergarment of FIG. 1 illustrating the use of a stretch adhesive composite on fastening tabs or panels provided on both the front and rear panel assemblies to allow a cross direction (CD) stretch of the fastening tabs, the stretch adhesive applied in a slot coat pattern. In this example, the stretch adhesive can be slot coated. One, two, three, or four of the side panels can include a stretch adhesive. Optionally, only the side panels corresponding to the back portion of the article include the stretch adhesive. If only the back side panels contain stretch adhesive, then another material can optionally be used for the front side panels. In one embodiment, the same material could be used for both the back and front side panels if the stretch adhesive is intermittently applied to the material and the rest of the material is thermally crimped or ultrasonically bonded, as the material that the stretch adhesive is applied to needs to stretch and is structurally weak in the CD. Accordingly, such material can be reinforced by bonding the loose fibers together in a permanent thermal set.

FIG. 31 is a top plan view of another embodiment of the exemplary disposable absorbent undergarment of FIG. 1 illustrating the use of a stretch adhesive composite on fastening tabs provided on both the front and rear panel assemblies to allow a cross direction (CID) stretch of the fastening tabs, the stretch adhesive applied in a sprayed pattern. In this example, the stretch adhesive can be sprayed, e.g., using an intermittent pattern. It is to be understood that FIGS. 30 and 31 can also comprise stretch adhesive applied by a combination of slot coat and spray.

Figure 32:
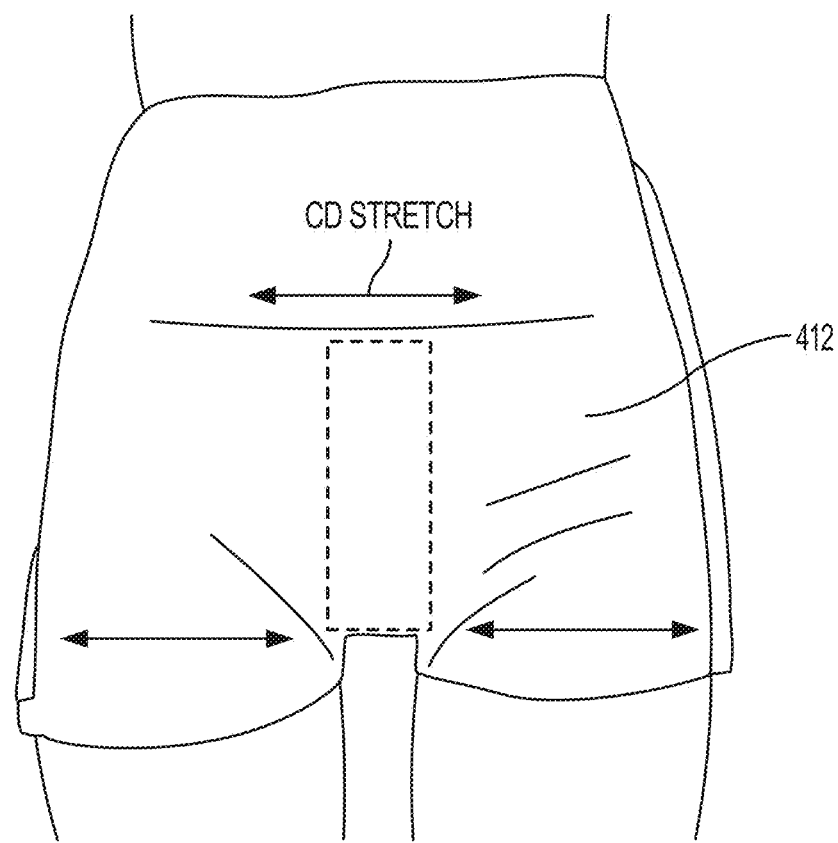
FIG. 32 is a front view of a disposable absorbent undergarment comprised of an elastomeric composite material and shown in the worn configuration.

While the undergarment in the above embodiments is generally in the form of a baby diaper or adult brief, the embodiments described below are generally in the form of disposable underwear or training pants. For example, FIG. 32 depicts a front view of a disposable absorbent undergarment comprised of an elastomeric composite material and shown in the worn configuration. As with the embodiments of FIGS. 1-4, the elastomeric absorbent article of FIG. 32 includes a front portion and a rear portion (not shown) wherein the front portion is generally designed to be fitted against the front, or anterior portion, of a wearer, while the rear portion is generally designed to be fitted against the rear, or posterior portion, of the wearer, such that front and rear portions generally oppose one another once fitted to the wearer. This is illustrated in FIGS. 33A and B. The absorbent article also includes a crotch portion 430 which encompasses the region in which the absorbent core is attached and spans to both the front 412 and rear 414 portions. The absorbent article 410 can have various shapes and sizes, and is generally configured to be worn between an individual's legs and secured about the waist, as shown.

Referring to FIGS. 33A and B, in one embodiment, the absorbent article 410 can have a front edge 411, a rear edge 413, and two side edges 415 and 416, the rear edge 413 located at the waist opening at the rear portion 414 and the front edge 411 located at the waist opening on the front portion 412. The absorbent article can be folded along a line called the "fold point" 450 located between and substantially parallel with the front edge 411 and the rear edge 413, as shown in FIG. 3313. The leg openings 452 and 453 can be provided along the fold point 450.

In another embodiment (not shown), the front portion 12 and the rear portion 14 are separate pieces, such that each portion has a top edge, a bottom edge and two side edges. Rather than folding the article at a fold point between the two portions, in this embodiment, the portions are joined at the edges, such as at the bottom edge of each portion and the side edges.

Generally, the elastomeric absorbent article 410 includes an elastomeric material 420 coupled to at least one substrate layer 440 to form at least one elastomeric composite. The elastomeric composite is mainly responsible for providing a smooth contoured fit to the body of the wearer. In one embodiment, the elastomeric material 420 is coupled to a single substrate layer 440 to form an elastomeric composite. In another embodiment, the elastomeric material is disposed between two substrate layers 440, 446 to form a single elastomeric composite (see FIGS. 36A and 13). In yet another embodiment, a first elastomeric material 420 is coupled to the first substrate layer 440 to form a first elastomeric composite and a second elastomeric material 420 is coupled to the second substrate layer 446 to form a second elastomeric composite (see FIGS. 37-40). In some embodiments, the one or more substrate layers can server as a back sheet or top sheet, as provided above.

The substrate layer(s) 440, 446 can be made of the same material or different material. The material is preferably a non-woven material. The substrate layers can be comprised of, for example, non-woven fibers, such as polypropylene (PP), polyethylene (PE), polyethylene terephthalate (PET), Bi-component Fiber (PE Sheath/PET Core or PE Sheath/PP Core), polyester, cotton, cotton blend, viscose, rayon, etc. or any combination thereof; melt-blown nonwovens; spunlaid (Spunlace) nonwovens, such as PP spunbounds and PET spunbounds; melt-blown and spunbound combinations (SM), including spun-melt-spun (SMS); and airlaid paper; or any combinations thereof. In a preferred embodiment, the substrate layers comprise a Spunlace material, such as Fibrella Lite (25-30 gsm) available from Suominen Corporation in Helsinki, Finland.

The substrate layers may each be comprised of a single layer, or each substrate layer may itself comprise multiple layers, such as 2, 3, 4, 5, 6, 7, 8, 9, 10, or more layers. When multiple layers are provided, the layers can all have the same thickness, each layer can have a different thickness, or some layers can have the same thickness while others have different thicknesses. Each layer can have a constant thickness or a variable thickness. Additionally, the layers can all be made up of the same material or of different materials, such as 2, 3, 4, 5, 6, 7, 8, 9, 10, or more different materials. Each layer itself can also be made up of more than one material (e.g., 2, 3, 4, 5, 6, 7, 8, 9, 10, or more), such that the materials are non-homogeneously distributed. Additionally, in an embodiment wherein two substrate layers are provided, when one or both of the substrate layers 440 and 446 contain more than one layer, at least a portion of the elastomeric material 420 can be disposed within the layers, such that the elastomeric material 420 is coupled to two different layers within the same substrate layer.

In some embodiments, the elastomeric material 420 is coextensive with the substrate layer(s) to which it is coupled. In another words, the elastomeric material 420 extends from the front edge 411 to the rear edge 413 and from the first side edge 415 to the second side edge 416 of the absorbent article 410, such that the elastomeric material 420 has the same footprint as the substrate layer. In other embodiments, the elastomeric material 420 is not coextensive with the substrate layer. For example, the elastomeric material 420 may cover 5%, 10%, 15%, 20%, 25%, 30%, 35%, 40%, 45%, 50%, 55%. 60%, 65%, 70%, 75%, 80%, 85%, 90%, 95%, 99% of the substrate layer, and any percentage there between. For example, in one embodiment, the elastomeric material 420 is absent throughout the crotch area.

As provided above, the elastomeric material is any material that imparts an elastic-like stretch. The elastomeric material can be comprised of, for example, elastic film, stretch adhesive, lycra, and the likes. In a preferred embodiment, the elastomeric material 420 is a stretch adhesive, such as Conforma 9534-62-1 available from H. B. Fuller Company in Vadnais Heights, Minnesota. By using stretch adhesive the absorbent article 410 can be manufactured in the machine direction while providing stretch in the cross-direction (CD direction). See e.g. FIG.

Figure 39:
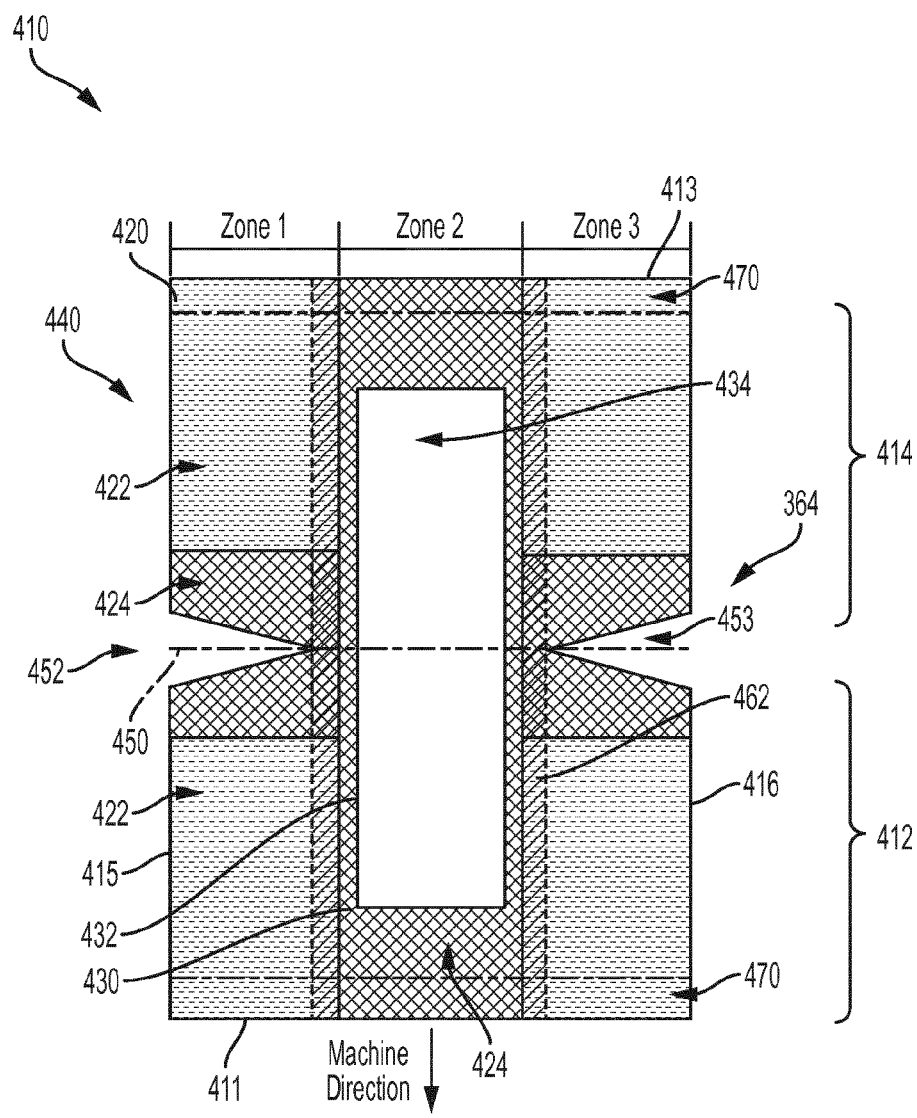
FIG. 39 is a top plan view of absorbent article in accordance with another embodiment of the present disclosure wherein elastomeric material is both sprayed and slot coated on the substrate.

The elastomeric material 420 can include one or both of breathable regions and fluid-impervious regions (referring also to those regions not completely fluid-impervious, but still intended to prevent fluid from passing through). In some embodiments, all of the elastomeric material is breathable. In other embodiments, all of the elastomeric material is fluid-impervious. In other embodiments, the elastomeric material 420 includes at least one breathable region and at least one fluid-impervious region. In one aspect, the breathable regions 422 are provided by spraying the elastomeric material on the substrate layer(s) and the fluid-impervious regions 424 are provided by slot-coating the elastomeric material on the substrate layer(s) as shown in FIGS. 36, 37 and 39.

In the embodiment shown in FIG. 33, at least one substrate layer 440 is provided. As shown, the substrate layer 440 extends from the front edge 411 of the article, through the crotch region, and to the rear edge 413 of the article. However, it is to be understood that the front portion 412 and the rear portion 414 can be provided as separate pieces that can be coupled together at their edges to form the absorbent article. An elastomeric material 420 can be provided to the substrate layer 440 to provide an elastomeric composite. In some embodiments, the elastomeric material 420 is one or more of stretch adhesives or stretch films applied to the substrate layer(s) 440, 446 by slot coating, spray application, or the like. In the embodiment shown in FIGS. 34 and 35, the elastomeric material 420 is sprayed on to the substrate 440, such that the entirety of the composite comprises a breathable elastomeric material.

Additionally, for ease of manufacturing and to eliminate waste, slits can be cut into the elastomeric composite to form the leg openings. Because the elastomeric composite extends from the top edge to the bottom edge, such that it includes the waist opening and the leg openings, gasket cuffs are essentially formed that provide a smooth contoured fit with the body of the wearer (including the waist and legs).

Figures 34A, 34B:
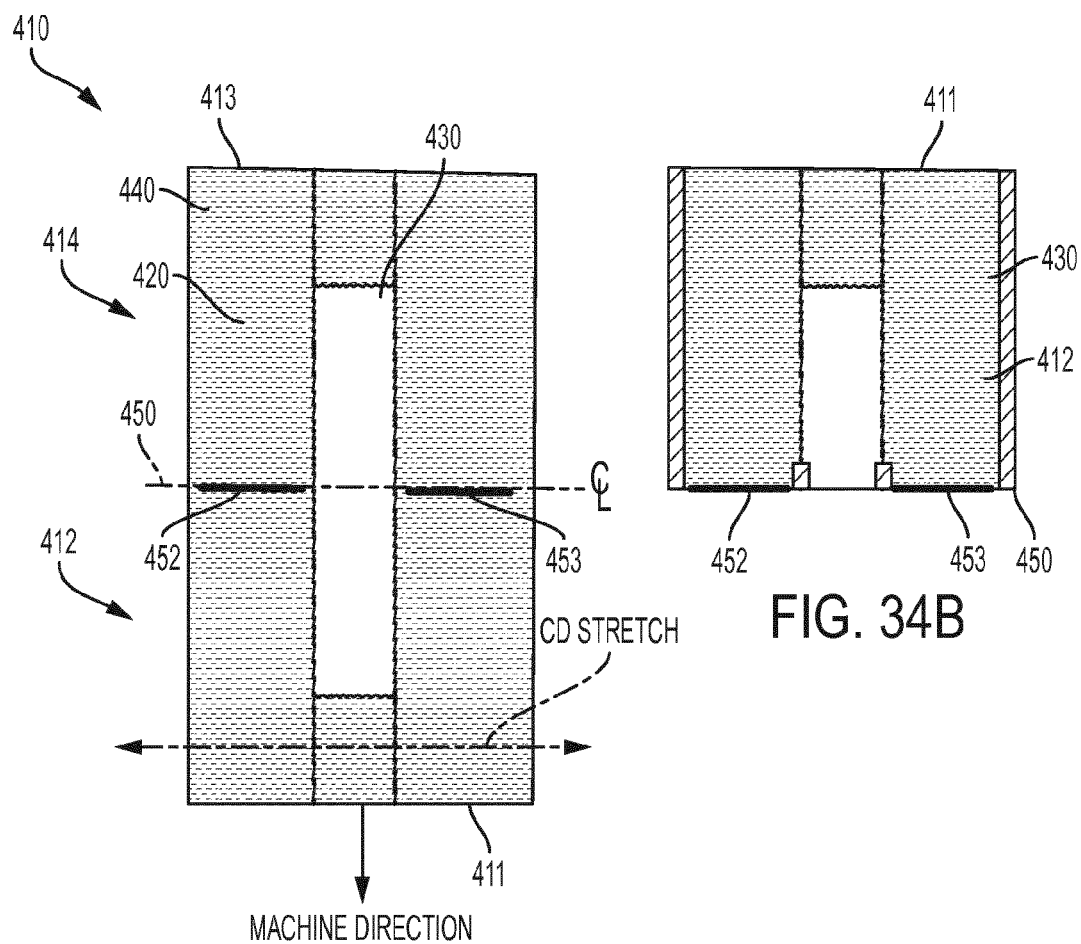

In FIG. 34, the elastomeric material 420 is absent from the crotch portion 430. However, it also is to be understood that the elastomeric material 420 can extend through the crotch portion 430, or can extend through the crotch portion 430 but subsequently be deadened (e.g., crimped or fused in a manner to neutralize elasticity) prior to coupling the absorbent core insert to the absorbent article.

In the embodiments shown in several of the figures, including FIGS. 33-40, the elastomeric composite(s) can be folded at fold line 450 such that the front 412 and rear portions 414 of the absorbent article 410 are aligned and face one another. The front 412 and rear portions 414 can then be sealed at their side edges via seal 466. Additionally, reinforcement couplings 469 can be provided at the inside edges of the leg openings (edges closest to crotch portion 430). As provided previously, it is also to be understood that the front 412 and rear portions 414 can be provided as separate pieces that can be aligned and joined at the sides and along the crotch portion 430 to form the final product.

In the embodiment shown in FIGS. 35A and B, a polymer film layer 438, or "fluid-impervious barrier layer", is coupled to the elastomeric composite along at least the crotch region 430. The absorbent core 434 is then coupled to the polymer film layer 438 in the crotch region 430. Although shown here in the shape of a rectangle, the absorbent core 434 can be provided in any desired shape, such as an ellipse, or an hourglass-like shape. In accordance with the present invention, the polymer film layer 438 and absorbent core 434 are both components of an insert assembly 432, shown and described in more detail with respect to FIGS. 36, 38, and 40. In the embodiment shown in FIG. 35B, once folded, the leg slits are aligned with the trough 431 of the absorbent core (lowest point on the absorbent core when the absorbent article is in the folded configuration). However, it is to be understood that the leg openings 452, 453 can be higher than, lower than, and/or at an angle with respect to the trough 431.

Figure 36A:
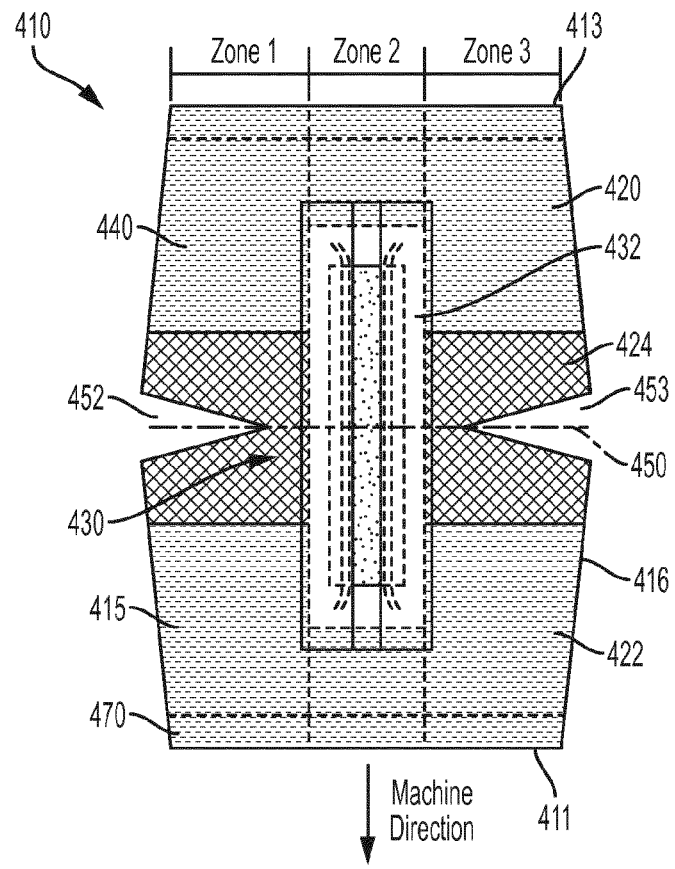
FIG. 36A is a top plan view of an absorbent article in accordance with another embodiment wherein elastomeric material is both sprayed and slot coated on the substrate.
Figure 37:
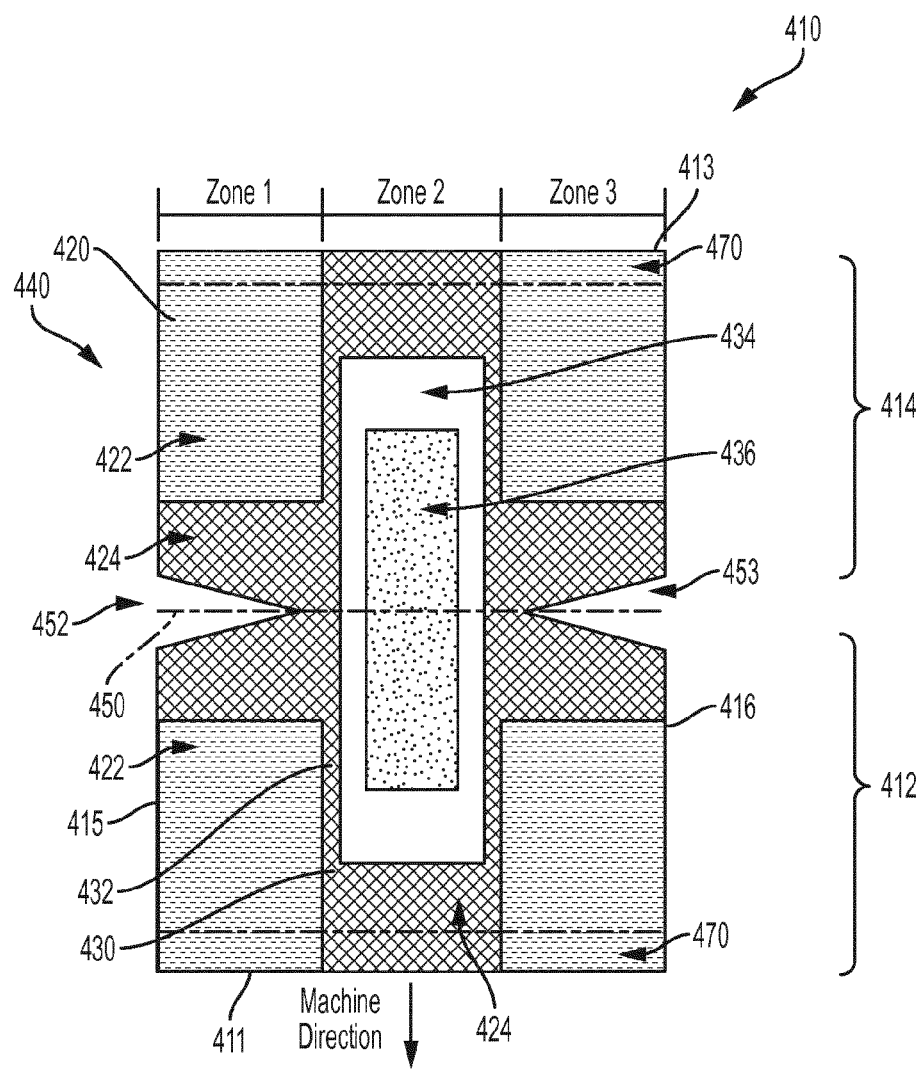
FIG. 37 is a top plan view of an absorbent article in accordance with another embodiment of the present disclosure wherein elastomeric material is both sprayed and slot coated on the substrate.

In some embodiments, as shown in FIG. 36A, the elastomeric material 420 includes at least one breathable region 422 and at least one fluid-impervious region 424. In certain aspects, the fluid-impervious regions 424 are located in areas in which leakage may occur, such as around the leg openings 452 and 453. As shown, a fluid impervious region 424 extends along both of the first and second leg openings 452 and 453. In another aspect, breathable regions 422 extend along the remainder of the substrate, excluding the crotch region, from the waist opening of the absorbent article 410 to the fluid-impervious regions 424 located along the legs openings 452 and 453. In this way, the absorbent article 410 provides the wearer with breathable areas to aid in the wearer's comfort, while also providing leakage protection around the leg openings.

As shown in FIG. 36A, the elastomeric material 420 can be applied in three zones that each run from the front edge 411 to the rear edge 413 of the article 10. In this embodiment, the first and third zones run alongside edges 415 and 416 ("slot & spray" zones; Zones 1 and 3) and the stretch adhesive is intermittently slot coated and sprayed, such that a fluid-impervious region is provided around the leg openings and breathable regions are provided on either side of the fluid-impervious regions. The second zone ("spray zone"; Zone 2) runs down the middle of the absorbent article. As shown, stretch adhesive is intermittently sprayed in this zone, with no elastomeric material 420 sprayed in the absorbent core region. The absence of elastomeric material 420 in the absorbent core area can lead to a cost savings with respect to elastomeric material.

Figure 36B:
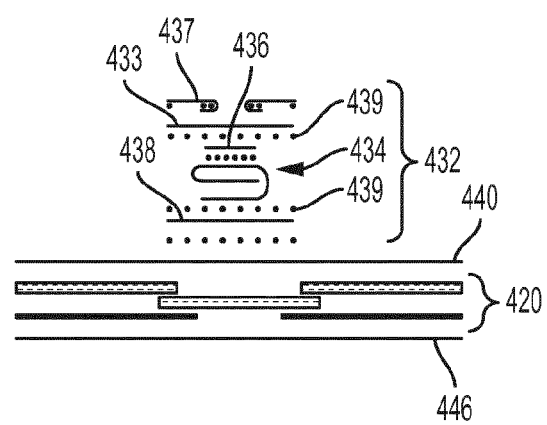
FIG. 36B is an exploded cross sectional view of the absorbent article of FIG. 36A.

The absorbent article 410 also includes an insert assembly 432 that is positioned within the crotch portion 430 and is disposed on top of substrate layer 440. The insert assembly 432 includes stand up leg gatherings (SULG) 437, a top sheet 433, an acquisition layer 436 (or acquisition and distribution layer, "ADL") and an absorbent core 434, with the acquisition layer 436 disposed between the absorbent core 434 and a top sheet 433, as shown in FIG. 36B. The acquisition layer 436 is responsible for distributing fluid across the absorbent core 434 for faster and more even absorbance, and to help provide a sense of dryness to the skin of the wearer. Exemplary acquisition layer materials include, but are not limited to, air bond (TAB) nonwovens, "curly" fibers, perforated plastic film, resin-bonded nonwovens, and "high loft" nonwovens. In one embodiment, the acquisition layer material is a "high loft" nonwoven, such as the ST6CT8H50 high-loft nonwoven (50 gsm) available from Shalag Nonwovens located in Upper Galilee, Israel.

The absorbent core 434 may generally include an absorbent material, a nonabsorbent material, or any combination thereof. Exemplary materials include, but are not limited to, one or more of fluff pulp, airlaid material, super absorbent polymer (SAP), tissue, cotton fibers, rayon viscose, creped tissue, paper towel, and curly fibers. For example, the absorbent core 434 may include a pulpless absorbent core containing SAP, nonwoven and possibly airlaid, which can be constructed in one or more layers. In one embodiment, the absorbent core 434 includes SAP disposed between a high loft non-woven material on top and a Spunlace non-woven material on the bottom. The non-woven material can be an airlaid material, such as VH-460.113 (460 gsm) available from Glatfelter Falkenhagen GmbH located in Pritzwalk, Germany. The airlaid material provides a thin absorbent layer compared to other absorbent materials, which is desirable when designing disposable absorbent articles that look and feel more like non-disposable underwear.

The absorbent core 434 may be comprised of a single ply or multiple plies, such as 2, 3, 4, 5, 6, 7, 8, 9, 10, or more plies. In one embodiment, the absorbent core is a single sheet of material folded to provide multiple plies. For example, as shown in FIG. 36B, the absorbent core 434 is folded to provide three plies. When multiple plies are provided, the plies can all have the same thickness, each ply can have a different thickness, or some plies can have the same thickness while others have different thicknesses. Each ply can have a constant thickness or a variable thickness.

Additionally, the plies can all be made up of the same material or of different materials. Each ply itself can also be made up of more than one material, such that the materials are non-homogeneously distributed. For example, a unitary (single) but non-homogenous absorbent layer or ply can have a portion that comprises fluff without SAP and another portion that comprises fluff with SAP, and optionally another portion that comprises fluff with a different proportion of SAP relative to fluff. A multicore, or ply, design of the absorbent core is discussed in co-pending international application titled "Multi-Core Absorbent Article", having application no. PCT/US2016/012710, and filed Jan. 8, 2016, the content of which is incorporated by reference herein in its entirety. One advantage of folding a thinner absorbent material to form a multi-ply absorbent core is that the supply rolls can last longer on a high speed manufacturing line due to the fact that more material can be wrapped around the core of the roll and while increasing the width of the roll. Specifically, the amount of material that has to be spliced on the machine is reduced, thus, reducing machine downtime and material waste.

Optionally, the insert assembly 432 includes a polymer film layer (e.g. fluid-impervious layer) 438 to provide an additional or alternative fluid-impervious barrier to fluids, especially if elastomeric material 420 is not provided in the crotch portion, or if the elastomeric material 420 provided in the crotch portion does not provide a sufficiently fluid-impervious barrier. When present, the polymer film layer 438 is disposed between the absorbent core 434 and a substrate layer and can optionally be coupled to the absorbent core 434 and the first substrate layer 440 via an adhesive 439. The adhesive can be, but is not limited to, an elastomeric adhesive, or a construction adhesive, such as the Full-Care-5603 olefin adhesive also from H. B. Fuller Company, or stretch adhesive, such as the Full-Care 8500 adhesive.

Exemplary polymer films materials that can be used on the in the polymer film layer include, but are not limited to, polyethylene, polypropylene, polyester, nylon, polyvinyl chloride, and combinations thereof. In one embodiment, the polymer film is a polyethylene/polypropylene (PE/PP) blend, such as 0.55 mil PE/PP Film available from Berry Plastics located in Chippewa Falls, Wisconsin.

In the embodiment shown in FIGS. 36A and B, a top sheet 433 configured to come in contact with the wearer's body is also provided. The top sheet material can be comprised of, for example, nonwoven fibers, such as polypropylene (PP), polyethylene (PE), polyethylene terephthalate (PET), bi-component fibers (PE sheath/PET core or PE sheath/PP core), polyester, cotton, cotton blend, viscose, rayon, etc. or any combination thereof; melt-blown nonwovens; spunlaid nonwovens, such as PP spunbounds and PET spunbounds; melt-blown and spunbound combinations (SM), including spun-melt-spun (SMS); and airlaid paper; or any combinations thereof. In one embodiment, the top sheet 433 is a spunbound material, such as the 12 gsm Polypropylene Spunbound from Berry Plastics in Benson, NC. The top sheet 433 can be coated with a surfactant that imparts hydrophilic qualities to the top sheet, so that fluids can permeate the top sheet 433 and be absorbed by the insert assembly 432.

The top sheet 433 can be coupled to the absorbent article using an adhesive, an ultrasonic bond, or any other means of securely attaching the top sheet to one the absorbent article. The top sheet extends over the absorbent core.

In other embodiments, as shown in FIGS. 37 and 39, the fluid-impervious regions 424 of the elastomeric material 420 are located in several areas in which leakage may occur, in addition to around the leg openings, such as at least part of the waist opening, and where the absorbent core 434 is located, in order to also prevent leakage in these areas. As shown in FIGS. 37 and 39, a fluid impervious region 424 can extend along both of the first and second leg openings 452 and 453, as was shown in FIG. 36. In another aspect, breathable regions 422 can extend along the side edges 415 and 416 from the waist opening of the absorbent article 10 to the fluid-impervious regions 424 located along the legs openings 452 and 453. In this way, as with the embodiment of FIG. 36, the absorbent article provides the wearer with breathable areas to aid in the wearer's comfort, while also providing leakage protection in key areas. In another aspect, two breathable regions 422 and one fluid-impervious region 424 extend along the waist opening, as shown in FIGS. 37 and 39. In yet another aspect, at least one fluid-impervious region 424 extends from the waist opening of the front portion to the waist opening of the back portion and includes the crotch portion. In this way, the fluid-impervious region 424 provides a barrier against leakage in the crotch portion, without the need for the polymer film layer 438, which provides additional cost savings.

As shown in FIGS. 37 and 39, the stretch adhesive is applied in three zones that each run from the front edge 411 to the rear edge 413 of the article 410. In these embodiments, the first and third zones run alongside edges 415 and 416 ("slot & spray" zones; Zones 1 and 3) wherein the stretch adhesive is intermittently slot coated on first substrate layer 440 (or the halfs 440a and 440b of the first substrate layer 440 when a top sheet is present, as disclosed in more detail below), within the leg opening areas 452 and 453, and is sprayed in either an intermittent or continuous pattern on the second substrate layer 446. It is to be understood that the spray and slot coat sections can overlap one another given that the application nozzles are not in contact with the substrate layers. In the second zone ("slot zone"; Zone 2) located in between the first and third zones, one option would be to apply the stretch adhesive in a continuous slot coat pattern on the first 440 and second 446 substrate layers, as shown in FIGS. 37-40. Another option would be to slot coat or spray the stretch adhesive in an intermittent pattern, such as to avoid the areas that will be in contact with the absorbent core. The latter option is a more cost effective option if an additional or different fluid impervious barrier layer with respect to the fluid-impervious region 422 produced by application of the elastomeric material 420 needs to be added to the absorbent article 410.

As compared to the embodiment shown in FIG. 36 wherein the insert assembly 432 is coupled to the top of the first substrate layer 440, the insert assembly 432 of the embodiments in FIGS. 37-40 is disposed between two substrate layers 440 and 446, each of which is coupled with a first or second elastomeric material 420a and 420b to form two elastomeric composites. For example, a first elastomeric material 420a is coupled to the first substrate layer 440 to form a first elastomeric composite and a second elastomeric material 420b is coupled to the second substrate layer 446 to form a second elastomeric composite, each of the first and second elastomeric materials having one or more of breathable and fluid-impervious regions. In this way, with the insert assembly 432 disposed between two elastomeric composites, the absorbent article forms a unitized elastomeric panel having a smooth contoured feel on the inside of the absorbent article facing the wearer, while also having a smooth contoured appearance from the outside.

Figure 38:
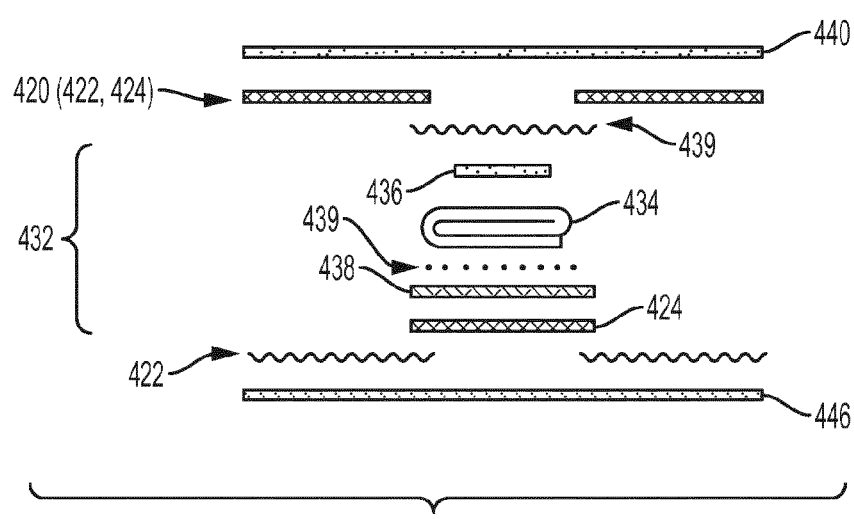
FIG. 38 is an exploded cross-sectional view of the absorbent undergarment of FIG. 37.

In the embodiment of FIGS. 37 and 38, the insert assembly 432 includes an acquisition layer 436 (or acquisition and distribution layer, "ADL") and an absorbent core 434, with the acquisition layer 436 disposed between the absorbent core 434 and the first substrate layer 440. As shown in FIG. 38, the absorbent core 434 is folded to provide three plies. Optionally, the insert assembly 432 includes a polymer film layer 438 to provide an additional or alternative fluid-impervious barrier to fluids, especially if the elastomeric material 420 in the insert assembly 432 region does not provide a sufficiently fluid-impervious barrier. When present, the polymer film layer 438 is disposed between the absorbent core 434 and the second substrate layer 446 and can optionally be coupled to the absorbent core 434 via an adhesive 439. The adhesive can be, but is not limited to, an elastomeric adhesive, or a construction adhesive, such as the 5-5603 olefin adhesive also from H. B. Fuller Company.

The polymer film layer 438 can be coupled to the second substrate layer 446 via the elastomeric material 420 or a separate adhesive, such as a construction adhesive. In one embodiment, when the elastomeric material 420 is used to couple the polymer film layer 438 to the second substrate layer 446, the polymer film layer 438 is cut and placed between the absorbent core 34 and the second elastomeric material 420b, with construction adhesive used to adhere the polymer film layer 438 to the core 434. In another embodiment (not shown), construction adhesive is applied (via, e.g., spraying or slot coating) on the second substrate layer 446 in the area in which the polymer film will be placed in order to couple the polymer film layer 438 to the second substrate layer 446. The second elastomeric material 420b can then be applied (via, e.g., spraying or slot coating) to the second substrate layer 446 in the areas in which the polymer film layer 438 is not coupled to the second substrate layer 446 in, for example, the "slot zone" as described above.

Figure 40:
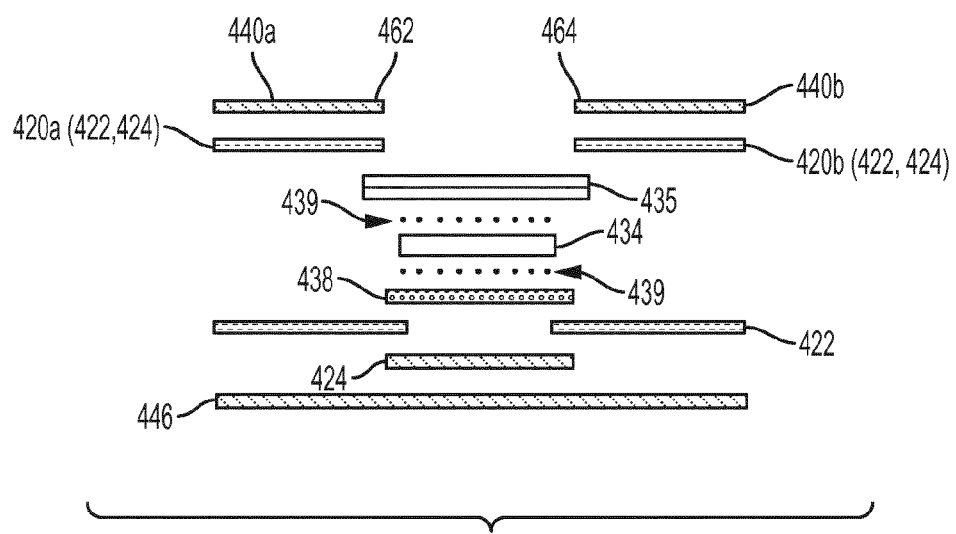
FIG. 40 is an exploded cross-sectional view of the absorbent undergarment of FIG. 39.

In embodiments in which the insert assembly 432 is disposed between two elastomeric composites, the insert assembly 432 can also include a top sheet 433, with the top sheet 433 configured to come in contact with the wearer's body, as shown in FIG. 40. In one aspect, the top sheet 433 can be combined with the acquisition layer 436, as shown in FIG. 40, to form a combined top sheet/acquisition layer 435, such as the Multitex Water Holding Nonwoven—Code TA02T60 (60 gsm) from Texsus Textile & Chemical Nonwoven located in Pistoia, Italy. In one embodiment, the combined layer 435 is formed by subjecting each of the top sheet 433 and the acquisition layer 436 to a mechanical deformation while being combined. In the combined top sheet/acquisition layer 435, the top sheet 433 faces the body of the wearer, while the acquisition layer 436 faces away from the wearer and toward the second substrate layer 446.

In one aspect, the top sheet 433 is coupled to the first elastomeric material 420a, and in turn the first substrate layer 440, along the side edges of the top sheet. In one embodiment, neither the first elastomeric material 420a nor the first substrate layer 440 extends across the entirety of the top sheet 433, as shown in FIG. 40. In one aspect, the first substrate layer 440 is slit in half and separated to form two halves, 440a and 440b, such that one half is provided on each side of the top sheet 433. In another aspect, either or both the first elastomeric material 420a and the first substrate layer 440 extend across the entirety of the top sheet 433.

The top sheet 433, first elastomeric material 420a, and first substrate layer 440 can be coupled to each other using the elastomeric material 420 itself, a separate adhesive, an ultrasonic bond, or any other means of securely attaching the three components to one another. In one embodiment, the top sheet 433 is coupled to the first substrate layer 440, 440a, and/or 440b, using an ultrasonic bond 462 and 464, as shown in FIGS. 39 and 40. The ultrasonic bonds 462 and 464 extend along at least a portion of each of the side edges of the top sheet 433 and the inside edges of the first substrate layer halfs 440a and 440b. For example, the ultrasonic bond can extend along about 20%, 30%, 40%, 50%, 60%, 70%, 80%, 90%. 100%, and any percentage in between, of the edges. In one embodiment, the ultrasonic bonds 462 and 464 extend along the entirety of the side edges of the top sheet 433 and the first substrate layer halfs 440a and 440b, as shown in FIG. 39.

Figure 41A:
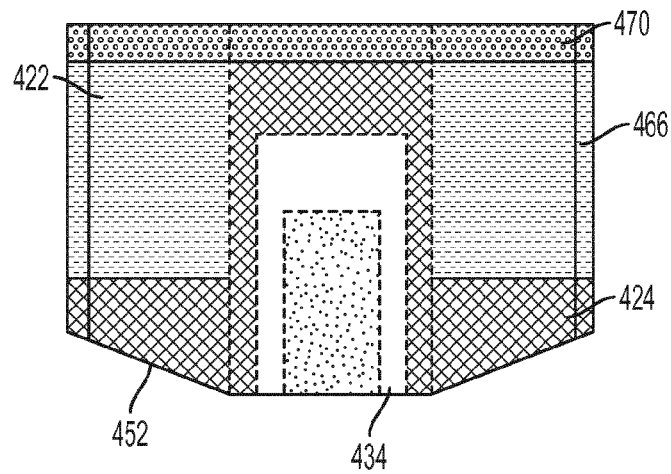
FIG. 41A is a front view of the absorbent undergarment of FIGS. 37 and 38 in a folded and sealed configuration.
Figure 41B:
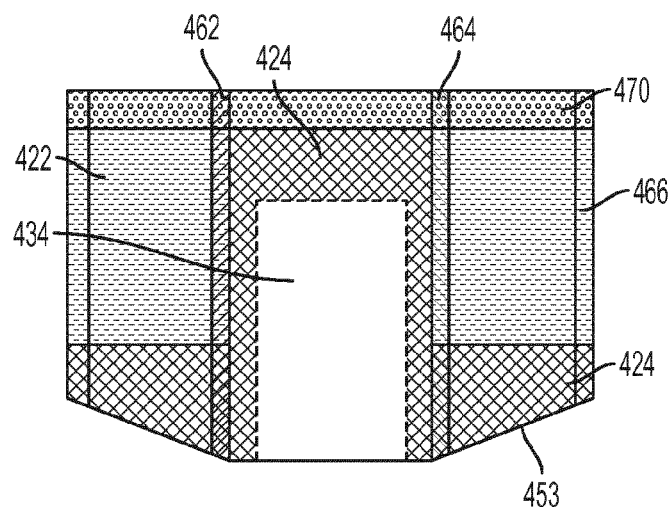
FIG. 41B is a front view of the absorbent undergarments of FIGS. 39 and 40 in a folded and sealed configuration.

The absorbent article 410, in accordance with certain embodiments of the present disclosure, is to be folded such that the top 411 and bottom 413 edges of the article 410 are aligned with one another at the waistband assembly 470, and the first substrate layer 440 (e.g. the substrate layer facing the body of the wearer) on the front portion 12 faces the same first substrate layer 440 on the back portion 414, as shown in FIGS. 41A and B. A seal 466 is to be provided along the side edges. The seal 466 can created through, for example, bonding (e.g., ultrasonic or thermal bonding), adhesive, or any other manner for creating a bond.

In some embodiments, as described previously, leg openings 452 and 453 are provided along the fold point 450. In one embodiment, the leg openings 452 and 453 are two straight slits on the fold line, as shown in FIGS. 33-35. When the front and rear portions are provided in separate pieces, the leg openings can be provided along the bottom edges, when the portions are joined to each other. The leg openings 452 and 453 can be cut in any design desired. For example and not limitation, FIGS. 42A-D provide exemplary designs, such as a straight line (A), a sinusoidal pattern (B), a dual sinusoidal pattern (C), an oval or marquise shape (D), a zigzag pattern (not shown), etc. In another embodiment, the leg openings can be provided at the two side edges 415 and 416 along the fold line via notches, as shown in FIGS. 36, 37 and 39, to provide for angled leg openings (see also FIGS. 41A and B).

Figure 43A:
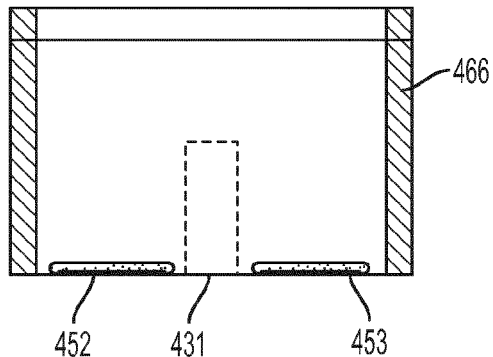
FIGS. 43A-D depict various exemplary configurations for the folded absorbent articles in accordance with the present disclosure.
Figure 43B:
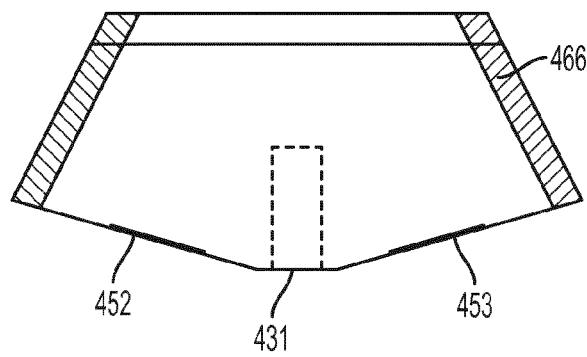
Figure 43C:
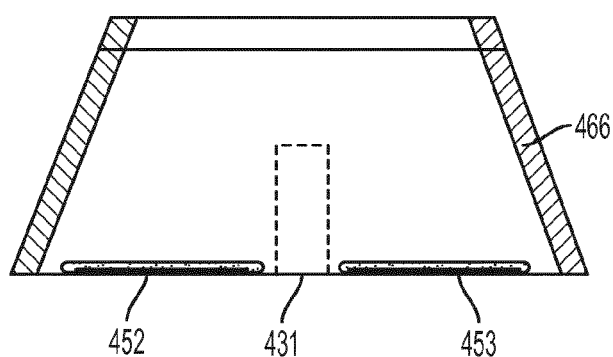
Figure 43D:
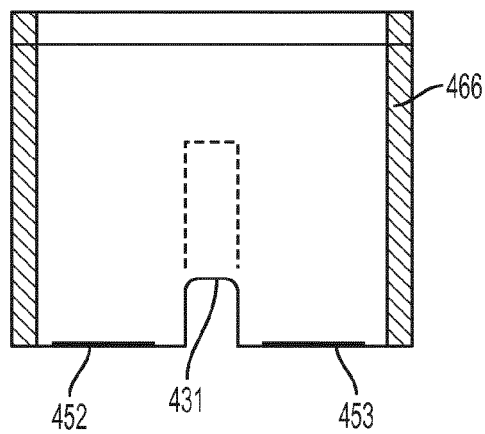

Side edges 415 and 416 can be at any angle with respect to one another or comprise any configuration with respect to the final product configuration. For example, FIGS. 43A-D depict various final product configurations, with the placement of the absorbent core indicated by the dotted lines. For example, in FIGS. 43A and D, side edges 415 and 416 are parallel to one another. In other embodiments, the side edges can be cut such that the edges are at an angle with respect to each other. For example, the edges can taper from the leg openings to the waist openings (e.g., from the top and bottom edges at the waist opening to the fold line), as shown in FIGS. 43B and C. In addition to tapering, the leg openings 452 and 453 can be angled from the interior edges to the exterior edges, as shown in FIG. 43B. The leg openings and side edges can also extend below the trough 431 of the absorbent core, as shown in FIG. 43D. In another embodiment, the leg openings and side edges can extend down to and are in line with the trough 431, as shown in FIGS. 43A and C. In another embodiment, the side edges can extend to a point above the trough 431, while the leg openings are at an angle with respect to the trough 431, as shown in FIG. 43C.

Figure 44A:
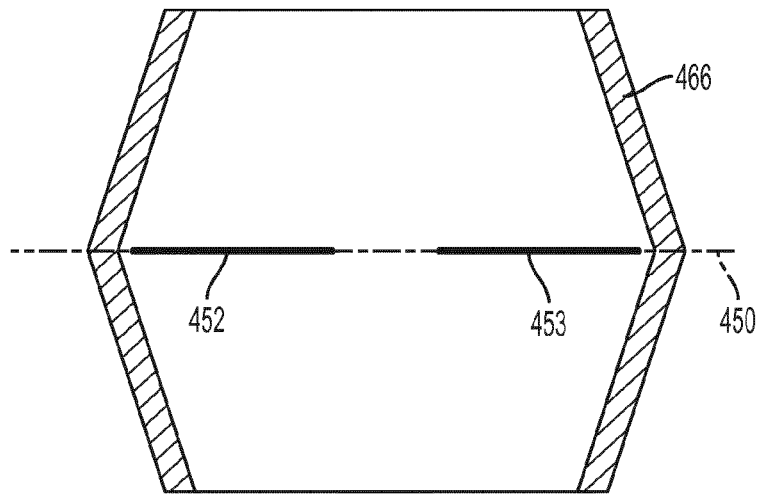
FIGS. 44A and B depict an exemplary configuration for an absorbent article of the configuration shown in FIG. 43C, shown both laid open (A) and folded (B).
Figure 44B:
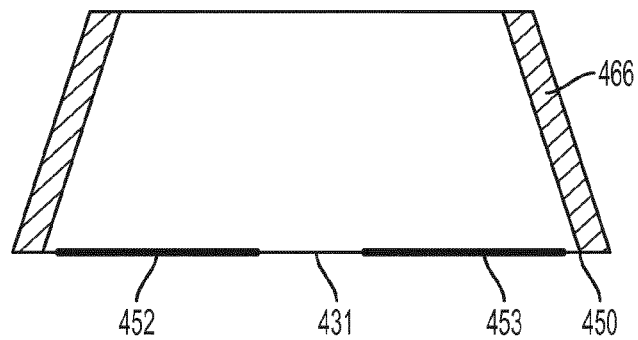

With respect to the embodiment shown in FIG. 43C, FIG. 44A depicts the absorbent article laid flat before it is folded, with the side edges tapering from the leg slits to the waist opening, while FIG. 45B depicts the article in a folded configuration. It is to be understood that these examples are non-limiting and that the side edges can be cut into any configuration, such as a curved, or other, configuration.

Figure 45:
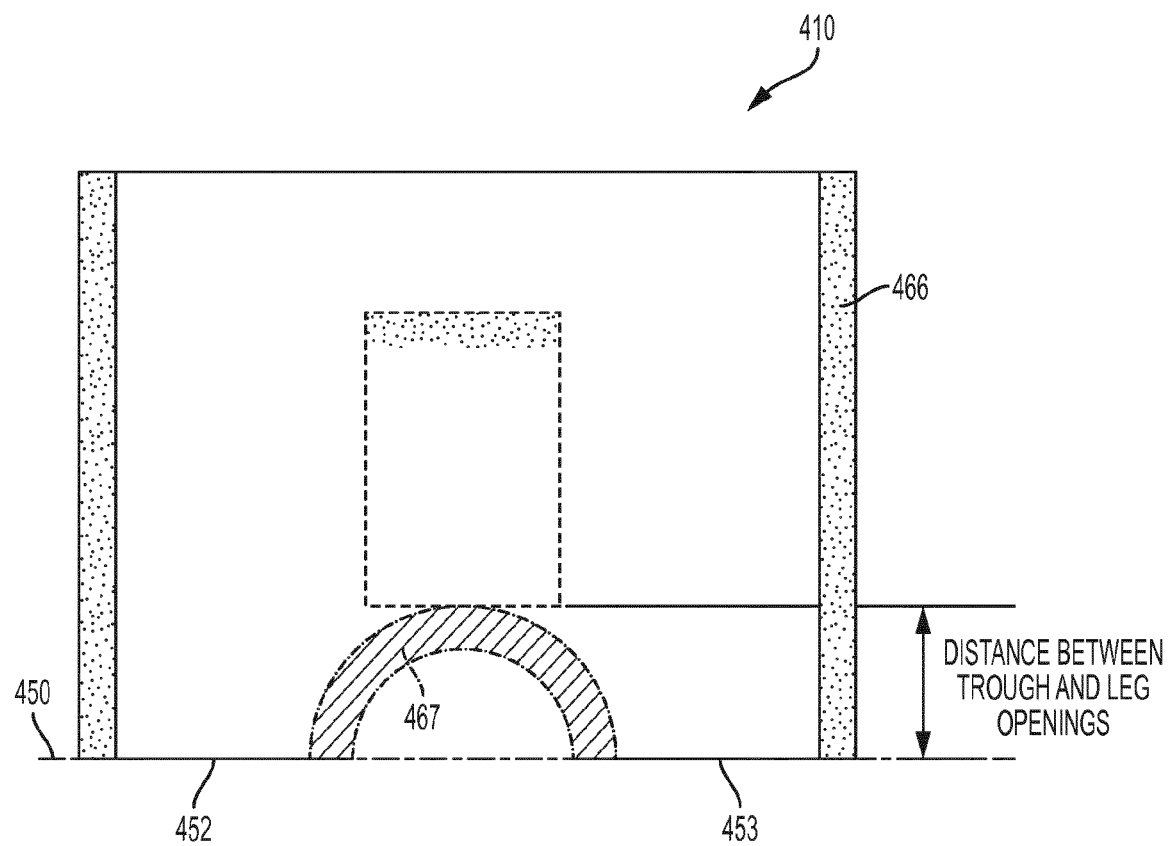
FIG. 45 is a top plan view of the configuration shown in FIG. 431), illustrating points at which the absorbent article is sealed when folded.

With respect to the embodiment shown in FIG. 43D, FIG. 45 illustrating the points at which the absorbent article is sealed when folded. For example, the absorbent article is sealed along the side edges (seal 466), as provided previously. Additionally, because the leg openings 452 and 453 are located below the trough 431 of the absorbent core, a hole must be cut and the resultant edges must be sealed between the leg openings and crotch area, as shown, via seal 467.

In accordance with the present disclosure, absorbent articles include a waistband assembly. The waistband assembly 470 can include any number of options that provides for a tight fit and seal with the wearer's body. In one embodiment, the waistband assembly 470 includes the crimping and/or stamping of the front 411 and rear edges 413, such as by intermittent and spaced crimps and/or punches applied with pressure and heat. In this way, a seam is provided to the waist opening. The spacing between the crimps and/or punches allows the elastomeric panel to maintain its elasticity and permits the absorbent article to maintain smooth, continuous contact with the body, including the waist openings.

Figure 46B:
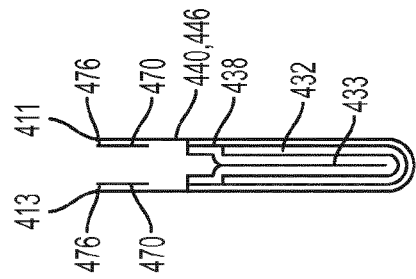
FIG. 46B is a cross-sectional side view of the absorbent article in FIG. 46A, shown in the folded configuration.
Figure 46A:
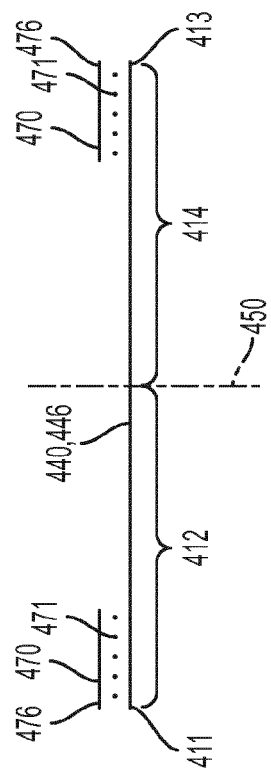
FIG. 46A is a longitudinal cross-sectional view of an absorbent article in the laid open configuration having a separate waistband assembly according to one embodiment.

In other embodiments, a separate waistband assembly 470 can be added. The waistband assembly can be added at the waist opening and coupled to the front and/or rear edges. The separate waistband can be coupled to the edges via an adhesive or bonding 471, such as thermal or ultrasonic bonding. In one embodiment, as shown in FIGS. 46A and B, the waistband assembly is provided to both the front 411 and rear 413 edges such that the front 411 and rear 413 edges are substantially aligned with the outside edge 476 of the waistband assembly 470. In this embodiment, the waistband assembly is not folded over the front 411 and/or rear 413 edges. It is also to be understood that the outside edge 476 of the waistband assembly 470 can extend beyond the front and rear edges or the front 411 and rear 413 edges can extend beyond the outside edge 476, for example, by about 1%, 2%, 3%, 4%, 5%, 6%, 7%, 8%, 9%, 10%, 15%, 20%, 25%, 30%, or more, or by any integer there between. FIG. 46A depicts a longitudinal cross-sectional view of the absorbent article 410 in the laid-open unfolded configuration, while FIG. 46B shows a cross sectional side view of the absorbent article 410 in the folded configuration.

Figure 47C:
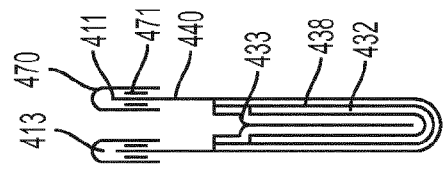
FIG. 47C is a cross-sectional side view of the absorbent article in FIG. 4613.
Figure 47B:
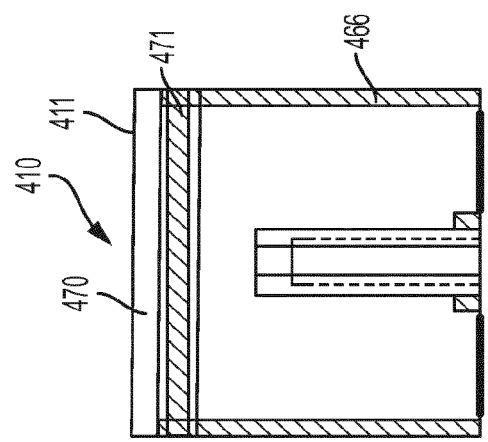
FIGS. 47A and B are top plan views of an absorbent article in the laid open (A) and folded (B) configurations having a separate waistband assembly according to a second embodiment.
Figure 47A:
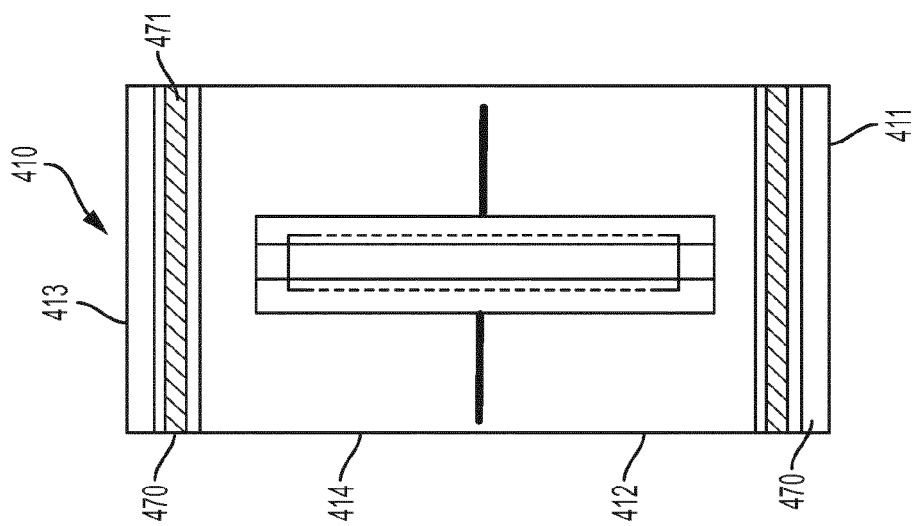

In another embodiment, as shown in FIGS. 47A-C, a separate waistband assembly 470 is provided to, and folded over, the front 411 and the rear edges 413. FIG. 47C shows a cross section side view of a folded absorbent article further illustrating this configuration. As can be seen, the waistband assembly 470 is folded over the edges 411 and 413 and coupled to the elastomeric composite on both sides via bonds 471.

Figure 48A:
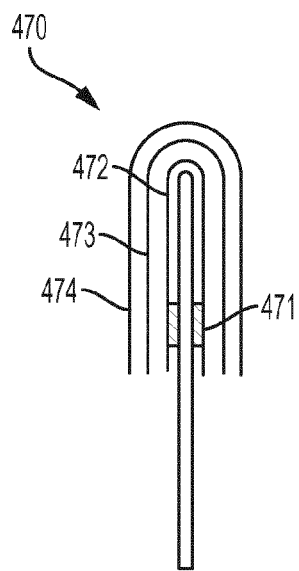
FIGS. 48A-C are cross-sectional side views of exemplary separate waistband assemblies consistent with the present disclosure.
Figure 48B:
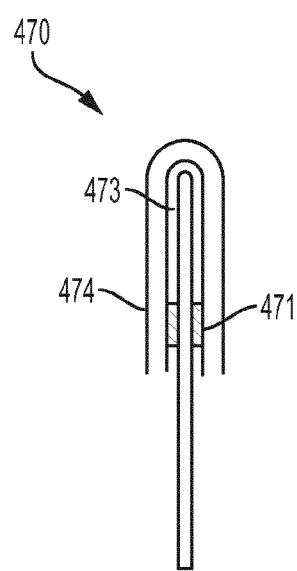

The waistband assembly 470 can comprise any number of layers and materials. For example, the waistband assembly 470 can comprise 1, 2, 3, 4, or 5 layers. It is to be understood that the number of layers, as described herein, refers to the number of layers prior to folding and bonding the waistband assembly over and to the electromeric composite (e.g., substrate layer(s) with elastomeric material applied thereto). Each layer can comprise a different material, all of the layers can comprise the same material, or some can comprise a different material and some can comprise the same material. In one embodiment, the waistband assembly 470 can comprise three layers, each layer comprising the same material. In another embodiment, the waistband assembly 470 can comprise three layers, with two layers the same and one different. In one example, as shown in FIG. 48A, the waistband assembly 470 comprises three layers—two nonwoven layers 472, and 474 and an elastic material layer 473 sandwiched in between the nonwoven layers. The elastic material 473 is first bonded or adhered to both of the nonwoven layers 472 and 474. Then all three materials (472, 473, 474) are folded over and coupled (e.g., bonded, adhered, etc.) to the front 411 and rear 413 edges of the elastomeric composite, with the inside non-woven layer 472 being the closest layer to the elastomeric composite.

In another embodiment, the waistband assembly 470 can comprise two layers, each layer comprising the same material. Or, the waistband assembly 470 can comprise two layers, each layer comprising a different material. In an example, as shown in FIG. 4813, the waistband assembly 470 comprises two layers—an elastic material layer 473 on the inside and a nonwoven layer 474 on the outside, the inside layer 473 bonded to the electromeric composite. The elastic material layer can comprise any material that imparts an elastic-like stretch, such as an elastic film, a stretch adhesive.

Figure 48C:
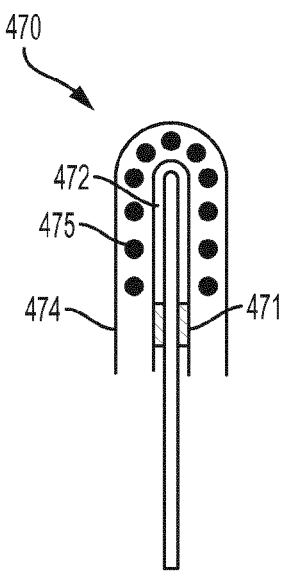

In yet another example, as shown in FIG. 48C, the waistband assembly 470 comprises two nonwoven layers 472 and 474 with elastic strands 475 disposed between the layers. The elastic strands 475 are bonded or adhered between the two nonwoven layers 472 and 474 while under elastic tension, and applied transverse to the machine direction (e.g., in the CD direction). Subsequent to bonding or adhering the elastic strands, the waistband assembly 470 is folded over and coupled (e.g., bonded, adhered, etc.) to the front 411 and rear 413 edges of the elastomeric composite.

Figure 49A:
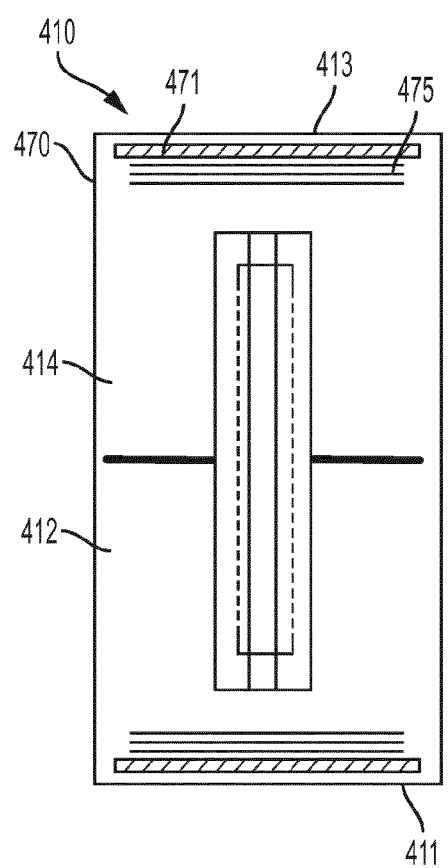
FIGS. 49A and B are top plan views of an absorbent article in the laid open (A) and folded (B) configurations having a separate waistband assembly according to a third embodiment.
Figure 49B:
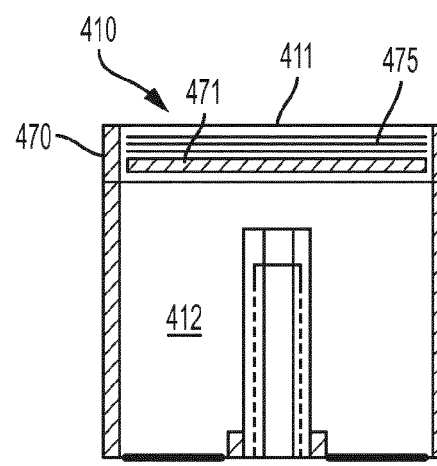
FIG. 49C is a cross-sectional side view of the absorbent article in FIG. 49B.
Figure 49C:
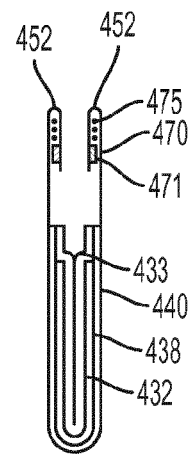

In another embodiment, the waistband assembly 470 is formed from folding over the front 411 and/or rear 413 edges of the absorbent article at fold lines 452 and 454, as shown in FIGS. 49A-C. The folded edges are coupled to the face of the substrate using any mechanism known in the art, such as adhesive (e.g., construction or stretch adhesive) or bonding (e.g., ultrasonic or thermal bonding). Furthermore, elastic strands 473 can be disposed within the waistband assembly 470, as shown in FIGS. 49A and B. For example, the elastic strands 473 can be coupled to the elastomeric composite toward the front and/or rear edges of the absorbent article, such that the elastic strands 473 are disposed between the fold lines 452 and 454 and the bond 471 (e.g., seal, adhesive) once the edges are folded over and coupled to the composite. An example of this can be seen in FIG. 49B which shows a front plan view of the folded waistband assembly, and FIG. 49C, which shows a cross-sectional side view of a folded absorbent article having this embodiment.

Figure 50A:
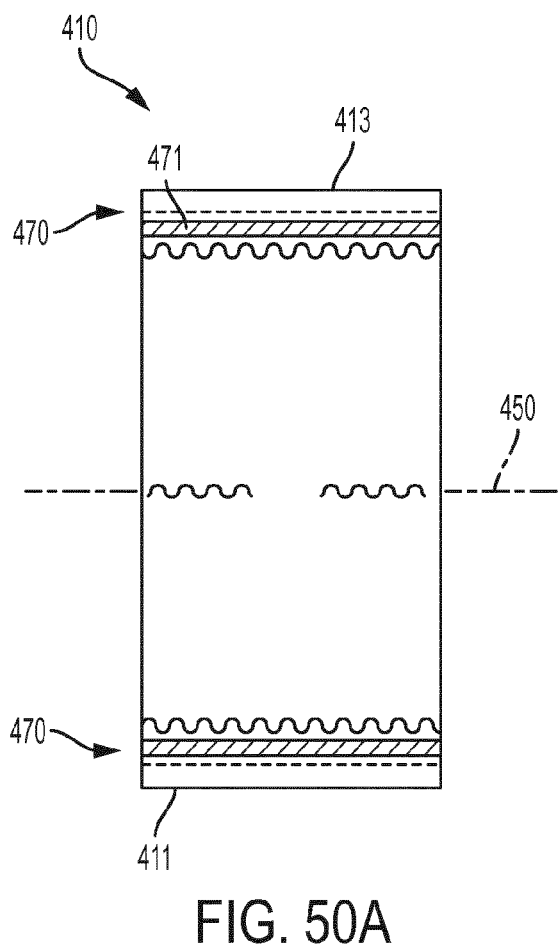
FIG. 50A is a top plan view of an absorbent article in the laid open configuration having a waistband assembly cut in a sinusoidal pattern, with the pattern facing the leg openings.
Figure 50B:
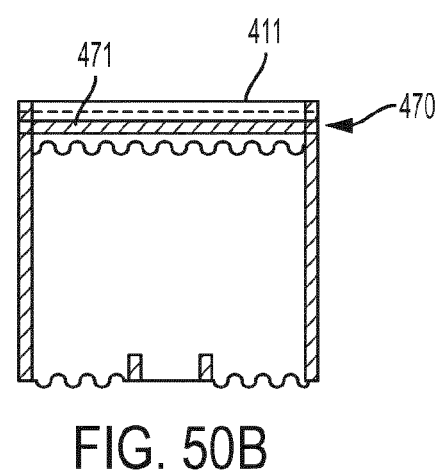
FIG. 50B is a top plan view of the absorbent article of FIG. 50A in the folded configuration.
Figure 50C:
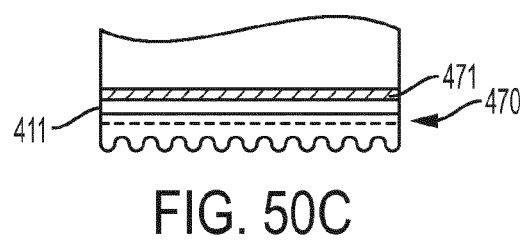
FIG. 50C, is a top plan view of a section of the bottom edge of an absorbent article in the laid open configuration having a waistband assembly cut in a sinusoidal pattern, with the pattern facing away from the leg openings.

Although shown as straight lines in FIGS. 47 and 49, the waistband assembly 470 can be cut in any design. For example, the waistband assembly 470 can be cut in a sinusoidal pattern to provide a scalloped look, or in a zig-zag pattern. FIGS. 50A and B depict the waistband cut in a sinusoidal pattern, such that the sinusoid shape faces the leg openings. Alternatively, FIG. 50C depicts the sinusoid shape facing away from the leg openings at the end of the waistband assembly at the front end 411 when the absorbent article is in the laid-open configuration before being folded.

Figure 51:
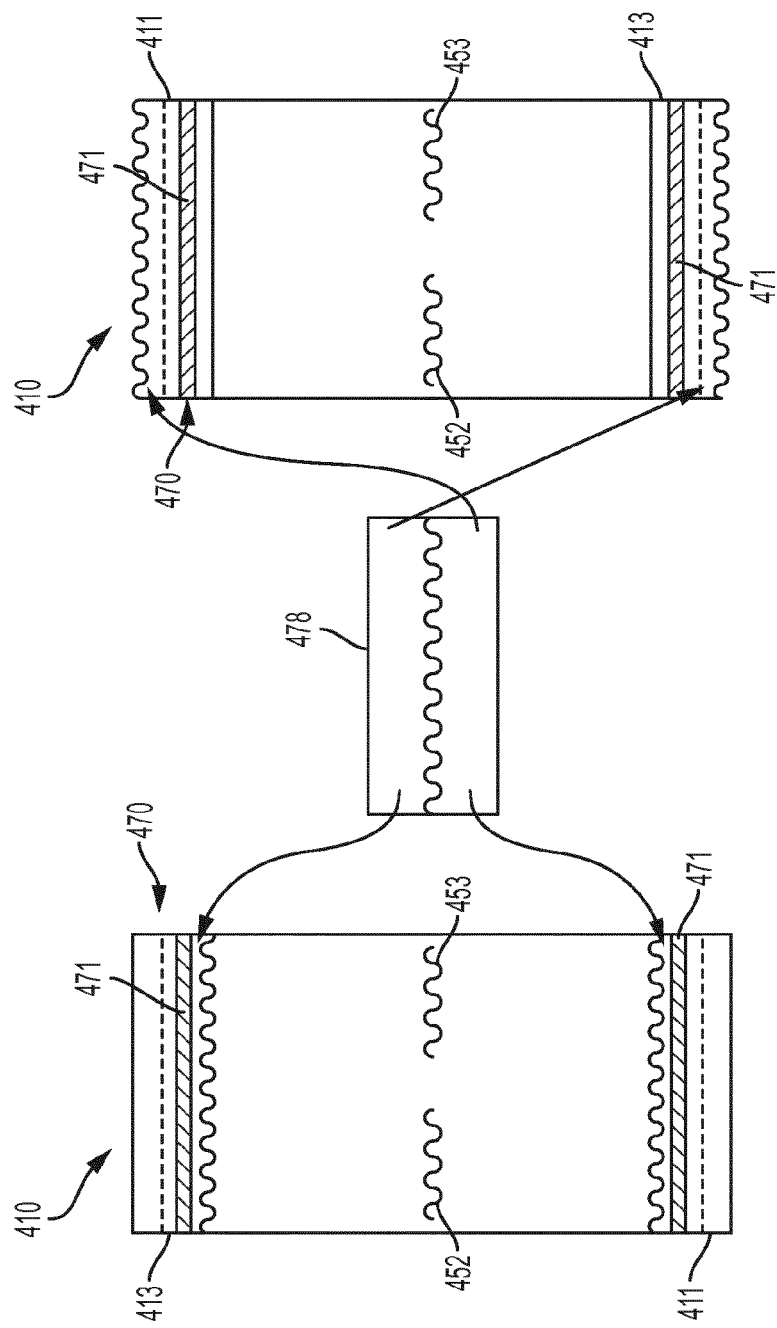
FIG. 51 is a schematic representation of a separate waistband assembly illustrating a method for cutting and attached the assembly to the absorbent article to provide a sinusoidal pattern facing the leg openings (left) and a pattern facing away from the leg openings (right).

For those embodiments in which the edges are folded over to provide the waistband assembly 470, the edge can be cut with the desired pattern before being folded over. For those embodiments in which the waistband assembly 470 is provided as a separate material 478, the material 478 is first cut and then placed on the edges of the absorbent article, such that the cut edge either faces toward the leg openings or away from the leg openings. FIG. 51 displays two embodiments for adding a separate waistband assembly 470 having a sinusoidal cut configuration. As can be seen, a separate web containing the waistband material 478 is provided, the web is cut and then the pieces are placed on the edges 411 and 413 of the absorbent article 410. The cut as shown in FIG. 51 is a sinusoidal cut but can be any configuration, such as scalloped or zigzag, saw tooth, etc. The left side of the unfolded absorbent article shown in FIG. 51 depicts the sinusoidal shape facing toward the leg openings 452 and 453, while the right side of FIG. 51 depicts the sinusoidal shape facing away from the leg openings 452 and 453. As shown, the waistband assembly 470 is coupled to the absorbent article via seals 471. The waistband assembly 470 can include any one or combination of non-woven material, laminate elastic film, stretch adhesive, elastic strands, or the likes.

There are several methods by which the absorbent articles 410 of the present disclosure can be manufactured. For example, FIGS. 52-56 depict processes for manufacturing an absorbent article, wherein the absorbent core is provided on top of the elastomeric composite, rather than between two separate elastomeric composites.

Figure 52:
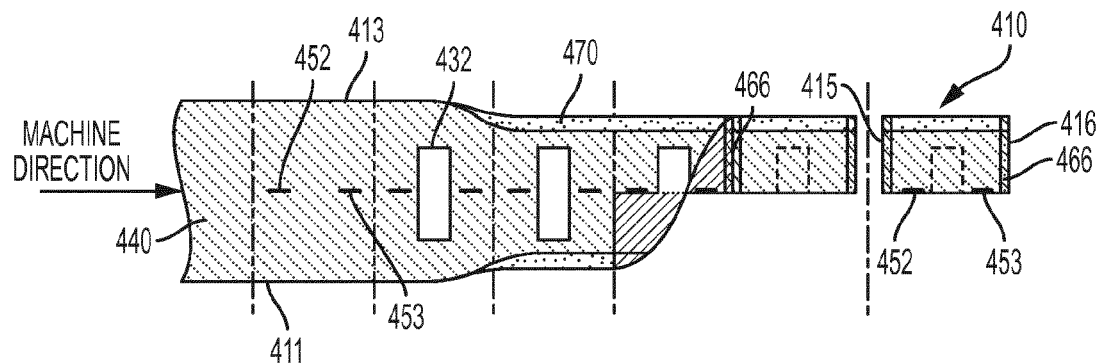
FIG. 52 is a schematic representation of a first exemplary method for manufacturing an absorbent article in accordance with the present disclosure.

As shown in FIG. 52, the elastomeric composite web is provided such that the longitudinal axis of the absorbent article that runs from the front edge 411 of the article through the length of the absorbent core and to the rear edge 413 of the article is transverse to the machine direction of the web. As the web travels down the line, the leg slits 452 and 453 are first cut into the composite web. Then the insert assembly 432 is cut and placed onto the elastic composite web, wherein the assembly 432 is coupled to the composite web. Coupling, as referred to herein, includes bonding, such as ultrasonic or heat bonding, adhering, such as through an adhesive, and any other manner for attaching components to one another known in the art. As shown, once the insert assembly 432 is coupled to the composite web, the composite web can be folded along its top edge and bottom edge to form a waistband assembly 470. Prior to folding, elastic strands can be provided to the composite web toward the top edge and the bottom edge (not shown), such that the elastic strands are completely encompassed by the waistband assembly 470 once folded over. Alternatively (not shown), a separate waistband piece 478 can be provided to the top edge and the bottom edge to form the waistband assembly 470. Once the waistband is folded over, the product can be folded in half, such that the front edge 411 and the rear edge 413 are aligned. The side edges 415 and 416 are then sealed together through, for example, bonding 466 (e.g., ultrasonic or thermal bonding). Once the edges are sealed, the product can be cut to provide discrete absorbent articles.

Although not shown, it is to be understood that in embodiments wherein two elastomeric composites are to be combined to provide a unitized elastomeric panel, a second elastomeric composite web can be provided, which can be centered and aligned with the first web after the absorbent core is coupled to the first web, after which leg slits can be cut. It is also to be understood that the present invention also includes disposable articles having an elastomeric material disposed between two substrate layers without an absorbent core.

Figure 53:
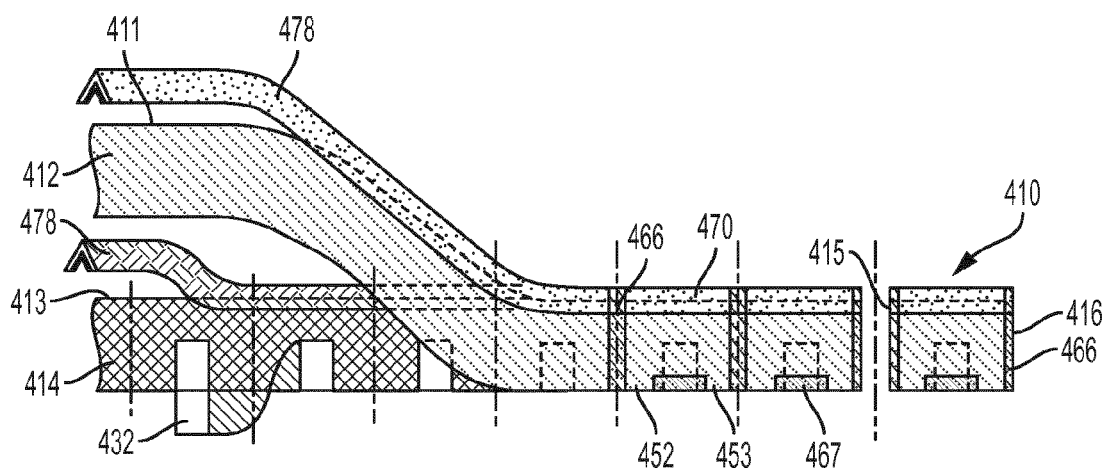
FIG. 53 is a schematic representation of a second exemplary method for manufacturing an absorbent article in accordance with the present disclosure.

In another embodiment, as shown in FIG. 53, the front portion 412 and the rear portion 414 of the absorbent article 410 are initially provided as separate pieces, such that there is a front elastic composite web and a rear elastic composite web. The elastomeric composite webs are provided such that the longitudinal axis of the absorbent article 410 that runs from the top front edge 411 of the article through the length of the absorbent core and to the rear edge 413 of the article is transverse to the machine direction of the web. As the webs travel down the manufacturing line, half of the insert assembly 432 is coupled to the rear elastic composite web. At this time, the waistband can be added to/folded over the rear edge 413 of the rear elastic composite web. The half of the insert assembly 432 not coupled to the rear elastomeric composite web is then folded on top of the other half. Next the front elastomeric composite web is aligned and coupled to the other half of the insert assembly 432. In order to secure the two elastomeric webs to each other to form the final product, seals 466, such as ultrasonic or heat seals, are provided along the side edges 415 and 416, as well as in the crotch area, while making sure to leave the leg openings 452 and 453 unsealed. Once the side edges 415 and 416 and bottom edges in the crotch area are sealed via seals 466 and 467, the product can be cut to provide discrete absorbent articles 410.

Figure 54:
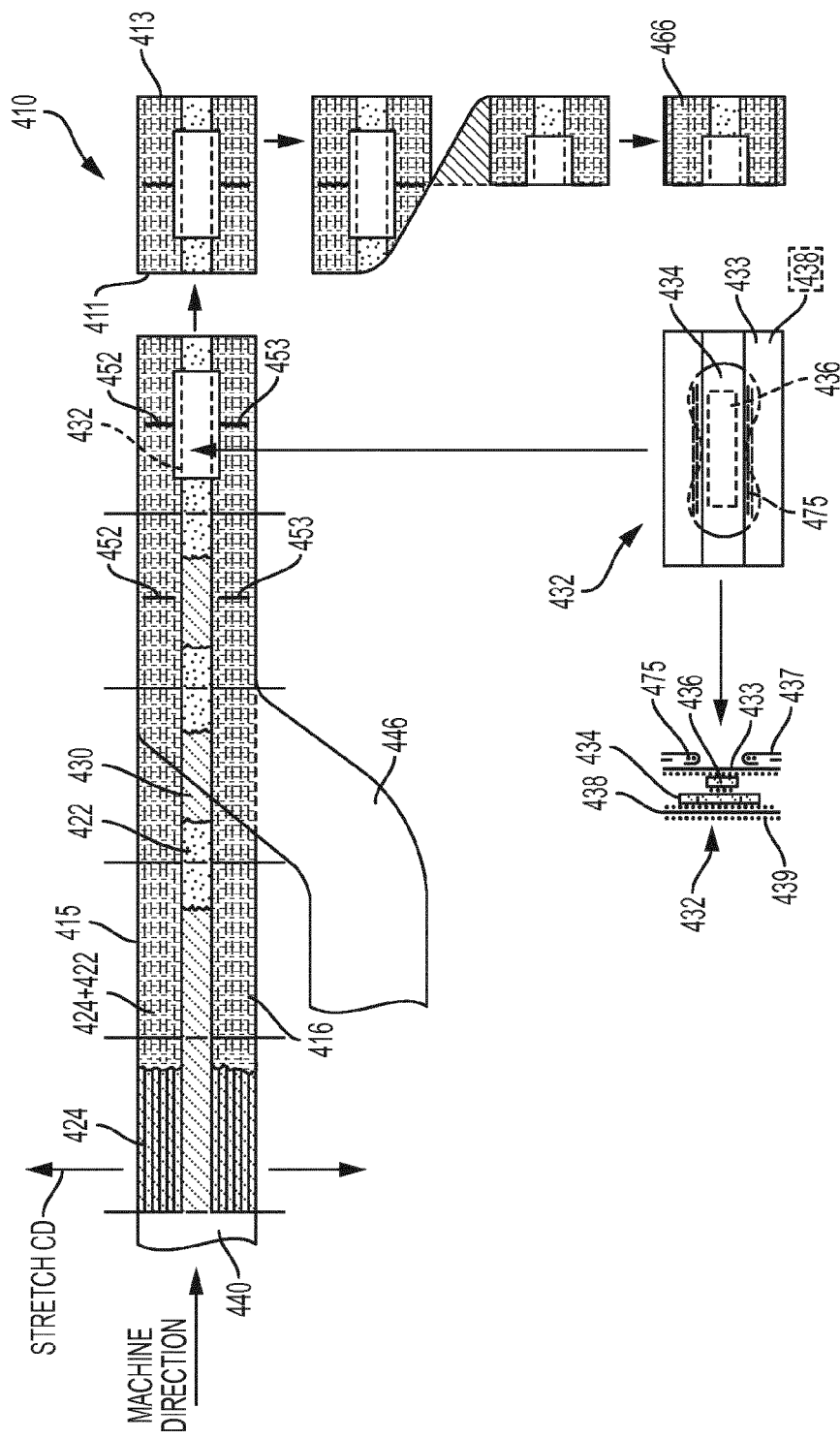
FIG. 54 is a schematic representation of a third exemplary method for manufacturing an absorbent article in accordance with the present disclosure.

FIG. 54 shows a method for manufacturing in which the longitudinal axis of the absorbent article that runs from the front edge 411 of the article through the length of the insert assembly 432 in the crotch portion 430 and to the rear edge 413 of the article is in the same direction as the machine direction of the web. Stretch adhesive is applied to a first non-woven web (e.g. substrate) 440, such as a Spunlace material. The stretch adhesive can be slot coated 424 and/or spray coated 422 onto the web. As shown here, stretch adhesive is provided in zones that run the machine direction. In this manner, the elastomeric composite stretch direction will be in the direction orthogonal to the machine processing direction (CD stretch). In the first and third zones, stretch adhesive is comb slot coated 424 first and then spray coated continuously throughout the entire zone. In the second zone, which runs down the middle of the absorbent article where the insert assembly 432 is to be placed, stretch adhesive is intermittently applied, such as by spray coating 422. The stretch adhesive is intermittently applied, such that adhesive is not applied where the absorbent layer is coupled to the web in the crotch portion 430. However, it is to be understood that, in other embodiments, stretch adhesive can be applied to the entire zone, even where the insert assembly 432 is to be coupled to the web. Prior to coupling the insert assembly 432 to the web, a second nonwoven web (e.g., substrate) 446 is aligned and coupled to the first nonwoven web 440, such that the stretch adhesive (i.e. elastomeric material) is sandwiched between the first and second nonwoven webs. Although not shown, it is to be understood that in embodiments wherein two elastomeric composites are to be combined to provide a unitized elastomeric panel with the absorbent core disposed there between, a second elastomeric material can be applied to the second non-woven web prior to the web being centered and aligned with the first web. However, in this embodiment, the absorbent core is to be added prior to aligning and centering the webs.

Referring back to FIG. 54, once the non-woven webs are aligned, the insert assembly 432 can be coupled to the surface of the second nonwoven web 446 facing away from the elastomeric material. The leg slits 452 and 453 can also be cut at this time. It is to be understood that although shown as straight lines, the slits can be any shape, such as those shapes shown in FIGS. 42A-D. Once the insert assembly 432 is coupled to the web, the web can be cut to produce discrete absorbent articles 410 in an unfolded configuration. The unfolded absorbent articles are then folded in half and the side edges 415 and 416 are sealed 466 to produce the final product.

Figure 55:
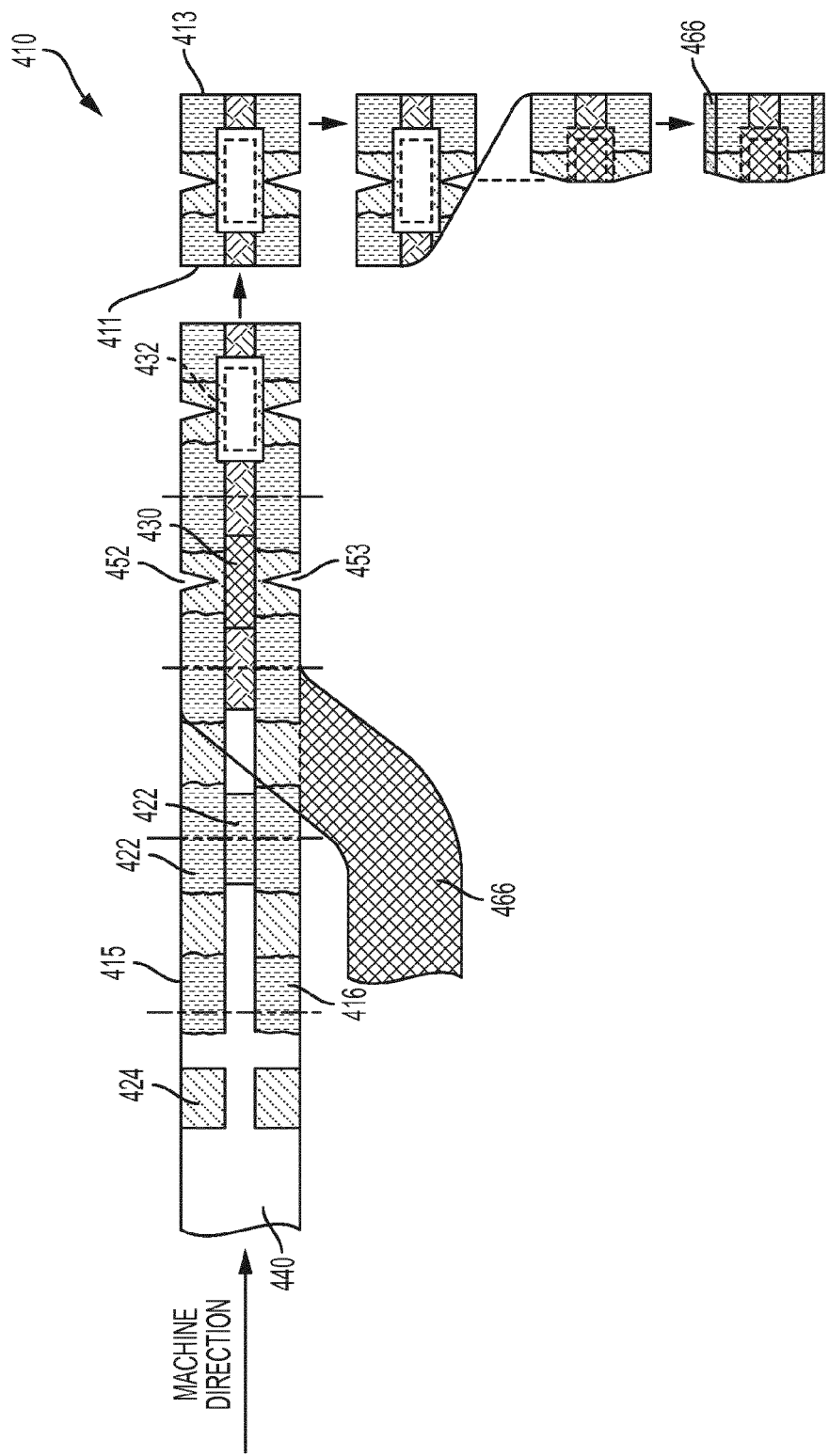
FIG. 55 is a schematic representation of a fourth exemplary method for manufacturing an absorbent article in accordance with the present disclosure.

As shown in FIG. 54, the insert assembly 432 positioned within the crotch portion 430 can includes stand up leg gatherings (SULG) 437, a top sheet 433, an acquisition layer 436 (or acquisition and distribution layer, "ADL"), an absorbent core 434, and a polymer film layer 438, all of which can be coupled to one another and the elastomeric composite via adhesive 439. The manufacturing process shown in FIG. 55 is similar to the process of FIG. 54, except for the application pattern of the stretch adhesive 420 and the leg cut-outs 452 and 453. Essentially, the manufacturing process of FIG. 55 provides a fluid-impervious barrier at the leg cut-out area of the product by slot coating stretch adhesive 424 around the entire leg opening 452 and 453. This can create a better gasket against leakage. As with the process depicted in FIG. 54, stretch adhesive is applied to a first non-woven web, such as a Spunlace material. The stretch adhesive can be slot coated 424 and/or spray coated 422 onto the web. As shown here, stretch adhesive 420 is provided in zones that run the machine direction. In this manner, the elastomeric composite stretch direction will be in the direction orthogonal to the machine processing direction ("CD" stretch). In the first and third zones, stretch adhesive is intermittently slot coated 424 and spray coated 422, such that stretch adhesive is applied throughout the entire first and third zones. In the second zone, which runs down the middle of the absorbent article where the insert assembly 432 is to be placed, stretch adhesive is intermittently applied, such as by spray coating 422. The stretch adhesive is intermittently applied, such that adhesive is not applied where the insert assembly 432 is coupled to the web. As with the process of FIG. 54, it is to be understood that, in other embodiments, stretch adhesive can be applied to the entire zone, even where the insert assembly 432 is to be coupled to the web.

Prior to coupling the insert assembly 432 to the web 440, a second nonwoven web 446 is aligned and coupled to the first nonwoven web 440, such that the stretch adhesive (i.e. elastomeric material) 424, 422 is sandwiched between the first 440 and second nonwoven 446 webs. Once the nonwoven webs are aligned, the leg cut-outs 452 and 453 can be provided. As shown here in FIG. 55, the leg cut-outs 452 and 453 are notched to provide angled leg openings. It is to be understood that although shown as notches, the cut-outs can be any shape. After the leg cut-outs are provided, the insert assembly 432 can be coupled to the surface of the second nonwoven web 446 facing away from the elastomeric material 422 and 424. Once the insert assembly 432 is coupled to the web, the web can be cut to produce discrete absorbent articles 410 in an unfolded configuration. The unfolded absorbent articles 410 are then folded in half and the side edges 415 and 416 are sealed (e.g., ultrasonic or heat seals) 466 to produce the final product.

Figure 56:
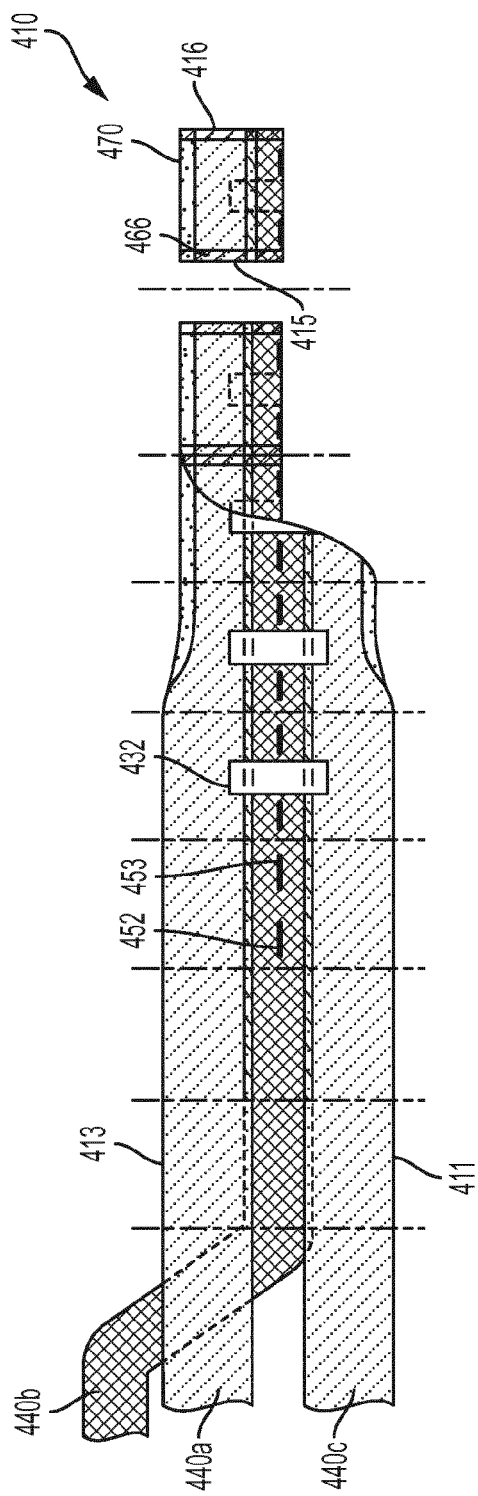
FIG. 56 is a schematic representation of a fifth exemplary method for manufacturing an absorbent article in accordance with the present disclosure.

In still another example of a manufacturing process, FIG. 56 depicts a process wherein there elastomeric composite webs are joined to provide the absorbent articles. In this embodiment, the longitudinal axis of the absorbent article that runs from the front edge 411 of the article through the length of the crotch portion 430 and to the rear edge 413 of the article is in a direction orthogonal to the machine processing direction, with the stretch of the absorbent article in the machine processing direction. A first elastomeric composite web 440a mostly comprises the front portion 412 of the absorbent article. A second elastomeric composite web 440b mostly comprises the crotch portion 430 of the absorbent article, and a third elastomeric composite web 440c mostly comprises the rear portion 414 of the absorbent article. The first 440a and third 440c elastomeric composite webs can be breathable, while the second elastomeric web 440b is preferably fluid-impervious. The fluid impervious web can be made of an elastic film that is laminated or ultrasonically bonded between two non-woven webs or the webs can be sprayed using any of the methods previously described. It is to be understood that any combination of breathable and fluid-impervious webs can be provided.

In the process shown in FIG. 56, the three elastomeric composite webs are aligned and centered with one another, such that the second elastomeric composite web 440b is provided mostly at the leg openings 452 and 453 and the crotch portion. Once the webs are centered and aligned, the leg openings 452 and 453 can be cut into the second web and the insert assembly can be coupled to at least the second web 440b, but can also overlap and be coupled to part of the first 440a and third webs 440c. Once the assembly 432 is coupled to the webs, the front 411 and rear 413 edges can be added to/folded over to form the waistband assembly. As shown in FIG. 56, the waistband is provided by folding over the edges 413 and 411 of the first and third webs, respectively. Prior to folding, elastic strands can be provided to the composite web toward the top edge and the bottom edge (not shown), such that the elastic strands are completely encompassed by the waistband assembly 470 once folded over. Once the waistband assembly is formed, the product can be folded in half, such that the front edge 411 and the rear edge 413 are aligned. The side edges 415 and 416 are then sealed together through, for example, bonding (e.g., ultrasonic or thermal bonding) 466. Once the edges are sealed, the product can be cut to provide discrete absorbent articles 410.

Figure 57:
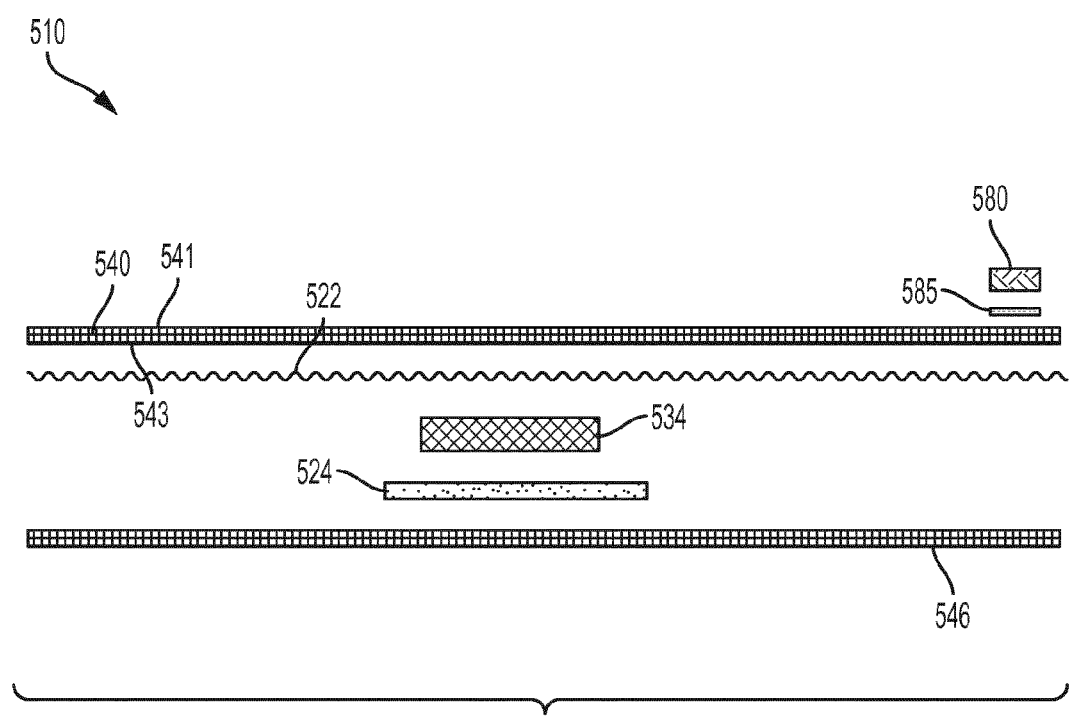
FIG. 57 is an exploded cross-sectional view of a wound care article consistent with the present disclosure.
Figure 58:
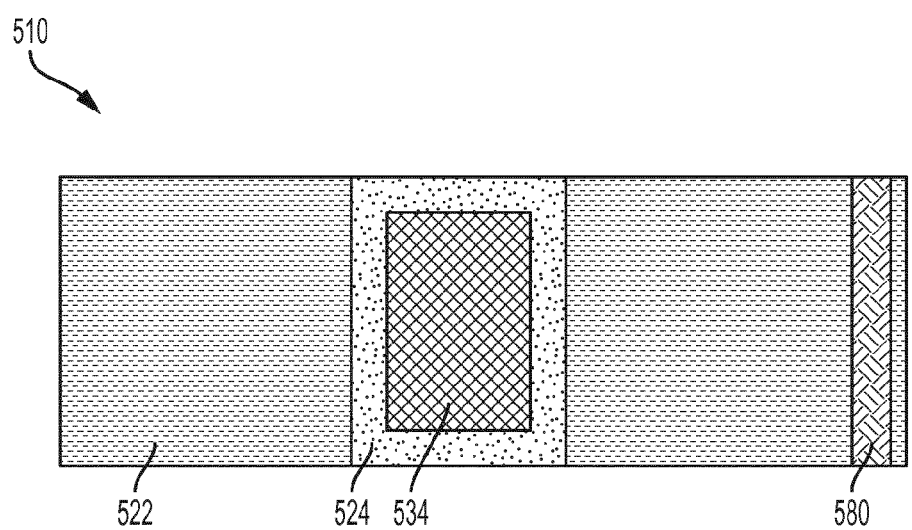
FIG. 58 is a top down view of the wound care article of FIG. 57.

In accordance with another embodiment of the present disclosure as shown in FIGS. 57 and 58, an absorbent article 510, such as a wound dressing, is provided that includes a top sheet 540 configured to face the user's body on a first side 541 of the top sheet 540, a back sheet 546, an elastomeric material 522 disposed between the top 540 and back sheet 546, and an absorbent core 534 disposed between the elastomeric material 522 and the back sheet 546, as shown in FIG. 56. In one aspect, the elastomeric material 522 is coextensive with the top sheet 540, such that it forms an elastomeric composite material that provides for a contoured fit to the body of the user.

The elastomeric material 522 can comprise an elastomeric film or adhesive, such as a stretch adhesive. In one preferred embodiment the elastomeric material 522 is a stretch adhesive. As with the absorbent article 410, an advantage to using stretch adhesive lies in the ability to manufacture the absorbent article 510 in the machine direction while providing stretch in the desired direction—the direction that is orthogonal to the machine direction (CD direction). Furthermore, by manufacturing the absorbent article 510 in the machine direction, the stretch adhesive can be applied to the top 540 and back 546 sheets in zones, and which allow for the provision of breathable and fluid-impervious adhesive regions at desired locations using a fully automated manufacturing process. In one aspect, the breathable regions are provided by spraying the stretch adhesive and the fluid-impervious regions are provided by slot-coating the stretch adhesive. In one embodiment, stretch adhesive is spray coated on the second side 543 (side facing away from the user) of the top sheet 540, such that the entire surface of the second side 543 is covered. This embodiment is preferred when breathability is desired. In another embodiment, stretch adhesive is slot coated on the second side 543 of the top sheet 540.

The absorbent core 534 can generally include an absorbent material, a nonabsorbent material, or any combination thereof. Exemplary materials include, but are not limited to, one or more of fluff pulp, airlaid paper, super absorbent polymer (SAP), super absorbent fibers, tissue, cotton fibers, rayon viscose, creped tissue, paper towel, and curly fibers. In one embodiment, the absorbent core 534 comprises a fluff pulp material, specifically a fluff pulp material that has one or more of exceptional absorbency rates, anti-bacterial properties, and is capable of capturing and neutralizing malodors, such as the Golden Isles fluff pulp (Grades 4865 and 4875) from Georgia Pacific in Atlanta, GA. In another embodiment, the absorbent core 534 comprises an airlaid material which does not contain SAP, such as Airlaid VH-145.101 (145 gsm) or HV-160.116 (160 gsm) from Glatfelter Falkenhagen GmbH in Pritzwalk, Germany.

The absorbent article 510 also includes, in one aspect, an adhesive layer 524 disposed between the absorbent core 534 and the back sheet 546 and coupled to the absorbent core 534. The adhesive layer 524 forms a fluid-impervious barrier to prevent fluid from leaking from the absorbent core 534. The adhesive layer can be coextensive with the absorbent core or the adhesive layer can extend at least partially beyond the edges of the absorbent core. In one embodiment, the adhesive layer 524 extends along the surface of the absorbent core 534 and at least partially beyond the edges the absorbent core 534, as shown in FIGS. 57 and 58. In this way, the adhesive extending beyond the absorbent core 534 helps to provide a fluid-impervious or high hydro-head seal around the perimeter of the absorbent core 534.

The adhesive layer 524 can comprise a stretch adhesive, construction adhesive, or any other adhesive for adhering non-woven materials to absorbent materials. In one embodiment, the adhesive layer 524 comprises a stretch adhesive, such as Conforma 9534-62-1 material from H. B. Fuller. In order to provide a fluid-impervious barrier to prevent fluid from leaking from the absorbent core 534, the stretch adhesive is preferably applied by slot-coating the adhesive to a portion of the back sheet 546, preferably the center portion, as shown in FIG. 57. Once the adhesive is applied to the back sheet 546, the absorbent material can be cut to a desired shape to form the absorbent core 534, centered, and placed on top of the adhesive layer 524, leaving a portion of the adhesive layer 524 exposed around the perimeter of the absorbent core 534.

Once the elastomeric material 522 is applied to the top sheet 540 and the absorbent core 534 and adhesive layer 524 are coupled to the back sheet 546, the top sheet 540 and back sheet 546 can be joined and nipped together under pressure. Once the sheets are joined together, they can be cut to create individual pieces. As shown in FIG. 58, the absorbent articles 510 are manufactured in the machine direction, such that each absorbent article 510 is cut along its length to create the individual pieces In another aspect, the absorbent article 510 includes an attachment mechanism 580 for securing the article 510 to the body of the user. The attachment mechanism 580 can be coupled to either of the top sheet 540 or the back sheet 546 on a surface facing away from the absorbent core 534. In one embodiment, the attachment mechanism 580 is located along the side edge of the top sheet, as shown in FIGS. 57 and 58. The attachment mechanism 580 is configured to attach to the back sheet 546 when placed on the body of the user in order to hold the absorbent article 510 in place. The attachment mechanism 580 can include any one or combination of micro-hooks, Velcro, adhesive, fastening tape, or any other means for attaching to non-woven material. In one embodiment, the attachment mechanism 580 is a micro hook, such as Microplast 85445 available from Gottlieb Binder GmbH & Co. KG located in Holzgerlingen, Germany.

In one aspect, to allow for the fluid to penetrate the top sheet 540 and be absorbed by the absorbent core 534, at least a portion of the top sheet 540 comprises a hydrophilic material, preferably the portion overlaying the absorbent core 534. The top sheet 540 can be made of, for example, nonwoven fibers, such as polypropylene (PP), polyethylene (PE), polyethylene terephthalate (PET), bi-component fibers (PE: sheath/PP core or PE sheath/PET core), polyester, cotton, cotton blend, viscose, rayon, etc. or any combination thereof; melt-blown nonwovens; spunlaid nonwovens, such as PP spunbounds and PET spunbounds; melt-blown and spunbound combinations (SM), including spun-melt-spun (SMS); and airlaid paper; or any combinations thereof. The top sheet 540 can be made hydrophilic through a surface treatment process that reduces the surface tension of the non-woven material, thus reducing the contact angle with the liquid and allowing the liquid to pass through the top sheet 540. In one embodiment, the top sheet 540 is made from a hydrophilic Spunlace non-woven material.

The top 540 and back 546 sheets may each be comprised of a single layer, as shown in FIG. 58, or each sheet may itself comprise multiple layers, such as 2, 3, 4, 5, 6, 7, 8, 9, 10, or more layers. When multiple layers are provided, the layers can all have the same thickness, each layer can have a different thickness, or some layers can have the same thickness while others have different thicknesses. Each layer can have a constant thickness or a variable thickness. Additionally, the layers can all be made up of the same material or of different materials, such as 2, 3, 4, 5, 6, 7, 8, 9, 10, or more different materials. Each layer itself can also be made up of more than one material (e.g., 2, 3, 4, 5, 6, 7, 8, 9, 10, or more), such that the materials are non-homogeneously distributed. Additionally, when one or both of the sheets 540 and 546 contain more than one layer, the elastomeric material 522 can be disposed within the layers, such that the electromeric material is coupled to two different layers within the sheet, such that the elastomeric material is coupled to two different layers within the sheet to form a multi-layered elastomeric composite.

In another aspect, to ensure that fluid does not leak out of the side of the article 510 facing away from the user's body, at least a portion of the back sheet 546 comprises a hydrophobic material. The back sheet 546 can be made from any non-woven material that prevents liquids from passing through, and is usually not surface treated. In one embodiment, the back sheet 546 is made from a hydrophobic Spunlace non-woven material. In addition, a fluid impervious material can be added and adhered in between the absorbent core 534 and Back Sheet 546, such as a polymer film. The polymer film layer would completely cover the bottom portion and entire perimeter of the absorbent core 534. It may also extend just beyond the perimeter of the absorbent core.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A disposable absorbent garment comprising:
a body comprising:
a front body section configured to be fitted against a front, or anterior, portion of a wearer's body, and a rear body section configured to be fitted against a rear, or superior, portion of the wearer's body; and
a crotch section positioned between and coupled to the front and rear body sections, the crotch section configured to be fitted against a crotch region of the wearer's body; wherein
the crotch section comprises an insert assembly having at least an absorbent core comprising a liquid-absorbing material; and wherein the absorbent core is positioned between two longitudinal edges of the insert assembly;
wherein the front body section, and the rear body section comprises
an elastomeric composite comprising
an elastomeric material and
wherein said front and rear body sections are configured to stretch upon application of a force thereto;
wherein the front body section and/or rear body section comprises leg elastics which overlap with the two longitudinal edges of the insert assembly and wherein said leg elastics do not extend over the absorbent core.

2. The disposable absorbent garment of claim 1, wherein the absorbent core defines an absorbent core area and wherein said absorbent core area is free of elastomeric material.

3. The disposable absorbent garment of claim 1, wherein the insert assembly further comprises an acquisition layer disposed between the absorbent core and a first substrate layer, wherein the insert assembly further comprises of a polymer film barrier disposed between the absorbent core and a second substrate layer.

4. The disposable absorbent garment of claim 1, wherein the insert assembly further comprises stand up leg gathers (SULGs) and wherein the insert assembly further comprises crotch elastics, wherein said crotch elastics extend parallel to the absorbent core.

5. The disposable absorbent garment of claim 1, wherein the leg elastics of the elastomeric composite of the front body section are configured to stretch in a direction transverse to a longitudinal axis of the absorbent core and wherein at least a portion of said leg elastics extend perpendicular to said longitudinal axis of the absorbent core.

6. The disposable absorbent garment of claim 1, wherein a seam region of the elastomeric composite is substantially free of the elastomeric material.

7. The disposable absorbent garment of claim 1, the garment further comprises stretch adhesive that is applied to at least one of the front body section, rear body section, and crotch section by a combination of spraying and slot coating the stretch adhesive onto at least one of two substrate layers to form the elastomeric composite.

8. The disposable absorbent garment of claim 7, wherein elastomeric composite has breathable regions and fluid impervious regions, wherein the breathable regions are provided by sprayed stretch adhesive and wherein the fluid impervious regions are provided by slot coated stretch adhesives.

9. The disposable absorbent garment according to claim 1, wherein the elastomeric composite comprises a stretch adhesive is positioned between at least two substrate layers, wherein said at least two substrate layers are coupled together by way of a seal at a bonded seam region that is free of the stretch adhesive; and
wherein a reinforcement nonwoven material is arranged at the seam region between the two substrate layers, and such that the reinforcement nonwoven material overlaps with the stretch adhesive.

10. The disposable absorbent garment according to claim 1,
wherein the garment comprises a stretch adhesive that is arranged surrounding a perimeter of the absorbent core acting as a gasket to prevent leaks.

11. The disposable absorbent garment according to claim 1, wherein the insert assembly is provided with crotch elastics that are extending along the longitudinal edges of the insert assembly and wherein said crotch elastics overlap with the elastomeric composite within the front and rear body sections.

12. A disposable absorbent garment comprising:
a body comprising:
a front body section configured to be fitted against a front, or anterior, portion of a wearer's body, and a rear body section configured to be fitted against a rear, or superior, portion of the wearer's body; and
a crotch section positioned between and coupled to the front and rear body sections, the crotch section configured to be fitted against a crotch region of the wearer's body, wherein
the crotch section comprises an absorbent insert assembly having at least an absorbent core comprising a liquid-absorbing material;
said absorbent insert assembly having two longitudinal edges and upper and lower traversal edges;
wherein the front body section, and the rear body section comprises
an elastomeric composite comprising
an elastomeric material, and
wherein said front and rear body sections are configured to stretch upon application of a force thereto;

wherein the elastomeric composite comprises a stretch adhesive or an elastic film positioned between and coupled to at least two substrate layers to form a multi-layered elastomeric composite;

wherein the stretch adhesive or the elastic film covers between 15-99% of a substrate layer to which it is coupled;

and wherein the stretch adhesive or the elastic film overlaps with the upper and lower traversal edges of the absorbent insert assembly.

13. The disposable absorbent garment of claim 12, wherein the at least two substrate layers comprise the same material and wherein the elastomeric composite comprises a stretch adhesive that covers up 25% to 99% of the substrate layer to which it is coupled.

14. The disposable absorbent garment of claim 13, wherein the at least two substrate layers comprise a spunlace nonwoven material and wherein the stretch adhesive covers up 50% to 99% of the substrate layer to which it is coupled and wherein the stretch adhesive overlaps with the absorbent core.

15. The disposable absorbent garment of claim 12, wherein the at least two substrate layers are coupled together by way of a seal.

16. The disposable absorbent garment of claim 15, wherein a bonded seam region of the elastomeric composite is substantially free of the elastomeric material.

17. The disposable absorbent garment of claim 12, wherein at least two of the substrate layers comprise a spunlace nonwoven and another one of the substrate layers comprises a reinforcement nonwoven material.

18. The disposable absorbent garment of claim 17, wherein the two substrate layers of spunlace nonwoven material and one substrate layer of reinforcement nonwoven material are coupled together by one of a mechanical and heat crimp seal and an ultrasonically bonded seal at a seam region, wherein the seam region of the elastomeric composite is substantially free of the elastomeric material, and wherein the reinforcement nonwoven material is positioned between the two substrate layers of spun lace nonwoven material.

19. The disposable absorbent garment of claim 18, wherein the elastomeric material is a stretch adhesive that is applied between the spunlace nonwoven layers and wherein sides of the stretch adhesive overlap with edges of the reinforcement nonwoven material.

20. The disposable absorbent garment of claim 12, wherein the front body portion includes a belly portion and the rear body portion includes a waist portion, and wherein the elastomeric material includes elastic strands arranged in such a manner as to provide cross directional stretching along the belly portion and the waist portion; and wherein the stretch adhesive covers between 20-99% of a substrate layer to which it is coupled.

21. A disposable absorbent garment comprising:

a body comprising:

a front body section configured to be fitted against a front, or anterior, portion of a wearer's body, and a rear body section configured to be fitted against a rear, or superior, portion of the wearer's body; and a crotch section coupled to the front and rear body sections, the crotch section configured to be fitted against a crotch region of the wearer's body;

wherein the front body section, and the rear body section comprises an elastomeric composite comprising an elastomeric material; and wherein the front body section and the rear body section are configured to stretch upon application of a force thereto;

wherein the elastomeric material includes both breathable and substantially fluid-impervious regions;

wherein the breathable regions are provided by sprayed stretch adhesive and wherein the substantially fluid-impervious regions are provided by slot-coated stretch adhesive on the substrate layers.

* * * * *